US012618846B2

(12) United States Patent
Bruns et al.

(10) Patent No.: US 12,618,846 B2
(45) Date of Patent: May 5, 2026

(54) METHOD AND DEVICE FOR IMAGING FLUORESCENT PROTEINS IN NEAR- AND SHORT-WAVE INFRARED

(71) Applicants: HELMHOLTZ ZENTRUM MÜNCHEN—DEUTSCHES FORSCHUNGSZENTRUM FÜR GESUNDHEIT UND UMWELT (GMBH), Neuherberg (DE); THE REGENTS OF THE UNIVERSITY OF CALIFORNIA, Oakland, CA (US)

(72) Inventors: Oliver Bruns, Neuherberg (DE); Jakob Lingg, Neuherberg (DE); Juan-Pablo Fuenzalida-Werner, Neuherberg (DE); Andre Stiel, Neuherberg (DE); Martin Warmer, Neuherberg (DE); Shyam S. Ramakrishnan, Neuherberg (DE); Emily Cosco, East Los Angeles, CA (US); Ellen Sletten, East Los Angeles, CA (US)

(73) Assignees: HELMHOLTZ ZENTRUM MÜNCHEN—DEUTSCHES FORSCHUNGSZENTRUM FÜR GESUNDHEIT und UMWELT (GMBH), Neuherberg (DE); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1093 days.

(21) Appl. No.: 17/617,261

(22) PCT Filed: Jun. 7, 2020

(86) PCT No.: PCT/EP2020/065754
§ 371 (c)(1),
(2) Date: Dec. 7, 2021

(87) PCT Pub. No.: WO2020/245447
PCT Pub. Date: Dec. 10, 2020

(65) Prior Publication Data

US 2022/0236280 A1 Jul. 28, 2022

Related U.S. Application Data

(60) Provisional application No. 62/858,461, filed on Jun. 7, 2019.

(51) Int. Cl.

| | |
|---|---|
| ***G01N 33/58*** | (2006.01) |
| ***A61B 5/00*** | (2006.01) |
| ***G01N 21/64*** | (2006.01) |

(52) U.S. Cl.
CPC ......... *G01N 33/582* (2013.01); *A61B 5/0071* (2013.01); *G01N 21/6428* (2013.01); *G01N 21/6456* (2013.01); *G01N 2021/6439* (2013.01)

(58) Field of Classification Search
CPC ............. G01N 33/582; G01N 21/6428; G01N 21/6456; G01N 2021/6439; A61B 5/0071
See application file for complete search history.

(56) References Cited

U.S. PATENT DOCUMENTS

| | | | |
|---|---|---|---|
| 7,477,931 | B2 | 1/2009 | Hoyt |
| 8,802,424 | B2 | 8/2014 | Luong et al. |

(Continued)

FOREIGN PATENT DOCUMENTS

| | | | |
|---|---|---|---|
| WO | 2017/160639 | A1 | 9/2014 |
| WO | 2018226720 | A1 | 12/2018 |

OTHER PUBLICATIONS

Bomati et al., Spectral and structural comparison between bright and dim green fluorescent proteins in Amphioxus. Sci Rep. Jun. 27, 2014;4:5469.

(Continued)

*Primary Examiner* — Brian J. Sines
(74) *Attorney, Agent, or Firm* — Michael A . Whittaker

(57) ABSTRACT

The present invention relates to systems, methods and fluorescent polypeptide for real-time multicolor shortwave infrared fluorescence imaging. The systems and methods of the present invention further relate to real-time multi-color in vivo SWIR imaging systems employing high-power exci- (Continued)

tation sources in combination with state of the art InGaAs SWIR detectors and SWIR illuminated fluorescent polypeptide.

16 Claims, 26 Drawing Sheets

Specification includes a Sequence Listing.

(56) References Cited

U.S. PATENT DOCUMENTS

| | | | |
|---|---|---|---|
| 2015/0030542 | A1 | 1/2015 | Singhal |
| 2017/0107562 | A1 | 4/2017 | Rothberg et al. |

OTHER PUBLICATIONS

Carr et al., Absorption by water increases fluorescence image contrast of biological tissue in the shortwave infrared. Proc Natl Acad Sci U S A. Sep. 11, 2018;115(37):9080-9085.

Chee et al., In vivo photoacoustic difference-spectra imaging of bacteria using photoswitchable chromoproteins. J Biomed Opt. Oct. 2018;23(10):1-11.

Lambert, FPbase: a community-editable fluorescent protein database. Nat Methods. Apr. 2019;16(4):277-278.

Rodriguez et al., A far-red fluorescent protein evolved from a cyanobacterial phycobiliprotein. Nat Methods. Sep. 2016;13(9):763-769.

Shaner et al., Improved monomeric red, orange and yellow fluorescent proteins derived from *Discosoma* sp. red fluorescent protein. Nat Biotechnol. Dec. 2004;22(12):1567-1572.

SShcherbakova and Verkhusha, Near-infrared fluorescent proteins for multicolor in vivo imaging. Nat Methods. Aug. 2013;10(8):751-754.

Zeiss Campus, Spectral imaging. zeisscampus.magnet.fsu.edu. [Online] 2019, accessed at: https://www.zeisscampus.magnet.fsu.edu/tutorials/spectralimaging/lambdastack/indexflash.html.

International Search Report issued in PCT/EP2020/065754 on Sep. 30, 2020 (6 pages).

Written Opinion issued in PCT/EP2020/065754 on Sep. 30, 2020 (8 pages).

Byrd et al., "Multi-angle projection imaging of short-wave infrared (SWIR) fluorescence for small animal optical tomography", Proc SPIE Int Soc Opt Eng. Feb. 2019;10862:108620E. doi: 10.1117/12.2510652. Epub Mar. 7, 2019.

Carr et al., "Shortwave infrared fluorescence imaging with the clinically approved near-infrared dye indocyanine green", Proc Natl Acad Sci U S A. Apr. 24, 2018;115(17):4465-4470. doi: 10.1073/pnas.1718917115. Epub Apr. 6, 2018.

Diao et al., "Fluorescence Imaging In Vivo at Wavelengths beyond 1500 nm", Angew Chem Int Ed Engl. Dec. 1, 2015;54(49):14758-62. doi: 10.1002/anie.201507473. Epub Oct. 13, 2015.

Muller et al., "Pulsed interleaved excitation", Biophys J. Nov. 2005;89(5):3508-22. doi: 10.1529/biophysj.105.064766. Epub Aug. 19, 2005.

Tsukasaki et al., "A short-wavelength infrared emitting multimodal probe for non-invasive visualization of phagocyte cell migration in living mice", Chem Commun (Camb). Nov. 28, 2014;50(92):14356-9. doi: 10.1039/c4cc06542e.

TdTomato Dye Profile from FluoroFinder retreived from app.fluorofinder.com/dyes/148-tdtomato-exmax-554-nm-em-max-581-nm 2025.

CONTROL CIRCUITRY

A.

1–11

B.

10 (MeO7) 11 (IR-27) 1 (Flav7) 2 5 abs (nm)

9 8 4 6 7 3 (Julo7)

C.

D.

E. Photophysics of flavylium heptamethine fluorophores in DCM

| dye | $\lambda_{max,abs}$ (nm) | $\varepsilon_{max}$ ($M^{-1}cm^{-1}$) | $\lambda_{max,em}$ (nm) | $\Phi_F$ (%) | brightness($\varepsilon_{max}$) ($M^{-1}cm^{-1}$) |
|---|---|---|---|---|---|
| **1** (Flav7) | 1027 | 241,000 | 1053 | 0.61 | 1470 |
| **2** | 1033 | 190,000 | 1057 | 0.62 | 1180 |
| **3** (Julo7) | 1061 | 238,000 | 1088 | 0.46 | 1090 |
| **4** | 1029 | 207,000 | 1056 | 0.51 | 1060 |
| **5** | 1034 | 247,000 | 1061 | 0.48 | 1190 |
| **6** | 1032 | 110,000 | 1060 | 0.54 | 590 |
| **7** | 1047 | 210,000 | 1078 | 0.58 | 1220 |
| **8** | 1021 | 140,000 | 1048 | 0.45 | 630 |
| **9** | 998 | 108,000 | 1022 | 0.42 | 450 |
| **10** (MeO7) | 984 | 190,000 | 1008 | 0.52 | 990 |
| **11** (IR-27) | 987 | 231,000 | 1011 | 0.35 | 810 |

METHOD AND DEVICE FOR IMAGING FLUORESCENT PROTEINS IN NEAR- AND SHORT-WAVE INFRARED

CROSS-REFERENCE TO RELATED APPLICATIONS

The present invention is filed under 35 U.S.C. § 371 as the U.S. national phase of International Application No. PCT/EP2020/065754, filed Jun. 7, 2020, which designated the United States and which claims the right of priority of U.S. Provisional Application No. 62/858,461, filed Jun. 7, 2019. The entire disclosures of the above-identified priority applications are hereby fully incorporated herein by reference.

The instant application contains a Sequence Listing which has been submitted in ASCII format via EFS-Web and is hereby incorporated by reference in its entirety. Said ASCII copy, created on Dec. 7, 2021, is named SCH-5200-US SeqListing.txt and is 144 kilobytes in size.

TECHNICAL FIELD

The shortwave infrared (SWIR, e.g., in the range 1000-2000 nm) region of the electromagnetic spectrum has provided a means to real-time monitoring of whole mammals with high contrast and resolution. While many inorganic and organic fluorophores have been developed for this region, multiplexed experiments have been limited due to near infrared (NIR, e.g., in the range 700-1000 nm) excitation wavelengths of often broad and overlapping absorption profiles.

The present invention relates to systems, methods and fluorescent polypeptide for real-time multicolor shortwave infrared fluorescence imaging. The systems and methods of the present invention further relate to real-time multi-color in vivo SWIR imaging systems employing high-power excitation sources in combination with state of the art InGaAs SWIR detectors and SWIR illuminated fluorescent polypeptide.

The present invention further relates to fluorescence imaging that is an essential technology in biological research. The principle concept of fluorescence imaging requires a (labelled) fluorescent biological sample, an optical setup (microscopic, mesoscopic or macroscopic) for detection and an excitation light source (FIG. 17).

BACKGROUND OF THE INVENTION

There exist systems that are capable of performing in vivo SWIR imaging (e.g., WO2017160639A1). The indium gallium arsenide (InGaAs) detectors are restricted for commercial use and are bound by law enforcement services due to their applications in military surveillance and weapon defense systems. These detectors also lag behind in commercial development due to the high associated development cost. However, there exist a number of commercially available high-throughput InGaAs detector-based camera systems.

The diode-based VIS (visible light), NIR or SWIR light sources are a mature technology, however the high power current driven VIS, NIR or SWIR light sources are safety critical apparatus and there exist relatively smaller number of system developers and service providers. The recent developments in this industry has resulted fiber-coupled light-sources with dedicated current controllable driver units.

The trigger control devices are common apparatus used for imaging in visible spectrum. However, there is no known system that provides complete integration of high-power VIS/NIR/SWIR light sources with SWIR detectors for the purpose of in vivo imaging of biological structures.

Prevailing in vivo real-time multicolor optical imaging systems employ visible or near-infrared spectrum for fluorescence imaging. When applied to characterize biological structures, such imaging apparatus provide sub-standard results due to higher photon scattering in biological tissues as opposed to the short-wave-infrared (SWIR) imaging systems. The short-wave-infrared imaging techniques provide better contrast and clarity in imaging due to higher transmission through biological tissues and reduced autofluorescence. However, the existing SWIR imaging systems are not capable of synthesizing a multicolor real-time in vivo imaging (e.g., acquiring 25 frames per second and faster) of biological structures. The excitation sources and detectors are not capable of handling external control for synchronized acquisition. The HDR imaging of biological structures is limited in existing SWIR imaging device and methods due to low throughput design of detectors. The controllability and scalability of the existing SWIR imaging apparatus are limited.

Additionally, a real-time multi-channel fluorescence imaging system (e.g., acquiring 25 frames per second and faster) in SWIR spectrum is not yet available for commercial use due to the technical challenges faced in the development of high-throughput SWIR detectors and SWIR targeted fluorophores.

On the other hand, every year imaging devices are sold for microscopic imaging (e.g., Zeiss, Leica, Olympus etc.) and for macroscopic whole-mouse imaging (e.g., Perkin Elmer, etc.). The price of those devices could, for example, range from 100000 € (e.g., epifluorescence microscope) to 1000000 € (e.g., multiphoton and surgical microscopes) and higher. The global microscopy market has been estimated to reach up to 5756 billion $ in 2019 (https://www.statista.com/statistics/523127/world-microscopy-market-value-forecast/).

Biological imaging, independent of macro or micro imaging, relies on labelled biological samples. For preclinical research those samples are commonly labelled using fluorescent proteins. There are more than 687 fluorescent proteins in use (e.g., https://www.fpbase.org/). Mice are breed to express fluorescent proteins under genetic control in all biomedical research fields. An example is using the green fluorescent protein GFP; for this example, one can find 1123 mouse lines labelled with GFP from one commercial supplier alone (e.g., https://www.jax.org/) and this is only one of the 687 established fluorescent proteins. Hence, one can estimate the number of all mouse models that are labelled with fluorescent proteins to be much higher.

Therefore, fluorescent imaging using fluorescent proteins is an important market and that it is an essential tool for the daily tasks of biologists. Fluorescent proteins emit the largest portion of light in the visible range (e.g., 400-700 nm). Hence, most imaging setups are built for this wavelength regime today. However, the resolution, contrast and penetration depth are strongly limited in the visible range (e.g., 400-700 nm). The lack of labelled biological samples that are optimized for the NIR and SWIR range is perceived as a current boundary for biological imaging in the SWIR.

SUMMARY OF THE INVENTION

The present invention relates to systems for imaging a biological sample (e.g., a tissue, e.g., in vivo, ex vivo or in vitro tissue; an organ, whole body or a fragment/s or portion/s thereof, comprising:

i) a fluorescent probe comprising a fluorescent polypeptide;

ii) an excitation source configured to emit electromagnetic radiation within an absorption spectrum of the fluorescent polypeptide; and iii) a detector configured to detect the tail portion (e.g., said tail portion is not within the emission peak wavelength range of said fluorescent polypeptide) of the fluorescence of the fluorescent polypeptide, wherein said detector is configured to detect in the near infrared (NIR) wavelength range of the electromagnetic spectrum (e.g., in the wavelength range from about 700 nm to about 1000 nm) and/or in the shortwave infrared (SWIR) wavelength range of electromagnetic spectrum (e.g., in the wavelength range from about 1000 nm to about 2500 nm).

The present invention relates to a method for imaging a biological sample (e.g., a tissue, e.g., in vivo, ex vivo or in vitro tissue; an organ, whole body or a fragment/s or portion/s thereof) comprising:

i) exposing at least a portion of said biological sample (e.g., a portion of said tissue) comprising a fluorescent probe to a suitable excitation source of the fluorescent probe, wherein the fluorescent probe comprises a fluorescent polypeptide; and ii) detecting the tail portion (e.g., said tail portion is not within the emission peak wavelength range of said fluorescent polypeptide) of the fluorescence of the fluorescent polypeptide, wherein said detecting is carried out in the near infrared (NIR) wavelength range of the electromagnetic spectrum (e.g., in the wavelength range from about 700 nm to about 1000 nm) and/or in the shortwave infrared (SWIR) wavelength range of the electromagnetic spectrum (e.g., in the wavelength range from about 1000 nm to about 2500 nm).

The present invention further relates to a method for multiplexed and/or multicolor imaging (e.g., with VIS/NIR/SWIR fluorophores, preferably polymethine fluorophores/dyes, e.g., ICG and/or Julo7, e.g., WO 2018/226720A1) of a sample location, said method comprising:

i) exposing a portion of said sample location to a first light pulse/s (e.g., an excitation light pulse/s), wherein said first light pulse/s having:

(a) a first state (e.g., said state has one or more of the properties of a wavelength and/or spectrum; e.g., linear, circular and elliptical polarization, intensity, incident angle and pulse length); or (b) a first wavelength;

in order to illuminate (e.g., for reflectance imaging) or excite a first component (e.g., fluorescent component, e.g., VIS/NIR/SWIR fluorophores, preferably polymethine fluorophores/dyes, e.g., ICG, IRDye800CW, Julo5 and/or Julo7 (e.g., WO 2018/226720A1), or an autofluorescent tissue component, e.g., a pigment/s, preferably lipofuscin), chemical composition, surface and/or region in the portion of said sample location (e.g., a first dye comprised by the portion of said sample location);

ii) exposing the portion of said sample location to at least a second light pulse/s (e.g., a second excitation light pulse/s) having:

(c) a second state (e.g., said state has one or more of the properties of a wavelength and/or spectrum; e.g., linear, circular and elliptical polarization, intensity, incident angle and pulse length), which is different from the first state of (a); or (d) a second wavelength, which is different from the first wavelength of (b);

in order to illuminate (e.g., for reflectance imaging) or excite a second component (e.g., fluorescent component, e.g., VIS/NIR/SWIR fluorophores, preferably polymethine fluorophores/dyes, e.g., ICG, IRDye800CW, Julo5 and/or Julo7 (e.g., WO 2018/226720A1), or an autofluorescent tissue component, e.g., a pigment/s, preferably lipofuscin), chemical composition, surface and/or region in the portion of said sample location (e.g., a second dye comprised by the portion of said sample location), preferably said second component, chemical composition, surface or region is different from said first component, chemical composition, surface or region; wherein the first light pulse/s (e.g., the first excitation light pulse/s) and the second (and/or subsequent) light pulse/s (e.g. the second excitation light pulse/s) are provided sequentially;

iii) detecting light reflected or emitted by the first and the second component (e.g., fluorescent components or dyes e.g., ICG, IRDye800CW, Julo5 and/or Julo7 (e.g., WO 2018/226720A1), chemical composition, surface and/or region in the portion of said sample location (e.g., the first and the second fluorescent components or dyes, e.g., ICG, IRDye800CW, Julo5 and/or Julo7 (e.g., WO 2018/226720A1)) by an imaging device, wherein the peak emission wavelength of at least one component, chemical composition, surface and/or region in the portion of said sample location lies outside of the detection range of the imaging device, the detection process including:

aa) switching the imaging device, in a sequential manner, between a first configuration (or state) during which the imaging device is responsive to a first electromagnetic radiation and a second configuration (or state) during which the imaging device is responsive to a second electromagnetic radiation (e.g., said first and second electromagnetic radiations are not identical); wherein the switching of the first configuration (or state) is triggered by the provision of the light pulse/s (e.g., by the means of provision of electrical pulses to the light sources).

The present invention further relates to systems for multiplexed and/or multicolor imaging (e.g., a fluorescent component, e.g., VIS/NIR/SWIR fluorophores, preferably polymethine fluorophores/dyes, e.g., ICG, IRDye800CW, Julo5 and/or Julo7 (e.g., WO 2018/226720A1), or an autofluorescent tissue component, e.g. a pigment/s, preferably lipofuscin) of sample locations, said system comprising:

i) a first laser light source configured to operate at a first wavelength;

ii) at least a second light source (e.g., laser light source or LED) configured to operate at a second wavelength;

iii) an imaging device configured to detect electromagnetic radiation;

iv) a control unit coupled to the first laser light source, the second laser light source and the imaging device, wherein the control unit is configured to control the first laser light source to provide first excitation light pulse/s and to control the second laser light source to provide second excitation light pulse/s in sequential manner; wherein the control unit is further configured to switch the imaging device in a sequential manner, between a first state during which the imaging device is responsive to a first electromagnetic radiation and a second state during which the imaging device is responsive to a second electromagnetic radiation (e.g., said first and second electromagnetic radiations are not identical); wherein the system is configured such that the switching of the imaging device into the first state is triggered by the provision of the light pulse/s (e.g., by the means of provision of electrical pulses to the light sources).

The present application satisfies this demand by the provision of the methods, systems and suitable fluorophores (e.g., fluorescent component, e.g., VIS/NIR/SWIR fluorophores, preferably polymethine fluorophores/dyes, e.g., ICG, IRDye800CW, Julo5 and/or Julo7 (e.g., WO 2018/226720A1), or an autofluorescent tissue component, e.g. pigment/s, preferably lipofuscin) and fluorescent polypeptides as described herein below (e.g., SEQ ID NO: 1-5), characterized in the claims and illustrated by the appended Examples and Figures.

Overview of the Sequence Listing

As described herein references are made to GenBank Accession Numbers (https://www.ncbi.nlm.nih.gov/protein/, e.g., as available in GeneBank Release 230 of Feb. 15, 2019 (https://www.ncbi.nlm.nih.gov/genbank/release/230/).

SEQ ID NO: 1 is the amino acid sequence of tandem-dimer red fluorescent protein [synthetic construct]. GenBank Accession Number: AAV52169.1. tdTomato is a basic (constitutively fluorescent) orange fluorescent protein published in 2004, derived from *Discosoma* sp. (Shaner et al., *Nature Biotechnology,* 22(12), 1567-1572. doi: 10.1038/nbt1037). It is reported to be a somewhat slowly-maturing tandem dimer with low acid sensitivity.

SEQ ID NO: 2 is the amino acid sequence of far-red fluorescent protein smURFP [synthetic construct]. GenBank Accession Number: ANW47198.1. smURFP is a basic (constitutively fluorescent) near ir fluorescent protein published in 2016, derived from *Trichodesmium erythraeum* IMS101 (Rodriguez et al., 2016, Nat Methods. 2016 September; 13(9):763-9. doi: 10.1038/nmeth.3935).

SEQ ID NO: 3 is the amino acid sequence of near-infrared fluorescent protein iRFP720 [synthetic construct]. GenBank Accession Number: AGN32866.1. iRFP720 is a basic (constitutively fluorescent) near ir fluorescent protein published in 2013, derived from *Rhodopseudomonas palustris* (Shcherbakova and Verkhusha 2013*, Nature Methods,* 10(8), 751-754. doi: 10.1038/nmeth.2521). It has low acid sensitivity. It requires the cofactor biliverdin for fluorescence.

SEQ ID NO: 4 is the amino acid sequence of the fluorescent polypeptide derived from *Montipora* sp. 20.

SEQ ID NO: 5 is the amino acid sequence of the fluorescent protein mRed7.

SEQ ID NO: 6 is the amino acid sequence of the fluorescent protein RRvT.

SEQ ID NO: 7 is the amino acid sequence of the fluorescent protein tdTomato.

SEQ ID NO: 8 is the amino acid sequence of the fluorescent protein tdimer2(12).

SEQ ID NO: 9 is the amino acid sequence of the fluorescent protein pcDropna2.

SEQ ID NO: 10 is the amino acid sequence of the fluorescent protein mScarlet.

SEQ ID NO: 11 is the amino acid sequence of the fluorescent protein mKO kappa.

SEQ ID NO: 12 is the amino acid sequence of the fluorescent protein TurboRFP.

SEQ ID NO: 13 is the amino acid sequence of the fluorescent protein PSmOrange.

SEQ ID NO: 14 is the amino acid sequence of the fluorescent protein RFP611.

SEQ ID NO: 15 is the amino acid sequence of the fluorescent protein mRuby3.

SEQ ID NO: 16 is the amino acid sequence of the fluorescent protein vsfGFP-0.

SEQ ID NO: 17 is the amino acid sequence of the fluorescent protein LanYFP.

SEQ ID NO: 18 is the amino acid sequence of the fluorescent protein dLanYFP.

SEQ ID NO: 19 is the amino acid sequence of the fluorescent protein dVFP.

SEQ ID NO: 20 is the amino acid sequence of the fluorescent protein ccal YFP1.

SEQ ID NO: 21 is the amino acid sequence of the fluorescent protein efas GFP.

SEQ ID NO: 22 is the amino acid sequence of the fluorescent protein pcDronpa (green).

SEQ ID NO: 23 is the amino acid sequence of the fluorescent protein aeur GFP.

SEQ ID NO: 24 is the amino acid sequence of the fluorescent protein mRFP720.

SEQ ID NO: 25 is the amino acid sequence of the fluorescent protein iRFP720.

SEQ ID NO: 26 is the amino acid sequence of the fluorescent protein Wi-Phy.

SEQ ID NO: 27 is the amino acid sequence of the fluorescent protein SNIFP.

SEQ ID NO: 28 is the amino acid sequence of the fluorescent protein iFP2.0.

SEQ ID NO: 29 is the amino acid sequence of the fluorescent protein iRFP713.

SEQ ID NO: 30 is the amino acid sequence of the fluorescent protein iFP1.4.

SEQ ID NO: 31 is the amino acid sequence of the fluorescent protein mIFP.

SEQ ID NO: 32 is the amino acid sequence of the fluorescent protein miRFP709.

SEQ ID NO: 33 is the amino acid sequence of the fluorescent protein miRFP.

SEQ ID NO: 34 is the amino acid sequence of the fluorescent protein M355NA.

SEQ ID NO: 35 is the amino acid sequence of the fluorescent protein smURFP

SEQ ID NO: 36 is the amino acid sequence of the fluorescent protein TDsmURFP.

SEQ ID NO: 37 is the amino acid sequence of the fluorescent protein LanFP2.

SEQ ID NO: 38 is the amino acid sequence of the fluorescent protein HcRed-Tandem.

SEQ ID NO: 39 is the amino acid sequence of the fluorescent protein Skylan-S.

SEQ ID NO: 40 is the amino acid sequence of the fluorescent protein VFP.

SEQ ID NO: 41 is the amino acid sequence of the fluorescent protein GFPxm163.

SEQ ID NO: 42 is the amino acid sequence of the fluorescent protein PlamGFP.

SEQ ID NO: 43 is the amino acid sequence of the fluorescent protein sarcGFP.

SEQ ID NO: 44 is the amino acid sequence of the fluorescent protein psamCFP.

SEQ ID NO: 45 is the amino acid sequence of the fluorescent protein GFPxm18.

SEQ ID NO: 46 is the amino acid sequence of the fluorescent protein Gamillus 0.2.
SEQ ID NO: 47 is the amino acid sequence of the fluorescent protein eGFP.
SEQ ID NO: 48 is the amino acid sequence of the fluorescent protein eYFP.
SEQ ID NO: 49 is the amino acid sequence of the fluorescent protein Venus.
SEQ ID NO: 50 is the amino acid sequence of the fluorescent protein mOrange2.
SEQ ID NO: 51 is the amino acid sequence of the fluorescent protein mCherry.
SEQ ID NO: 52 is the amino acid sequence of the fluorescent protein mTagBFP.
SEQ ID NO: 53 is the amino acid sequence of the fluorescent protein ZsGreen.
SEQ ID NO: 54 is the amino acid sequence of the fluorescent protein YPet.
SEQ ID NO: 55 is the amino acid sequence of the fluorescent protein mCitrine.
SEQ ID NO: 56 is the amino acid sequence of the fluorescent protein CFP.
SEQ ID NO: 57 is the amino acid sequence of the fluorescent protein eCFP.
SEQ ID NO: 58 is the amino acid sequence of the fluorescent protein GFP.
SEQ ID NO: 59 is the amino acid sequence of the fluorescent polypeptide iRFP720.
SEQ ID NO: 60 is the amino acid sequence of the fluorescent polypeptide tdTomato.
SEQ ID NO: 61 is the amino acid sequence of the fluorescent polypeptide sfGFP.

Further preferred fluorescent polypeptides of the present invention include:

22G (Dronpa) from *Echinophyllia* sp. SC22, Genbank ADE48854.1,
aceGFP from *Aequorea coerulescens*, Genbank AAN41637,
amFP486 from *Anemonia majano*, Genbank AAF03371,
anm2CP from Anthoathecata, Genbank AAR85352,
avGFP (classic GFP) from *Aequorea victoria*, Genbank AAA27721,
cFP484 from *Clavularia* sp., Genbank AAF03374,
dendFP from *Dendronephthya* sp., Genbank AAM10625,
dfGFP from *Olindias formosus*, Genbank BBC28143,
DrCBD from *Deinococcus radiodurans*, Genbank AE001825,
DsRed from *Discosoma* sp., Genbank AAF03369,
EosFP from *Lobophyllia hemprichii*, Genbank AAV54099,
eqFP578 from *Entacmaea quadricolor*, Genbank H3JQU7,
eqFP611 from *Entacmaea quadricolor*, Genbank AAN05449,
HcRed from *Heteractis crispa*, Genbank Q95W85.1,
KikG from *Favia favus*, Genbank BAD95670.1,
KO from *Verrillofungia concinna*, Genbank BAD24721,
LanYFP from *Branchiostoma lanceolatum*, Genbank ACA48232,
a sp. #20 from *Montipora* sp. 20 having SEQ ID NO: 4,
mRed7 having SEQ ID NO: 5. mRed7 is a synthetic gene template based on mCherry and multiple other naturally occurring RFPs and chromo proteins. It was the starting template used in the evolution of mScarlet,
pR3784g from *Nostoc punctiforme*, Genbank WP_012410140,
RpBphP1 from *Rhodopseudomonas palustris*, Genbank 5OY5_A,
RpBphP2 from *Rhodopseudomonas palustris*, Genbank WP_011158562,
RpBphP6 from *Rhodopseudomonas palustris*, Genbank WP_011156523,
TeAPCalpha from *Trichodesmium erythraeum* IMS101, Genbank CP000393.1,
zFP538 from *Zoanthus* sp., Genbank AAF03373,
BphP AGP1 from *Agrobacterium tumefaciens*, Genbank F7UC55_RHIRD,
sGPC2 from *Acaryochloris marina* (Chee et al., Journal of Biomedical Optics 23(10), 106006 (October 2018)),
APCF2 from *Chroococcidiopsis thermalis*, Genbank WP_015153831,
UnaG from *Anguilla japonica*, Genbank AB763906.

The fluorescent polypeptides described herein, in particular herein above, can also be found in the following database: https://www.fpbase.org; source code at GibHub: https://github.com/tlambert03/FPbase (Lambert, T J (2019) FPbase: a community-editable fluorescent protein database. Nature Methods. 16, 277-278. doi: 10.1038/s41592-019-0352-8).

DETAILED DESCRIPTION OF THE INVENTION

Figure 1:
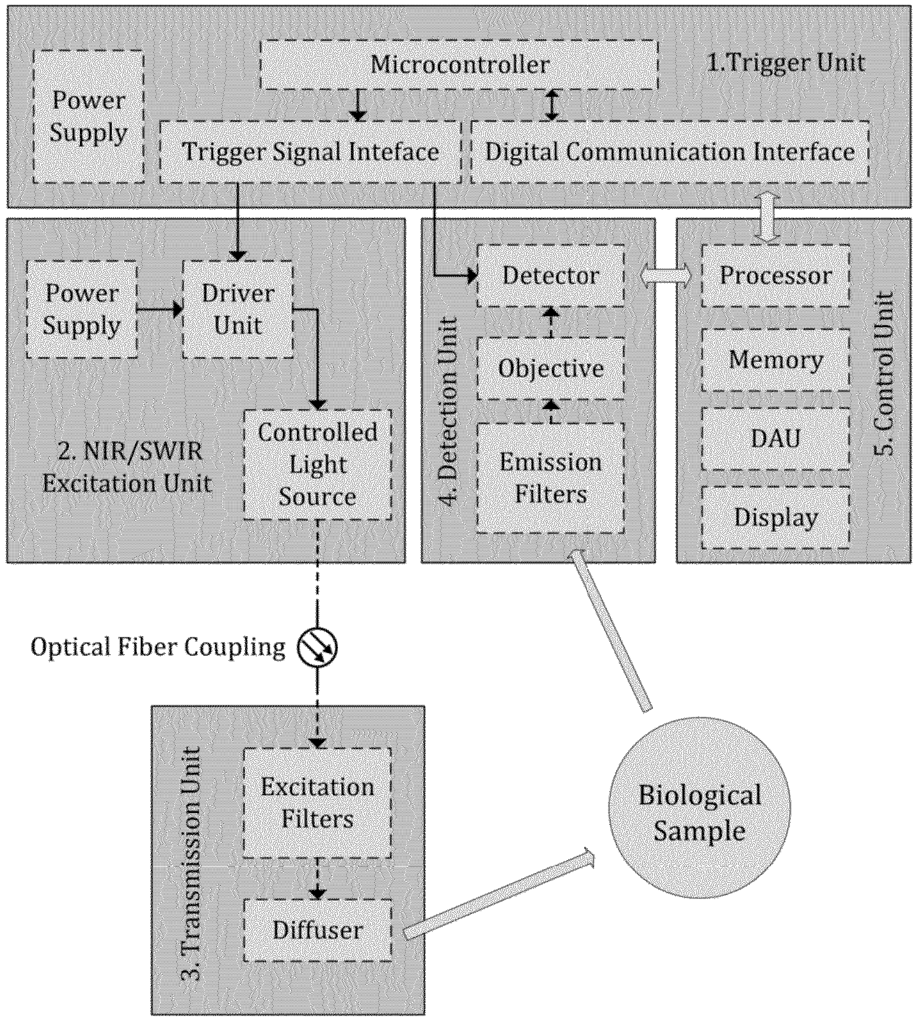
FIG. 1: First exemplary functional diagram of the imaging system of the present invention comprising a trigger unit and triggering algorithm; an excitation unit; a transmission unit and its calibration methodologies; a detection unit and its calibration methodologies; a control unit and algorithm for control and data acquisition; VIS/NIR/SWIR probes (not shown).

The following detailed description refers to the accompanying Examples and Figures that show, by way of illustration, specific details and embodiments, in which the invention may be practiced. These embodiments are described in sufficient detail to enable those skilled in the art to practice the invention. Other embodiments may be utilized such that structural, logical, and eclectic changes may be made without departing from the scope of the invention. Various aspects of the present invention described herein are not necessarily mutually exclusive, as aspects of the present invention can be combined with one or more other aspects to form new embodiments of the present invention.

The present invention solves the challenges faced in the development of real-time multi-color in vivo SWIR imaging systems by employing high-power excitation sources in combination with state of the art InGaAs SWIR detectors and SWIR illuminated fluorophores. The developed system is capable of synchronizing the emission of light sources and SWIR detectors and acquire image data faster than the detectable movements of biological systems (e.g., FIGS. 1 and 2). The sequentially triggered excitation sources illuminate their corresponding fluorophores in the biological sample and detected by synchronized InGaAs detectors to achieve a multi-color SWIR imaging system. The synchronized emitter-detector imaging system also enables high-dynamic range (HDR) imaging and fluid flow-velocimetry mapping of biological structures in SWIR spectrum.

Exploiting a lead structure with bright SWIR emission, flavylium heptamethine dyes with varied substitution at the 7-position of the heterocycle were construed (e.g., as described in WO 2018/226720 A1). The resulting class comprises bright fluorophores with varied excitation wavelengths. The most blue-shifted derivative has a 7-methoxy substituent and absorption at 984 nm, while the most red-shifted derivative, containing a julolidine moiety, absorbs at 1061 nm. These dyes were encapsulated in soft nanomaterials and employed, along with indocyanine green, for excitation-multiplexed imaging in real-time and with high resolution in mice. SWIR multiplexed imaging was enabled to monitor awake mice, hepatic clearance, and orthogonal detection of the lymph and circulatory systems.

On the other hand, by shifting the biological imaging of fluorescent proteins into the near-infrared (e.g., 700-1000 nm) NIR and shortwave-infrared SWIR wavelength (e.g., 1000-2500 nm) regime we can drastically improve the resolution, contrast and penetration depth. Why NIR and SWIR? Near-infrared (NIR) and shortwave-infrared (SWIR) imaging provides higher resolution, penetration depth and sensitivity compared to imaging in the visible range. This makes near-infrared and shortwave-infrared imaging attractive for biological imaging and provides the opportunity to observe complex biological structures. This allows biologists to extract more information from imaging and to answer more/different biological questions.

The lack of labelled biological samples that are optimized for the NIR and SWIR range is perceived as a current boundary for biological imaging in the SWIR. However, this boundary was overcome by the method of the present invention.

The method of the present invention relating to fluorescent protein imaging is based on a counter-intuitive approach allowing imaging of biological samples that are labelled with visible-range emissive fluorescent proteins. As fluorescent proteins possess an extended tail in the emission spectrum, a certain part of the spectrum lies in the NIR and SWIR range, this portion of the emission spectrum is sufficient to do imaging. But so far it has not been described in the literature/state of the art that fluorescent proteins exhibit emission in the NIR (e.g., beyond 850 nm) and SWIR (e.g., beyond 1000 nm). This novel finding in combination with the counter intuitive method of the present invention relating to fluorescent protein imaging now allows to make use of the mentioned advantages of NIR and SWIR imaging using existing fluorescent protein labelled biological samples that are readily available.

Definitions

Unless otherwise specified, the terms used herein have their common general meaning as known in the art.

The term "short wave infrared" used interchangeably with "SWIR" as used herein refers to a portion of the electromagnetic spectrum generally bound between wavelengths of approximately 900 nm and 2500 nm (e.g., preferably in the range 1000-2000 nm). The SWIR light range from 900 nm to 2500 nm is a generally accepted range and is not meant to be definitively limiting in any way.

The term "multiplexed imaging" as used herein refers to an imaging technique in which information (e.g., a signal, e.g., reflected or emitted light) is obtained or acquired simultaneously and/or sequentially and/or synchronically from various different sources (e.g., reflective structures, fluorophores or dyes). In preferred non-limiting embodiments, said multiplexed imaging is an excitation-multiplexed imaging (e.g., excitation-multiplexing enables a single "color-blind" detection source to be used, while excitation sources are modulated) and/or emission-multiplexed imaging (e.g., using multiple detectors with different optical filters to select for different emission bands).

The term "multicolor imaging" as used herein refers to an imaging technique in which information (e.g., a signal, e.g., reflected or emitted light) is obtained or acquired from different sources (e.g., reflective structures, fluorophores or dyes) having different electromagnetic and/or photophysical properties (e.g., colours, i.e., reflected or emitted light properties, wavelengths).

The term "sample location" as used herein refers to any location configured to receive (e.g., sample holder or sample container), comprising or consisting of: any sample suitable for imaging as described herein, e.g., a biological-, non-biological, organic-, non-organic-, naturally occurring- or synthesized sample, or compound, molecule or chemical composition. In preferred non-limiting embodiments, the sample location of the present invention is a biological sample location, which is configured to receive, comprising or consisting of a biological sample.

The term "biological sample" as used herein refers to any living (e.g., in vitro, in vivo or ex vivo) or non-living sample (e.g., post-mortem, frozen or histologically fixed sample, e.g., heat fixed, immersed and/or perfused or chemically fixed, e.g., with an aldehyde, alcohol, oxidizing agent, mercurial, picrate or Hepes-glutamic acid buffer-mediated organic solvent) of at least partial biological origin (e.g., a cell, tissue, organ, whole body, biocomposite, a biomolecule, a composition or mixtures thereof) and includes any biological sample directly or indirectly, fully or partially (e.g., biocomposite) derived from a cell, cell culture, tissue, organ or organism. In preferred non-limiting embodiments, a biological sample of the present invention is e.g., a cell, tissue, cell culture, clinical sample (e.g., a biopsy, bodily fluid, total body water, amniotic fluid, pleural fluid, peritoneal fluid, venipuncture, radial artery puncture, intracellular fluid (ICF), extracellular fluid (ECF), blood, serum, saliva, excreta (e.g., feces or urine), sperm, semen, lymphatic fluid, interstitial fluid, intravascular fluid, transcellular fluid, cerebrospinal fluid (CSF), body tissue, tissue fluid or post-mortem sample), subject (e.g., a mammalian subject, e.g., human), specimen (e.g., a model organism, e.g., a rodent, e.g., *Mus musculus* or *Rattus norvegicus*), biocomposite (e.g., comprising a tissue scaffold and at least a cell) and/or mixture/s thereof, e.g., a cell (e.g., in vivo, ex vivo or in vitro cell), a cell culture, a tissue (in vivo, ex vivo or in vitro tissue), a graft (e.g., an autograft, isograft, allograft or xenograft), an organ, an animal or whole body or a fragment/s or portion/s thereof).

The term "model organism" as used herein refers to any non-human species studied to understand any particular biological phenomena. In preferred non-limiting embodiments, the model organism of the present invention is selected from the group consisting of: a virus (e.g., phage lambda, Phi X 174, SV40, T4 phage, Tobacco mosaic virus, Herpes simplex virus), prokaryote (e.g., *Escherichia coli Bacillus subtilis, Caulobacter crescentus, Mycoplasma genitalium, Aliivibrio fischeri, Synechocystis, Pseudomonas fluorescens, Azotobacter vinelandii, Streptomyces coelicolor*), eukaryote, protist (e.g., *Chlamydomonas reinhardtii, Stentor coeruleus, Dictyostelium discoideum, Tetrahymena thermophila, Emiliania huxleyi, Thalassiosira pseudonana*), fungus (e.g., *Ashbya gossypii, Aspergillus nidulans, Coprinus cinereus, Cryptococcus neoformans, Neurospora crassa, Saccharomyces cerevisiae, Schizophyllum commune, Schizosaccharomyces pombe, Ustilago maydis*), plant (e.g., *Arabidopsis thaliana*), animals, invertebrates (e.g., *Aplysia, Drosophila*, e.g., *Drosophila melanogaster*, Hydra), vertebrate (e.g., *Gallus gallus, Mesocricetus auratus, Cavia porcellus, Medaka* (*Oryzias latipes*, or Japanese ricefish), *Mus musculus, Rattus norvegicus, Xenopus tropicalis* and *Xenopus laevis, Danio rerio*, pigs (e.g., species of genus *Sus*, e.g., *S. scrofa*), sheep (e.g., species of genus *Ovis*, e.g., *O. aries*), dogs (e.g., species of genus *Canis*, e.g., *Canis lupus familiaris*), cats (e.g., species of genus *Felis*, e.g., *F. catus*), rabbits (e.g., species of genera *Sylvilagus* and *Otyctolagus*, e.g., *Sylvilagus floridanus, Otyctolagus cuniculus*), cows (e.g., species of genus *Bos*, e.g., *B. taurus*) and horses (e.g., species of genus *Equus*, e.g., *Equus ferus caballus*). In preferred embodiments cows and/or horses are model organisms in the sense of the present invention, on which the invention could be used for optical guidance during surgery (e.g., pigs, sheep, cows and/or horses are suitable model organisms for optical guidance during surgery).

The term “polypeptide” is equally used herein with the term “protein”. Proteins (including fragments thereof, preferably biologically active fragments, and peptides, usually having less than 30 amino acids) comprise one or more amino acids coupled to each other via a covalent peptide bond (resulting in a chain of amino acids). The term “polypeptide” as used herein describes a group of molecules, which, for example, consist of more than 30 amino acids. Polypeptides may further form multimers such as dimers, trimers and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or hetero-trimers etc. An example for a hetero-multimer is an antibody molecule, which, in its naturally occurring form, consists of two identical light polypeptide chains and two identical heavy polypeptide chains. The terms “polypeptide” and “protein” also refer to naturally modified polypeptides/proteins wherein the modification is affected, e.g., by post-translational modifications like glycosylation, acetylation, phosphorylation and the like. Such modifications are well known in the art.

Fluorescent polypeptides of the present invention are polypeptides which exhibit fluorescence when exposed to appropriate excitation light.

Preferred fluorescent polypeptides are: 22G (Dronpa) from *Echinophyllia* sp. SC22, Genbank ADE48854.1, or a variant thereof having 80% identity to the amino acid sequence deposited in the referenced Genbank entry, wherein said variant shows fluorescence, aceGFP from *Aequorea coerulescens*, Genbank AAN41637, or a variant thereof having 80% identity to the amino acid sequence deposited in the referenced Genbank entry, wherein said variant shows fluorescence, amFP486 from *Anemonia majano*, Genbank AAF03371, or a variant thereof having 80% identity to the amino acid sequence deposited in the referenced Genbank entry, wherein said variant shows fluorescence, anm2CP from Anthoathecata, Genbank AAR85352, or a variant thereof having 80% identity to the amino acid sequence deposited in the referenced Genbank entry, wherein said variant shows fluorescence, avGFP (classic GFP) from *Aequorea victoria*, Genbank AAA27721, or a variant thereof having 80% identity to the amino acid sequence deposited in the referenced Genbank entry, wherein said variant shows fluorescence, cFP484 from *Clavularia* sp., Genbank AAF03374, or a variant thereof having 80% identity to the amino acid sequence deposited in the referenced Genbank entry, wherein said variant shows fluorescence, dendFP from *Dendronephthya* sp., Genbank AAM10625, or a variant thereof having 80% identity to the amino acid sequence deposited in the referenced Genbank entry, wherein said variant shows fluorescence, dfGFP from *Olindias formosus*, Genbank BBC28143, or a variant thereof having 80% identity to the amino acid sequence deposited in the referenced Genbank entry, wherein said variant shows fluorescence, DrCBD from *Deinococcus radiodurans*, Genbank AE001825, or a variant thereof having 80% identity to the amino acid sequence deposited in the referenced Genbank entry, wherein said variant shows fluorescence, DsRed from *Discosoma* sp., Genbank AAF03369, or a variant thereof having 80% identity to the amino acid sequence deposited in the referenced Genbank entry, wherein said variant shows fluorescence, EosFP from *Lobophyllia hemprichii*, Genbank AAV54099, or a variant thereof having 80% identity to the amino acid sequence deposited in the referenced Genbank entry, wherein said variant shows fluorescence, eqFP578 from *Entacmaea quadricolor*, Genbank H3JQU7, or a variant thereof having 80% identity to the amino acid sequence deposited in the referenced Genbank entry, wherein said variant shows fluorescence, eqFP611 from *Entacmaea quadricolor*, Genbank AAN05449, or a variant thereof having 80% identity to the amino acid sequence deposited in the referenced Genbank entry, wherein said variant shows fluorescence, HcRed from *Heteractis crispa*, Genbank Q95W85.1, or a variant thereof having 80% identity to the amino acid sequence deposited in the referenced Genbank entry, wherein said variant shows fluorescence, KikG from *Favia favus*, Genbank BAD95670.1, or a variant thereof having 80% identity to the amino acid sequence deposited in the referenced Genbank entry, wherein said variant shows fluorescence, KO from *Verrillofungia concinna*, Genbank BAD24721, or a variant thereof having 80% identity to the amino acid sequence deposited in the referenced Genbank entry, wherein said variant shows fluorescence, LanYFP from *Branchiostoma lanceolatum*, Genbank ACA48232, or a variant thereof having 80% identity to the amino acid sequence deposited in the referenced Genbank entry, wherein said variant shows fluorescence, a sp. #20 from *Montipora* sp. 20 having the following amino acid sequence (SEQ ID NO: 4), or a variant thereof having 80% identity to the afore-depicted amino acid sequence, wherein said variant shows fluorescence, mRed7 having the following amino acid sequence (SEQ ID NO: 5), or a variant thereof having 80% identity to the afore-depicted amino acid sequence, wherein said variant shows fluorescence, pR3784g from *Nostoc punctiforme*, Genbank WP_012410140, or a variant thereof having 80% identity to the amino acid sequence deposited in the referenced Genbank entry, wherein said variant shows fluorescence, RpBphP1 from *Rhodopseudomonas palustris*, Genbank 5OY5_A, or a variant thereof having 80% identity to the amino acid sequence deposited in the referenced Genbank entry, wherein said variant shows fluorescence, RpBphP2 from *Rhodopseudomonas palustris*, Genbank WP_011158562, or a variant thereof having 80% identity to the amino acid sequence deposited in the referenced Genbank entry, wherein said variant shows fluorescence, RpBphP6 from *Rhodopseudomonas palustris*, Genbank WP_011156523, or a variant thereof having 80% identity to the amino acid sequence deposited in the referenced Genbank entry, wherein said variant shows fluorescence, TeAPCalpha from *Trichodesmium erythraeum* IMS101, Genbank CP000393.1, or a variant thereof having 80% identity to the amino acid sequence deposited in the referenced Genbank entry, wherein said variant shows fluorescence, zFP538 from *Zoanthus* sp., Genbank AAF03373, or a variant thereof having 80% identity to the amino acid sequence deposited in the referenced Genbank entry, wherein said variant shows fluorescence, BphP AGP1 from *Agrobacterium tumefaciens*, Genbank F7UC55_RHIRD, or a variant thereof having 80% identity to the amino acid sequence deposited in the referenced Genbank entry, wherein said variant shows fluorescence, sGPC2 from *Acaryochloris marina* (Chee et al., Journal of Biomedical Optics 23(10), 106006 (October 2018)), or a variant thereof having 80% identity to the amino acid sequence deposited in the referenced Genbank entry, wherein said variant shows fluorescence, APCF2 from *Chroococcidiopsis thermalis*, Genbank WP_015153831, or a variant thereof having 80% identity to the amino acid sequence deposited in the referenced Genbank entry, wherein said variant shows fluorescence, or UnaG from *Anguilla japonica*, Genbank AB763906, or a variant thereof having 80% identity to the amino acid sequence deposited in the referenced Genbank entry, wherein said variant shows fluorescence.

Of the above polypeptides the following ones are preferred: 22G (Dronpa) from *Echinophyllia* sp. SC22, Genbank ADE48854.1, or a variant thereof having 80% identity to the amino acid sequence deposited in the referenced Genbank entry, wherein said variant shows fluorescence, anm2CP from Anthoathecata, Genbank AAR85352, or a variant thereof having 80% identity to the amino acid sequence deposited in the referenced Genbank entry, wherein said variant shows fluorescence, avGFP (classic GFP) from *Aequorea victoria*, Genbank AAA27721, or a variant thereof having 80% identity to the amino acid sequence deposited in the referenced Genbank entry, wherein said variant shows fluorescence, dendFP from *Dendronephthya* sp., Genbank AAM10625, or a variant thereof having 80% identity to the amino acid sequence deposited in the referenced Genbank entry, wherein said variant shows fluorescence, DrCBD from *Deinococcus radiodurans*, Genbank AE001825, or a variant thereof having 80% identity to the amino acid sequence deposited in the referenced Genbank entry, wherein said variant shows fluorescence, DsRed from *Discosoma* sp., Genbank AAF03369, or a variant thereof having 80% identity to the amino acid sequence deposited in the referenced Genbank entry, wherein said variant shows fluorescence, EosFP from *Lobophyllia hemprichii*, Genbank AAV54099, or a variant thereof having 80% identity to the amino acid sequence deposited in the referenced Genbank entry, wherein said variant shows fluorescence, eqFP578 from *Entacmaea quadricolor*, Genbank H3JQU7, or a variant thereof having 80% identity to the amino acid sequence deposited in the referenced Genbank entry, wherein said variant shows fluorescence, eqFP611 from *Entacmaea quadricolor*, Genbank AAN05449, or a variant thereof having 80% identity to the amino acid sequence deposited in the referenced Genbank entry, wherein said variant shows fluorescence, KO from *Verrillofungia concinna*, Genbank BAD24721, or a variant thereof having 80% identity to the amino acid sequence deposited in the referenced Genbank entry, wherein said variant shows fluorescence, a sp. #20 from *Montipora* sp. 20 having the following amino acid sequence (SEQ ID NO: 4), or a variant thereof having 80% identity to the afore-depicted amino acid sequence, mRed7 having the following amino acid sequence (SEQ ID NO: 5), or a variant thereof having 80% identity to the afore-depicted amino acid sequence, RpBphP1 from *Rhodopseudomonas palustris*, Genbank 5OY5_A, or a variant thereof having 80% identity to the amino acid sequence deposited in the referenced Genbank entry, wherein said variant shows fluorescence, RpBphP2 from *Rhodopseudomonas palustris*, Genbank WP_011158562, or a variant thereof having 80% identity to the amino acid sequence deposited in the referenced Genbank entry, wherein said variant shows fluorescence, RpBphP6 from *Rhodopseudomonas palustris*, Genbank WP_011156523, or a variant thereof having 80% identity to the amino acid sequence deposited in the referenced Genbank entry, wherein said variant shows fluorescence, or TeAPCalpha from *Trichodesmium erythraeum* IMS101, Genbank CP000393.1, or a variant thereof having 80% identity to the amino acid sequence deposited in the referenced Genbank entry, wherein said variant shows fluorescence.

Other preferred fluorescent polypeptides in the context of the present invention have a bright emission above 550 nm. These are, for example, RRvT (SEQ ID NO: 6), tdTomato (SEQ ID NO: 7), tdimer2(12) (SEQ ID NO: 8), pcDronpa2 (Red) (SEQ ID NO: 9), mScarlet (SEQ ID NO: 10), mKO kappa (SEQ ID NO: 11), TurboRFP (SEQ ID NO: 12), PSmOrange (Orange) (SEQ ID NO: 13), RFP611 (SEQ ID NO: 14), or mRuby3 (SEQ ID NO: 15).

Other preferred fluorescent polypeptides in the context of the present invention have a bright emission. These are, for example, vsfGFP-0 (SEQ ID NO: 16), LanYFP (SEQ ID NO: 17), bfloGFPa1 (Bomati et al. (2014). Scientific Reports, 4(1), 5469. doi: 10.1038/srep05469), RRvT (SEQ ID NO: 6), dLanYFP (SEQ ID NO: 18), dVFP (SEQ ID NO: 19), ccalYFP1 (SEQ ID NO: 20), efasGFP (SEQ ID NO: 21), pcDronpa (Green) (SEQ ID NO: 22), or aeurGFP (SEQ ID NO: 23).

Other preferred fluorescent polypeptides in the context of the present invention have a pronounced red shifted emission. These are, for example, miRFP720 (SEQ ID NO: 24), iRFP720 (SEQ ID NO: 25), Wi-Phy (SEQ ID NO: 26), SNIFP (SEQ ID NO: 27), iFP2.0 (SEQ ID NO: 28), iRFP713 (SEQ ID NO: 29), iFP1.4 (SEQ ID NO: 30), mIFP (SEQ ID NO: 31), miRFP709 (SEQ ID NO: 32), or miRFP (SEQ ID NO: 33).

Other preferred fluorescent polypeptides in the context of the present invention have a high absorbance. These are, for example, M355NA (SEQ ID NO: 34), vsfGFP-0 (SEQ ID NO: 16), smURFP (SEQ ID NO: 35), TDsmURFP (SEQ ID NO: 36), LanFP2 (SEQ ID NO: 37), HcRed-Tandem (SEQ ID NO: 38), Skylan-S(On) (SEQ ID NO: 39), LanYFP (SEQ ID NO: 17), SNIFP, or aeurGFP (SEQ ID NO: 23).

Other preferred fluorescent polypeptides in the context of the present invention have a pronounced quantum yield. These are, for example, bfloGFPa1 Bomati et al. (2014). Scientific Reports, 4(1), 5469. doi: 10.1038/srep05469), dVFP (SEQ ID NO: 19), VFP (SEQ ID NO: 40), GFPxm163 (SEQ ID NO: 41), PlamGFP (SEQ ID NO: 42), sarcGFP (SEQ ID NO: 43), psamCFP (SEQ ID NO: 44), GFPxm18 (SEQ ID NO: 45), LanYFP (SEQ ID NO: 17), or Gamillus0.2 (SEQ ID NO: 46).

Other preferred fluorescent polypeptides in the context of the present invention are eGFP (SEQ ID NO: 47), eYFP (SEQ ID NO: 48), Venus (SEQ ID NO: 49), mOrange2 (SEQ ID NO: 50), mCherry (SEQ ID NO: 51), mTagBFP (SEQ ID NO: 52), ZsGreen (SEQ ID NO: 53), or Ypet (SEQ ID NO: 54).

Still other preferred fluorescent polypeptides in the context of the present invention are mCitrine (SEQ ID NO: 55), CFP (SEQ ID NO: 56), eCFP (SEQ ID NO: 57), GFP (SEQ ID NO: 58), or eGFP (SEQ ID NO: 47).

The fluorescent polypeptides as described herein, in particular herein above, can also be found in the following database: https://www.fpbase.org; source code at GibHub: https://github.com/tlambert03/FPbase (Lambert, T J (2019) FPbase: a community-editable fluorescent protein database. Nature Methods. 16, 277-278. doi: 10.1038/s41592-019-0352-8).

As used herein, the term "% identity" refers to the percentage of identical amino acid residues at the corresponding position within the sequence when comparing two amino acid sequences with an optimal sequence alignment as exemplified by the ClustalW or X techniques as available from www.clustal.org, or equivalent techniques. Accordingly, both sequences (reference sequence and sequence of interest) are aligned, identical amino acid residues between both sequences are identified and the total number of identical amino acids is divided by the total number of amino acids (amino acid length). The result of this division is a percent value, i.e. percent identity value/degree.

EMBODIMENTS OF THE PRESENT INVENTION

Imaging off-peak in the SWIR window (an embodiment of the present invention): Current in vivo imaging technologies fail to provide high resolution, desirable penetration depths, and sensitivity simultaneously, which limits their widespread adoption for identifying diseases. For example, high resolution and high sensitivity imaging is straightforward on single cells using visible light imaging techniques. However, when imaging whole animals and their tissues, resolution and sensitivity of subsurface tissue features are drastically reduced due to scattering and absorption of light by surrounding tissue. Another major limitation of conventional in vivo imaging technology is the intense background autofluorescence of tissue at the same wavelengths as the emission wavelengths of the fluorescent probes used to detect various conditions. This overlap of autofluorescence with the expected emission wavelengths of the associated fluorescent probes inhibits disease detection. In one such example, traditional imaging with visible and near infrared wavelengths suffers from poor contrast against the background autofluorescence signals from normal cells and tissues (1). System includes a fluorescent probe with a fluorescence peak below 900 nm and at least a portion of a tail of the fluorescence spectrum at a wavelength greater than 900 nm (1). The inventors have recognized the benefits associated with imaging in the short-wave infrared (SWIR) spectral region to avoid the shortcomings of imaging in the visible and near infrared spectrums. Without wishing to be bound by theory, the longer imaging wavelength reduces photon scattering processes, thus maximizing transmission of the imaged light through the tissue within the SWIR spectrum. Thus, imaging in this frequency range results in significantly improved resolution and signal intensity for a given penetration depth. In addition, SWIR radiation exhibits sufficient tissue penetration depths to noninvasively interrogate changes in subsurface tissue features, whereas visible imaging techniques are typically limited to imaging superficial biological structures. For example, in some embodiments, SWIR may permit penetration depths of up to 2 mm or more with a sub 10 micrometer resolution, though instances where SWIR permits larger penetration depths with a different resolution are also contemplated. Further, unlike the visible and near-infrared regions, the SWIR regime contains very little background autofluorescence from healthy tissues, especially in skin and muscle. This reduced autofluorescence signal improves the contrast with the corresponding fluorescence signal from a fluorescent probe and/or autofluorescence from diseased tissue enabling easier distinction between pathological and non-pathological biological structures. The reduced light scattering, enhanced light transmission, and suppressed background autofluorescence all combine to enable imaging and detection methods with increased contrast, resolution, and sensitivity as compared to more typical imaging methods (1). Fluorescent probes are typically excited in the Visible/Near-Infrared range (e.g., 400-1100 nm), those probes could include fluorescent dyes, quantum dots and carbon nanotubes. The emission spectrum lies as well in the visible/near-infrared range. However, a part of the spectrum is detectable in the short-wave infrared (e.g., 900 nm-2500 nm). This allows the use of the advantages of detection in the short wave. Advantages includes the increased contrast; this contrast comes from the absorption features of water in the infrared regime. Those absorption features at different wavelength bands can be used to extract depth information from images and hence to extract 3D information from the 2D images (2).

Exemplary non-limiting detection (an embodiment of the present invention): Imaging in this wavelength regime has been limited by the detector technologies, still the price of SWIR cameras is high. Available detectors include InGaAs detectors (e.g., 900-1700 nm), HgCdTe or MCT detectors (e.g., 700-2500 nm), Germanium, bolometers, superconducting nanowires, pyroelectric detectors etc. The cameras are cooled and have a certain level of read noise (noise of the electronics of camera, level is much higher compared to conventional silicon based CMOS detectors) and dark current/dark noise (noise from detecting photons (or generating charges) not originating from the imaged object but rather the camera system itself), to achieve images with controllable noise levels one has to keep the exposure time minimal, this allows to stay in the noise regime where only the read noise the camera but not the dark current/dark noise influences the detection. By exposing longer, one enters a higher noise level, where the dark current (temperature dependent noise) kicks in. This leads to noisier pictures. Hence, controlling the laser/LED/light source and the camera together allows to keep the noise level minimal. By triggering the laser/LED/light source and sending pulses of excitation light and coupling the detection one achieves better outcome. To have a rather high capture of the emitted light of the probe one needs optimized optics. The lenses are coated for the infrared regime (C-Coating by Thorlabs, e.g., 1050-1700 nm) in order to prevent unwanted reflections from the surfaces. To filter out the excitation light and the emitted light in the visible regime, one adds filters on the detection path. An example would be a 1000 nm or a 1100 nm Long Pass filter, only permitting light of wavelengths above 1000 nm to pass.

Exemplary non-limiting technical specification (an embodiment of the present invention): Exemplary non-limiting functional description (e.g., FIG. 2): Given a biological sample embedded with targeted SWIR probes, the imaging system can be accessed and controlled to attain a real-time multi-color SWIR fluorescence image data via a desktop PC based control station. Probe-specific optimized excitation and emission filters are integrated with the system to achieve high optical sensitivity of target structures. Users may programmatically access the microcontroller of the trigger unit and the detector firmware via control unit. Subsequently, the trigger sequence is uploaded to the trigger unit and detector parameters are assigned to the detector unit. The trigger sequence algorithm then initiates and controls the synchronization of VIS/NIR/SWIR excitation unit and detector unit to achieve real-time multi-color SWIR fluorescence image acquisition. The microcontroller trigger signal interface transmits the electrical signals to the excitation driver unit and produces desired optical signals of excitation. The optical excitation signals enter the biological samples infused with SWIR probes and returns as autofluorescence and fluorescence optical emission signals. The fluorescence optical emission signals are collected using a detector unit and may filtered from the associated autofluorescence signals and other obstructive signals of interference. The detector unit then performs image acquisition of VIS/NIR/SWIR excited biological structures using multiple pixel detector array (e.g., a camera chip). By chemically engineering high intensity fluorescence signals from the targeted infrared probes, the exposure time required for the pixel data acquisition is minimized and high frame-rate acquisition is enabled. Consequently, a fast frame-rate acquisition detector device is employed to enable image acquisition. A temporally separated and fast switched excitation source with multiple electromagnetic excitation wavelengths and low-transient is electronically controlled to achieve simultaneous switching of detector device and excitation wavelengths of interest. Thus, a high through-put multi-spectrum pixel image dataset is generated in the short-wave infrared electromagnetic spectrum (e.g., 900 nm-2500 nm). This image data is displayed during the signal acquisition and stored in the control unit. The acquired multi-spectrum image dataset is then processed in the control unit to produce multicolor real-time image data that is analogues to the SWIR electromagnetic spectrum.

Exemplary non-limiting system architecture (an embodiment of the present invention): As shown in the FIG. 2, the functional imaging system comprises a control unit, a trigger unit, an excitation unit, a transmission unit, a detection unit and a safety enclosure. The technical features and functions of the individual system components are detailed as follows.

Figure 3:
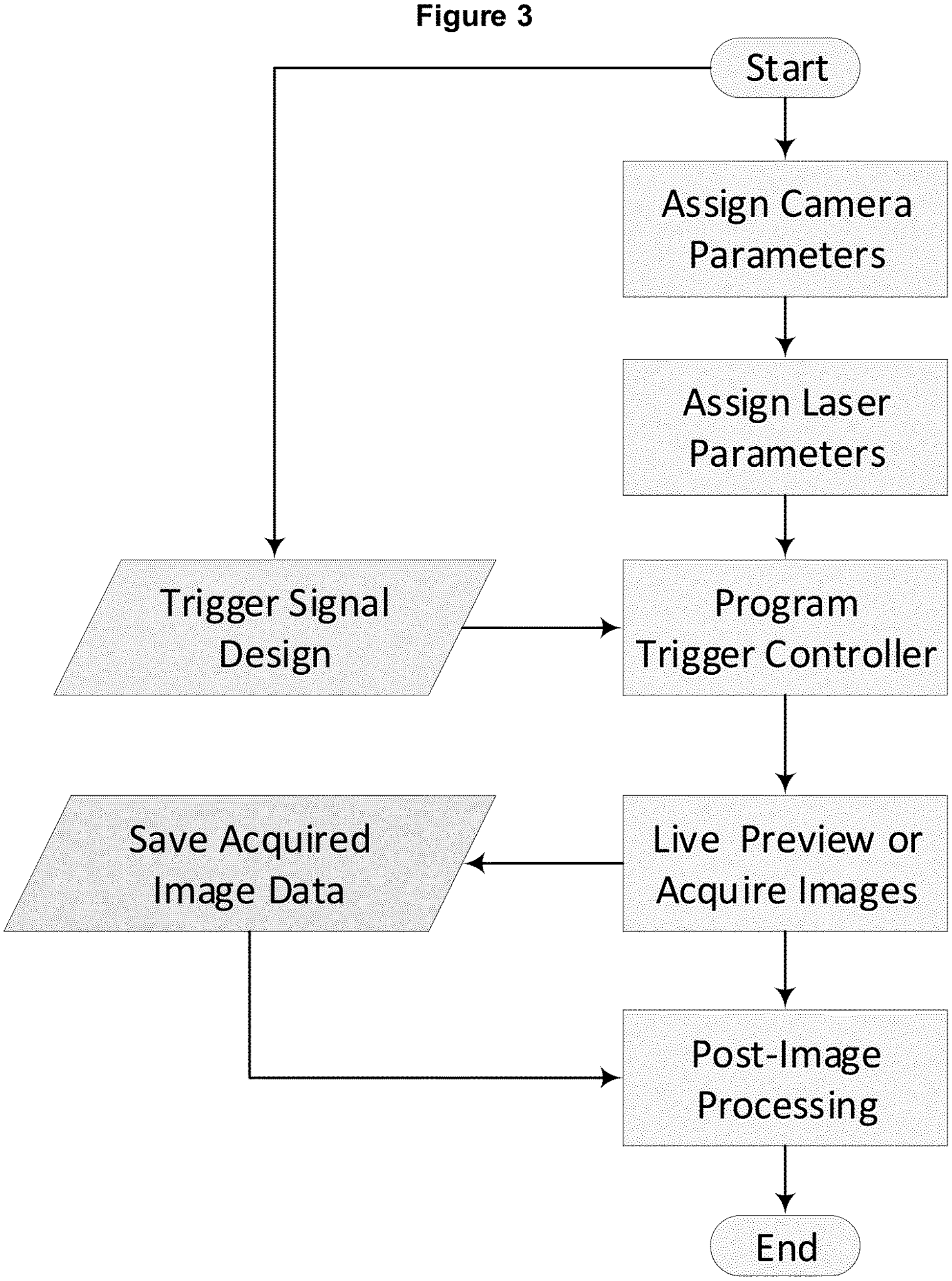
FIG. 3: Flowchart for generalized image acquisition algorithm in control unit.

Exemplary non-limiting control unit (an embodiment of the present invention): The control unit enables the system users to electronically access and control other functional components of the system. The control unit may consist of a data acquisition unit (DAU), electronic processors (Processor), electronic memory unit (Memory), electronic input-output modules (I/O), display units (Display). The sub-system components of the control unit work together to execute the application specific machine instructions. The general description of application specific algorithm is presented in FIG. 3 herein. As observed the sequential execution of this flowchart is carried-out by automatic or manual means in the control unit. The implemented algorithm in FIG. 3 features a sequential time-driven implementation strategy to achieve high-throughput multicolor imaging system. An alternative imaging system development is to use a model-based event-driven strategy to realize the same outcome. In the model-based event-driven algorithm, the experiment or application specific trigger signal is modelled and simulated prior to the execution in the microcontroller. Further, the feedback information from the event-driven closed-loop control structure would eliminate the inter-delays during the system operation. The DAU is a digital device that employs a high-bandwidth data path using digital communication protocols between the detector unit and the memory of the control unit. It facilitates the high through-put transfer of acquired image data with low latency to the control unit for subsequent image processing. As such a DAU can be any semiconductor-based device that includes its own sub-system components such as digital processors, controllers, field-programmable transistor circuitries and its own set of machine instructions and communication protocols. The processor unit may be implemented as integrated circuits, with multiple processors in an integrated circuit component, including commercially available integrated circuit components such as CPU chips, GPU chips, microprocessors, co-processors or an ASIC, or semicustom circuitry from a programmable logic device (1). The components of the control unit can be a single computing device embodied in variety of forms. This may include rack-mounted computer, a desktop computer, a laptop computer, a tablet computer, a smart phone, a personal digital assistant or any other suitable portable or fixed electronic device (1). In this aspect, a computing device may have one or more input and output devices (I/O) that may be used to present a user interface and interconnected by one or more networks in any suitable form, including as a local area network or a wide area network, such as an enterprise network or the Internet (1). The various implementation methods or processes for the design of the control unit may be coded as software components that is executable on one or more processors and can be written in suitable programming languages and/or programming or scripting tools, and also may be compiled as executable machine language code or intermediate code that is executed on a framework or virtual machine (1). Additionally, the control unit can also be integrated with internet of things (IoT) devices and cloud-based computing algorithms for the remote operation of the imaging system. As such, the control unit can also be a virtual machine interface that enables user interaction with the other components of the imaging system.

Figure 4A:
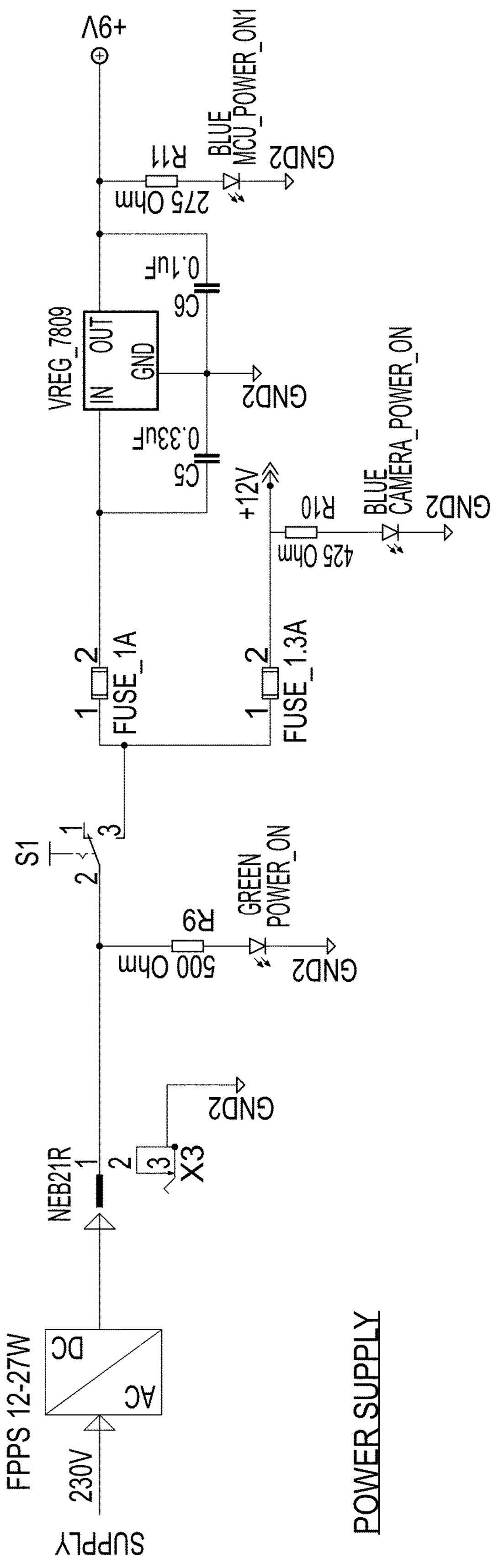
FIG. 4: Exemplary schematic of microcontroller-based trigger unit implementation.
Figure 4B:
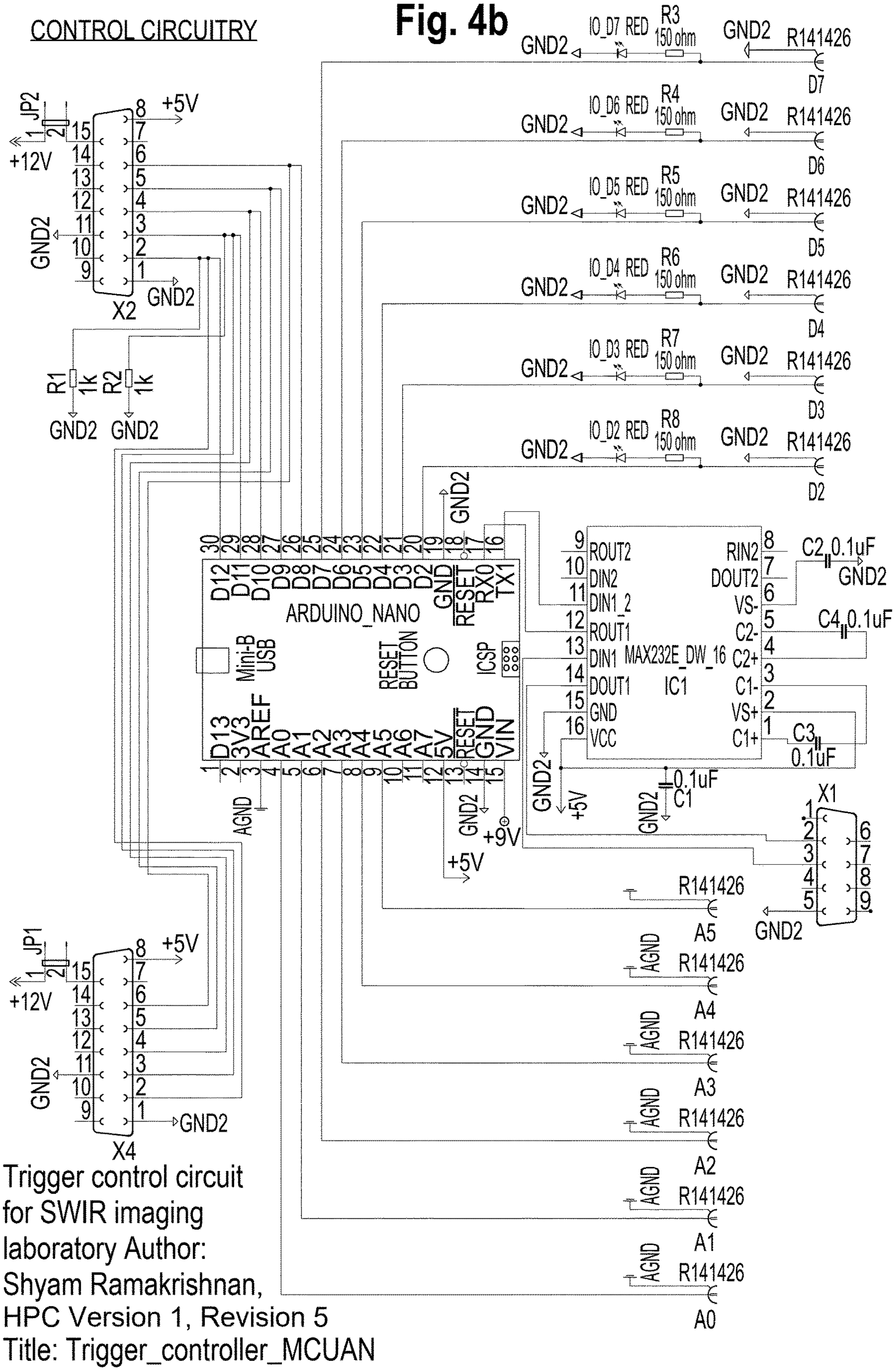

Exemplary non-limiting trigger unit (an embodiment of the present invention): The trigger unit receives user instructions from control unit for high-speed switching control of detection unit and excitation unit by generating electrical signals of interest. It consists of a microcontroller, trigger signal interface, communication interface and a power supply unit. An example implementation of a microcontroller-based trigger unit is illustrated in FIG. 4 herein by means of an electrical schematic diagram. The application specific control instructions can be designed in the control unit and programmed in the trigger unit microcontroller via the communication interface. The dedicated power supply for the trigger controller enables the stand-alone operation of the trigger unit independent of the control unit. Therefore, with appropriately programmed microcontroller, the trigger unit retains the control of excitation and detection units and facilitates the sequential transduce of electrical-optical-electrical signals. The utilized microcontroller unit is a 32 bit, 16 MHz off-the shelf microcontroller board. It features 32 KB (2 KB reserved for the bootloader) of flash memory, 1 KB of EEPROM and a SRAM of 2 KB. It features 22 digital I/O pins (of which 11 pins are effectively used in the trigger unit)

and 6 Analog input pins. The operating voltage of the microcontroller is 5V and each digital pins require 40 mA of DC current. The high frequency operation of the microcontroller yields a delay and transient free operation of the trigger unit in the time resolutions low as ~1 ms. The microcontroller unit can be any semiconductor based electronic sub-system that may facilitate analog and digital signal processing, programming and data memory, digital and analog input-output periphery, crystal oscillators for clock signal generation, analog to digital conversion units (ADU), digital to analog conversion units (DAU) and communication interfaces. The microcontroller unit may share the features and functions of the processor subsystem of the control unit but shall be completely independent of the control unit. As such, independent control units can also be employed to access and configure the trigger unit and the detector units to constitute a functional system architecture in contrast to the system proposed in (1). The trigger signal interface constitutes electric signal coupling between the microcontroller unit and external peripheries such as excitation and detector control systems. Depending on the system design strategy the excitation and detector control systems can be designed as independent sub-systems or embedded sub-systems in the trigger unit. The signal interface can consist of electrical cabling or wireless electrical communication devices. The trigger signal interface facilitates bi-directional flow of signals to and from the devices or sub-systems of interest. The communication interface facilitates the access of trigger unit from a control unit. It informs the status of the connected sub-system components to the control unit and enables the user-access to the programmable microcontroller sub-system. The power supply subsystem of the control unit is designed to supply the operational power requirements of the trigger unit and upon requirement the detector unit.

Exemplary non-limiting excitation unit (an embodiment of the present invention): The excitation unit transduces the electrical signals to the VIS/NIR/SWIR optical signals in single spectrum or in multiple spectra. It consists of a controlled light source, a driver unit and a power supply. Any appropriate excitation source may be used including, but not limited to, a diode laser, light emitting diode, or any other appropriate source of electromagnetic radiation within a desired spectral band (1). The excitation sources are optically coupled to the transmission unit via an appropriate optical coupling such as optical fiber bundles, a light pipe, a planar light guide or an optically clear space (1). The driver unit sub-system of the excitation unit converts the incoming voltage-coded electrical signals into desired power levels of the excitation source. Doing so, it extracts electrical power from the power supply sub-system of the excitation unit and controls the optical power of the excitation source. Depending on the application requirement, the driver unit may provide a constant power output, an external digital modulated power output, an external analog modulated power output or an internal digital modulated power output. In case of external digital modulated power output mode, the switching states of the excitation source is controlled by the electrical signals generated by the trigger unit. Thus, generating the optical signals of interest following the received electrical signals. Depending on the application requirements one or more light sources of varying spectrum can be employed to achieve multicolor image acquisition.

Exemplary non-limiting transmission unit (an embodiment of the present invention): The transmission unit optically couples the excitation unit and the safety enclosure where the biological sample is being placed. It consists of optical coupling mechanism, excitation filters and a diffuser. The optical coupling routes the electromagnetic radiation from the excitation source to excitation filters (1). Fora given application, a desired set of excitation wavelengths can be optically transmitted to the biological samples consisting of SWIR probes. The excitation filters are a combination of low and/or high and/or bandpass and/or laser-line filters to provide electromagnetic radiations of predetermined electromagnetic spectra. The filters may exclude electromagnetic wavelengths above and/or below a desired fluorescence spectrum wavelength or other undesirable excitation wavelengths (1). The transmitted electromagnetic radiation may then pass through an engineered diffuser to evenly spread the excitation light across the biological sample of interest. Depending on the application needs, the transmission unit can be designed individually for each excitation source or designed as a single unit for all excitation sources of varying electromagnetic spectra.

Figure 5:
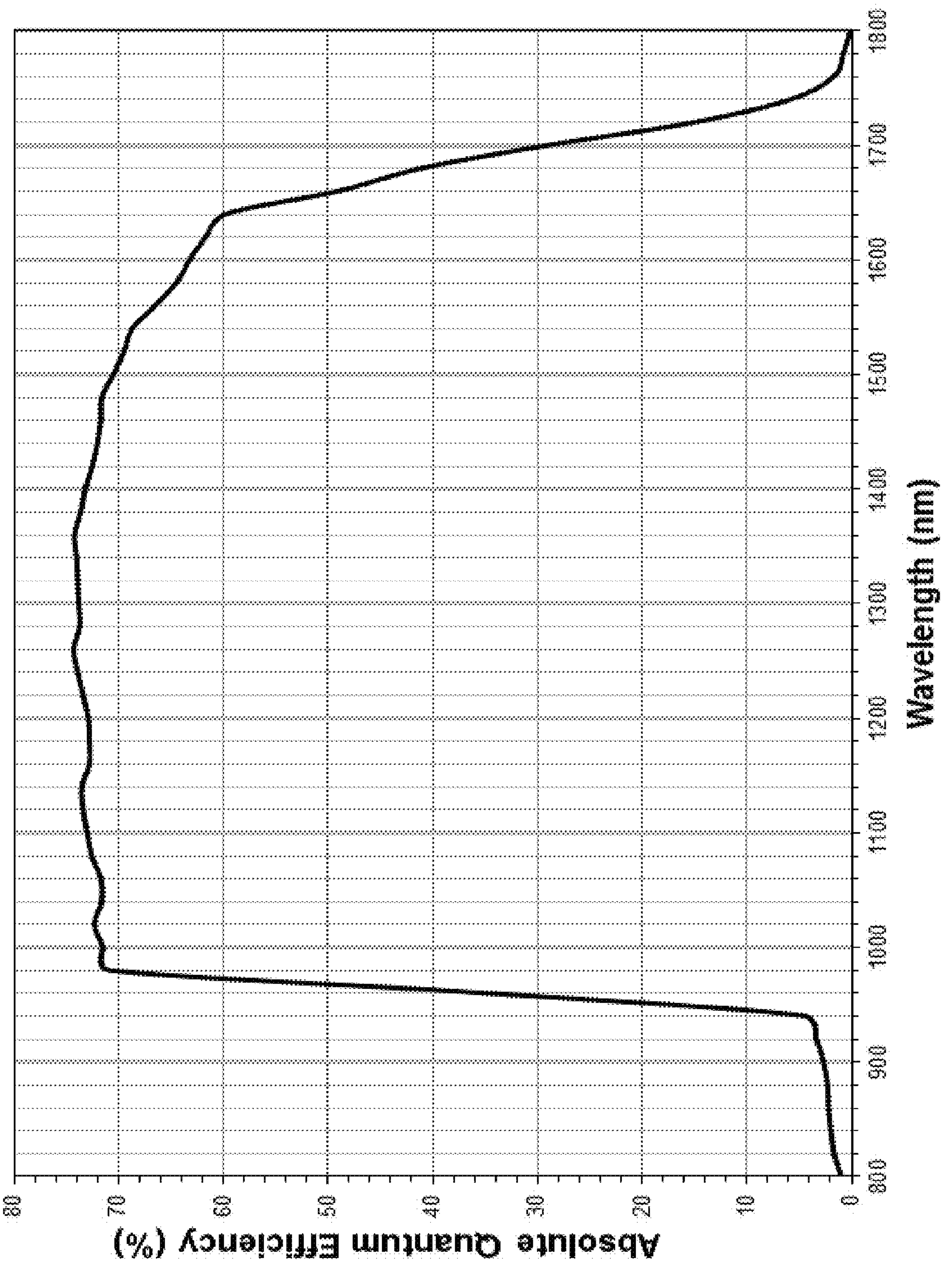
FIG. 5: Absolute Quantum Efficiency of Goldeye G032 Cool Camera (derived from the camera datasheet).

Exemplary non-limiting detection unit (an embodiment of the present invention): The detection unit partly collects the optical signals generated by the SWIR fluorescent probe within the biological sample and transduces them into electrical signals. It consists of a detector, emission filters and an objective. The detector is made of plurality of pixels and with appropriately configured and arranged objective, it collects optical signals from the emitting electromagnetic radiations of SWIR fluorophores (1). The detector may be sensitive to any appropriate range of electromagnetic wavelengths including the short-wave infrared spectral range (1). In addition, the used detector shall facilitate high frequency image acquisition to facilitate multicolor real-time imaging. The detector shall also accompany an input-output interface to facilitate external control with voltage-coded electrical signals. One or more filters may be placed in between the detector and biological sample with SWIR fluoresces to reject reflected excitation light and other optical interferences that may impair the acquisition of signals of interest (1). The detector used in the system is an Allied Vision Goldeye G032 Cool camera. The technical specifications for the camera are shown in the Table 1 and its quantum efficiency is reported in FIG. 5.

TABLE 1

Camera Specifications for Goldeye G032 cool.

| | |
|---|---|
| Sensor Type | InGaAs FPA |
| Pixel size | 25 μm × 25 μm |
| Resolution | 636 (H) × 508 (V) |
| ADC | 14 Bit |
| Max. frame rate at full resolution | 100 fps |
| Temporal dark noise | 400 $e^-$ (Gain0), 170 $e^-$ (Gain1) |
| Saturation capacity | 1.9 $Me^-$ (Gain0), 39 $ke^-$ (Gain1) |
| Dynamic range | 73 dB (Gain0), 47 dB (Gain1) |

Upon detecting a fluorescent signals and/or auto-fluorescent signals, the detector may output the analogous electrical signals to a processor subsystem of the control unit. The processor may then appropriately process the information as stated earlier to determine whether the detected signal corresponds to a targeted biological structure and/or state (1). This information may be determined for each pixel either for a single captured image and/or continuously in real time and may be displayed as an image on a display and/or stored within a memory of the control unit. By multiplexing different biological targets with variety of SWIR fluorophores, the processing unit can be used to isolate and render multicolor real-time image information.

Exemplary non-limiting safety enclosure (an embodiment of the present invention): The safety enclosure of the system reiterates the safety of the user whilst blocking optical interference to the detector unit. It may be designed as a physical component matching the dimension of the imaging system with materials that block optical signals. An enclosure may also facilitate the mounting mechanisms to hold the system and sub-system components of the imaging system.

Exemplary non-limiting system specification (an embodiment of the present invention).

TABLE 2

| Exemplary non-limiting system specification | |
|---|---|
| Detection Range | 1000-1600 nm |
| Absolute Quantum Efficiency | Up to 70% |
| Detection Resolution | 636 (H) × 508 (V) |
| Detection Speed | 100 FPS (can be extended to 300 FPS with Goldeye CL 033 Camera) |
| Excitation | Up to 25 W optical illumination in the wavelengths of 785 nm, 892 nm, 980 nm, 1062 nm |
| Triger-time resolution | 1 ms |
| Trigger-time delay | Less than 10 uS |
| Image Color Rendering | 4 Color (Can be extended to 5 and more colors) |
| No. of Detector Control Ports | 2 |
| No. of Excitation Control Ports | 6 |
| No. of Analog Input Ports | 6 |
| Optical System | Adaptable and reconfigurable SWIR optical system |

Exemplary Non-Limiting Fluorescent Polypeptides of the Present Invention

Fluorescent polypeptides applied in the context of the present invention, e.g. in the systems and methods described herein are in general proteins which exhibit fluorescence when exposed to appropriate excitation light.

Particularly preferred fluorescent polypeptides of the present invention include: SEQ ID NO: 1, SEQ ID NO: 2 and SEQ ID NO: 3.

Further preferred fluorescent polypeptides of the present invention include: 22G (Dronpa) from *Echinophyllia* sp. SC22, Genbank ADE48854.1, or a variant thereof having 80% identity to the amino acid sequence deposited in the referenced Genbank entry, wherein said variant shows fluorescence, aceGFP from *Aequorea coerulescens*, Genbank AAN41637, or a variant thereof having 80% identity to the amino acid sequence deposited in the referenced Genbank entry, wherein said variant shows fluorescence, amFP486 from *Anemonia majano*, Genbank AAF03371, or a variant thereof having 80% identity to the amino acid sequence deposited in the referenced Genbank entry, wherein said variant shows fluorescence, anm2CP from Anthoathecata, Genbank AAR85352, or a variant thereof having 80% identity to the amino acid sequence deposited in the referenced Genbank entry, wherein said variant shows fluorescence, avGFP (classic GFP) from *Aequorea victoria*, Genbank AAA27721, or a variant thereof having 80% identity to the amino acid sequence deposited in the referenced Genbank entry, wherein said variant shows fluorescence, cFP484 from *Clavularia* sp., Genbank AAF03374, or a variant thereof having 80% identity to the amino acid sequence deposited in the referenced Genbank entry, wherein said variant shows fluorescence, dendFP from *Dendronephthya* sp., Genbank AAM10625, or a variant thereof having 80% identity to the amino acid sequence deposited in the referenced Genbank entry, wherein said variant shows fluorescence, dfGFP from *Olindias formosus*, Genbank BBC28143, or a variant thereof having 80% identity to the amino acid sequence deposited in the referenced Genbank entry, wherein said variant shows fluorescence, DrCBD from *Deinococcus radiodurans*, Genbank AE001825, or a variant thereof having 80% identity to the amino acid sequence deposited in the referenced Genbank entry, wherein said variant shows fluorescence, DsRed from *Discosoma* sp., Genbank AAF03369, or a variant thereof having 80% identity to the amino acid sequence deposited in the referenced Genbank entry, wherein said variant shows fluorescence, EosFP from *Lobophyllia hemprichii*, Genbank AAV54099, or a variant thereof having 80% identity to the amino acid sequence deposited in the referenced Genbank entry, wherein said variant shows fluorescence, eqFP578 from *Entacmaea quadricolor*, Genbank H3JQU7, or a variant thereof having 80% identity to the amino acid sequence deposited in the referenced Genbank entry, wherein said variant shows fluorescence, eqFP611 from *Entacmaea quadricolor*, Genbank AAN05449, or a variant thereof having 80% identity to the amino acid sequence deposited in the referenced Genbank entry, wherein said variant shows fluorescence, HcRed from *Heteractis crispa*, Genbank Q95W85.1, or a variant thereof having 80% identity to the amino acid sequence deposited in the referenced Genbank entry, wherein said variant shows fluorescence, KikG from *Favia favus*, Genbank BAD95670.1, or a variant thereof having 80% identity to the amino acid sequence deposited in the referenced Genbank entry, wherein said variant shows fluorescence, KO from *Verrillofungia concinna*, Genbank BAD24721, or a variant thereof having 80% identity to the amino acid sequence deposited in the referenced Genbank entry, wherein said variant shows fluorescence, LanYFP from *Branchiostoma lanceolatum*, Genbank ACA48232, or a variant thereof having 80% identity to the amino acid sequence deposited in the referenced Genbank entry, wherein said variant shows fluorescence, a sp. #20 from *Montipora* sp. 20 having the following amino acid sequence (SEQ ID NO: 4), or a variant thereof having 80% identity to the afore-depicted amino acid sequence, wherein said variant shows fluorescence, mRed7 having the following amino acid sequence (SEQ ID NO: 5), or a variant thereof having 80% identity to the afore-depicted amino acid sequence, wherein said variant shows fluorescence, pR3784g from *Nostoc punctiforme*, Genbank WP_012410140, or a variant thereof having 80% identity to the amino acid sequence deposited in the referenced Genbank entry, wherein said variant shows fluorescence, RpBphP1 from *Rhodopseudomonas palustris*, Genbank 5OY5_A, or a variant thereof having 80% identity to the amino acid sequence deposited in the referenced Genbank entry, wherein said variant shows fluorescence, RpBphP2 from *Rhodopseudomonas palustris*, Genbank WP_011158562, or a variant thereof having 80% identity to the amino acid sequence deposited in the referenced Genbank entry, wherein said variant shows fluorescence, RpBphP6 from *Rhodopseudomonas palustris*, Genbank WP_011156523, or a variant thereof having 80% identity to the amino acid sequence deposited in the referenced Genbank entry, wherein said variant shows fluorescence, TeAPCalpha from *Trichodesmium erythraeum* IMS101, Genbank CP000393.1, or a variant thereof having 80% identity to the amino acid sequence deposited in the referenced Genbank entry, wherein said variant shows fluorescence, zFP538 from

*Zoanthus* sp., Genbank AAF03373, or a variant thereof having 80% identity to the amino acid sequence deposited in the referenced Genbank entry, wherein said variant shows fluorescence, BphP AGP1 from *Agrobacterium tumefaciens*, Genbank F7UC55 RHIRD, or a variant thereof having 80% identity to the amino acid sequence deposited in the referenced Genbank entry, wherein said variant shows fluorescence, sGPC2 from *Acaryochloris marina* (Chee et al., Journal of Biomedical Optics 23(10), 106006 (October 2018)), or a variant thereof having 80% identity to the amino acid sequence deposited in the referenced Genbank entry, wherein said variant shows fluorescence, APCF2 from *Chroococcidiopsis thermalis*, Genbank WP_015153831, or a variant thereof having 80% identity to the amino acid sequence deposited in the referenced Genbank entry, wherein said variant shows fluorescence, or UnaG from *Anguilla japonica*, Genbank AB763906, or a variant thereof having 80% identity to the amino acid sequence deposited in the referenced Genbank entry, wherein said variant shows fluorescence.

Of the above polypeptides the following ones are preferred: 22G (Dronpa) from *Echinophyllia* sp. SC22, Genbank ADE48854.1, or a variant thereof having 80% identity to the amino acid sequence deposited in the referenced Genbank entry, wherein said variant shows fluorescence, anm2CP from Anthoathecata, Genbank AAR85352, or a variant thereof having 80% identity to the amino acid sequence deposited in the referenced Genbank entry, wherein said variant shows fluorescence, avGFP (classic GFP) from *Aequorea victoria*, Genbank AAA27721, or a variant thereof having 80% identity to the amino acid sequence deposited in the referenced Genbank entry, wherein said variant shows fluorescence, dendFP from *Dendronephthya* sp., Genbank AAM10625, or a variant thereof having 80% identity to the amino acid sequence deposited in the referenced Genbank entry, wherein said variant shows fluorescence, DrCBD from *Deinococcus radiodurans*, Genbank AE001825, or a variant thereof having 80% identity to the amino acid sequence deposited in the referenced Genbank entry, wherein said variant shows fluorescence, DsRed from *Discosoma* sp., Genbank AAF03369, or a variant thereof having 80% identity to the amino acid sequence deposited in the referenced Genbank entry, wherein said variant shows fluorescence, EosFP from *Lobophyllia hemprichii*, Genbank AAV54099, or a variant thereof having 80% identity to the amino acid sequence deposited in the referenced Genbank entry, wherein said variant shows fluorescence, eqFP578 from *Entacmaea quadricolor*, Genbank H3JQU7, or a variant thereof having 80% identity to the amino acid sequence deposited in the referenced Genbank entry, wherein said variant shows fluorescence, eqFP611 from *Entacmaea quadricolor*, Genbank AAN05449, or a variant thereof having 80% identity to the amino acid sequence deposited in the referenced Genbank entry, wherein said variant shows fluorescence, KO from *Verrillofungia concinna, Genbank BAD*24721, or a variant thereof having 80% identity to the amino acid sequence deposited in the referenced Genbank entry, wherein said variant shows fluorescence, a sp. #20 from *Montipora* sp. 20 having the following amino acid sequence (SEQ ID NO: 4), or a variant thereof having 80% identity to the afore-depicted amino acid sequence, mRed7 having the following amino acid sequence (SEQ ID NO: 5), or a variant thereof having 80% identity to the afore-depicted amino acid sequence, RpBphP1 from *Rhodopseudomonas palustris*, Genbank 5OY5_A, or a variant thereof having 80% identity to the amino acid sequence deposited in the referenced Genbank entry, wherein said variant shows fluorescence, RpBphP2 from *Rhodopseudomonas palustris*, Genbank WP_011158562, or a variant thereof having 80% identity to the amino acid sequence deposited in the referenced Genbank entry, wherein said variant shows fluorescence, RpBphP6 from *Rhodopseudomonas palustris*, Genbank WP_011156523, or a variant thereof having 80% identity to the amino acid sequence deposited in the referenced Genbank entry, wherein said variant shows fluorescence, or TeAPCalpha from *Trichodesmium erythraeum* IMS101, Genbank CP000393.1, or a variant thereof having 80% identity to the amino acid sequence deposited in the referenced Genbank entry, wherein said variant shows fluorescence.

Other preferred fluorescent polypeptides in the context of the present invention have a bright emission above 550 nm. These are, for example, RRvT, tdTomato, tdimer2(12), pcDronpa2 (Red), mScarlet, mKOK, TurboRFP, PSmOrange (Orange), RFP611, or mRuby3. These preferred fluorescent polypeptides.

Other preferred fluorescent polypeptides in the context of the present invention have a bright emission. These are, for example, vsfGFP-0, LanYFP, bfloGFPa1, RRvT, dLanYFP, dVFP, ccalYFP1, efasGFP, pcDronpa (Green), or aeurGFP.

Other preferred fluorescent polypeptides in the context of the present invention have a pronounced red shifted emission. These are, for example, miRFP720, iRFP720, Wi-Phy, SNIFP, iFP2.0, iRFP713, iFP1.4, mIFP, miRFP709, or miRFP.

Other preferred fluorescent polypeptides in the context of the present invention have a high absorbance. These are, for example, M355NA, vsfGFP-0, smURFP, TDsmURFP, LanFP2, HcRed-Tandem, Skylan-S(On), LanYFP, SNIFP, or aeurGFP.

Other preferred fluorescent polypeptides in the context of the present invention have a pronounced quantum yield. These are, for example, bfloGFPa1, dVFP, VFP, GFPxm163, PlamGFP, sarcGFP, psamCFP, GFPxm18, LanYFP, or Gamillus0.2.

Other preferred fluorescent polypeptides in the context of the present invention are eGFP, eYFP, Venus, mOrange2, mCherry, mTagBFP, ZsGreen, or Ypet.

Still other preferred fluorescent polypeptides in the context of the present invention are mCitrine, CFP, eCFP, GFP, or eGFP.

The fluorescent polypeptides described herein, in particular herein above, can also be found in the following database: https://www.fpbase.org; source code at GibHub: https://github.com/tlambert03/FPbase (Lambert, T J (2019) FPbase: a community-editable fluorescent protein database. Nature Methods. 16, 277-278. doi: 10.1038/s41592-019-0352-8).

In some aspects, the system of the present invention has the specification and/or functionality as described in Table 2.

In some aspects, the system of the present invention has the specification and/or functionality as described in FIG. 1.

Figure 2:
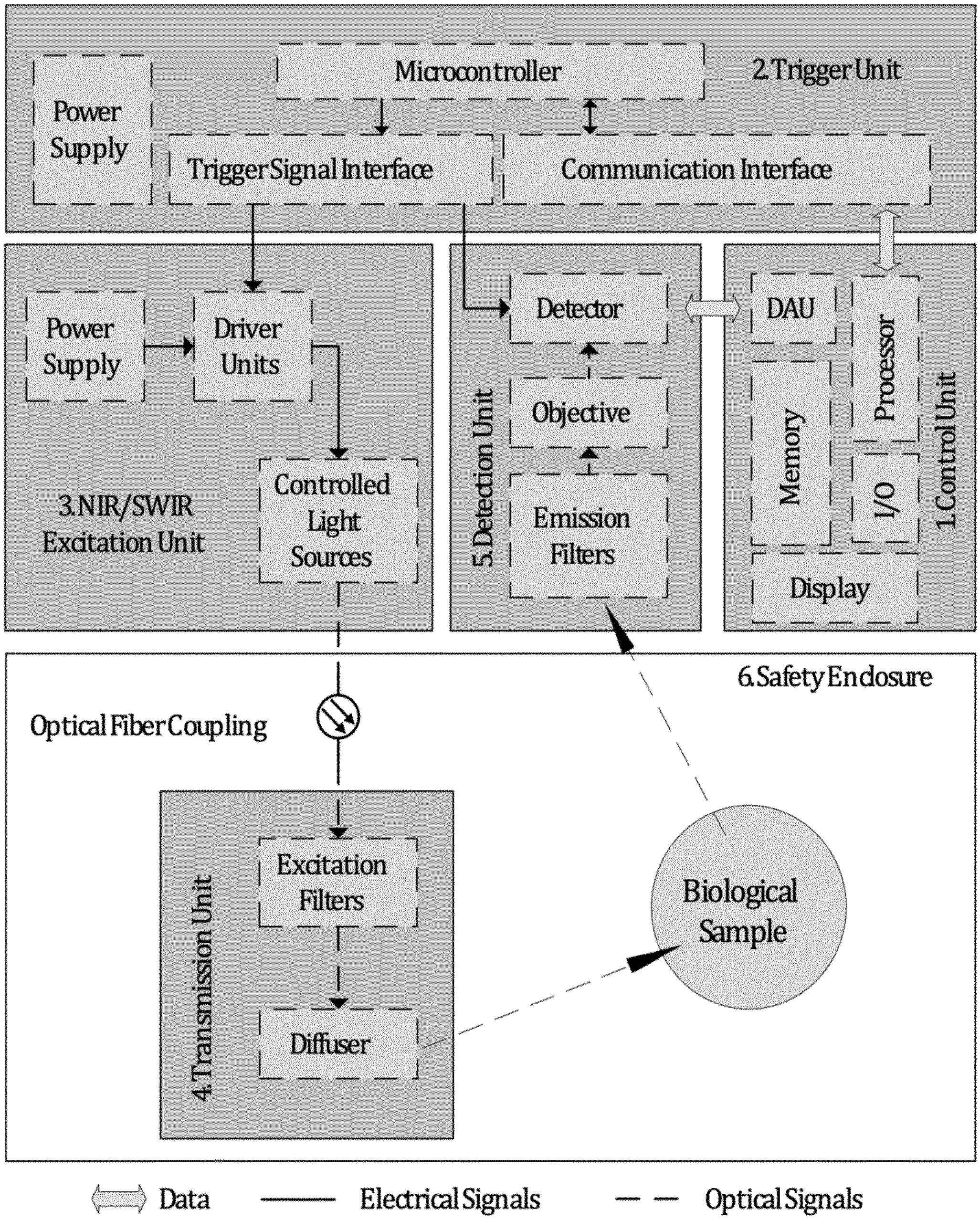
FIG. 2: Second exemplary functional diagram of the imaging system of the present invention comprising: a control unit, a trigger unit, an excitation unit, a transmission unit, a detection unit and a safety enclosure.

In some aspects, the system of the present invention has the specification and/or functionality as described in FIG. 2.

In some aspects, the system and method of the present invention employing high-power excitation sources in combination with state of the art InGaAs SWIR detectors (e.g., HgCdTe or MCT, Germanium, superconducting nanowires, PbS sensitized silicon chips, bolometers, schottky barrier and pyroelectric detectors; or any other detector technology sensitive between 1000 and 2500 nm) and SWIR illuminated fluorophores (e.g., FIGS. 1 and 2).

In some aspects, the systems and methods of the present invention are capable of synchronizing the emission of light sources and SWIR detectors and acquire image data faster than the detectable movements of biological systems.

In some aspects, the sequentially triggered excitation sources of the present invention illuminate their corresponding fluorophores in the biological sample and detected by synchronized InGaAs detectors to achieve a multi-color SWIR imaging system.

In some aspects, the synchronized emitter-detector imaging system of the present invention also enables high-dynamic range (HDR) imaging and fluid flow-velocimetry mapping of biological structures in SWIR spectrum.

In some aspects, the system and method of the present invention provide the following exemplary functionality (e.g., FIGS. 1 and 2). Given a biological sample embedded with targeted SWIR probes, the system can be accessed and controlled to attain a real-time multi-color SWIR fluorescence image data. Probe-specific optimized excitation and emission filters are designed and integrated with the system to achieve high optical sensitivity of target structures. User via control unit programmatically accesses the microcontroller of the trigger unit and the detector. Subsequently, the trigger sequence is uploaded to the trigger unit and detector parameters are assigned to the detector unit. The trigger sequence algorithm then initiates and controls the synchronization of VIS/NIR/SWIR excitation unit and detector unit to achieve real-time multi-color SWIR fluorescence image acquisition. The microcontroller trigger signal interface transmits the electrical signals to the excitation driver unit and detector to perform image acquisition of VIS/NIR/SWIR excited biological structures. The high-through put design of the system can operate in higher frequencies than detectable motion of the biological structures. Thus, achieving an in vivo real-time multi-color SWIR fluorescence image acquisition system.

In some aspects, the system/method of the present invention comprising/providing one or more of the following: a control unit (e.g., an exemplary control unit as described herein), a trigger unit (e.g., an exemplary trigger unit as described herein), an excitation unit (e.g., an excitation unit as described herein), a transmission unit (e.g., an exemplary transmission unit as described herein), a detection unit (e.g., an exemplary detection unit as described herein) and safety enclosure (e.g., an exemplary safety enclosure as described herein).

In some aspects, the system/method of the present invention comprising/providing a sample location (e.g., a biological sample location, configured to receive, comprising or consisting of: a biological sample (e.g., a cell, tissue or cell culture), a clinical sample (e.g., a biopsy, bodily fluid, total body water, amniotic fluid, pleural fluid, peritoneal fluid, venipuncture, radial artery puncture, intracellular fluid (ICF), extracellular fluid (ECF), blood, serum, saliva, excreta (e.g., feces or urine), sperm, semen, lymphatic fluid, interstitial fluid, intravascular fluid, transcellular fluid, cerebrospinal fluid (CSF), body tissue, tissue fluid or post-mortem sample), a subject (e.g., a mammalian subject, e.g., human), a specimen (e.g., a model organism, e.g., a rodent, e.g., *Mus musculus* or *Rattus norvegicus*), a biocomposite (e.g., comprising a tissue scaffold) and/or mixture/s thereof, e.g., a cell (e.g., in vivo, ex vivo or in vitro cell), a cell culture, a tissue (in vivo, ex vivo or in vitro tissue), a graft (e.g., an autograft, isograft, allograft or xenograft), an organ, an animal or whole body or a fragment/s or portion/s thereof).

In some aspects, the system/method of the present invention is non-invasive.

In some aspects, the system/method of the present invention are used in one or more of the following applications: Multicolor Real-time Image Acquisition (e.g., in SWIR, e.g., as described in the examples section herein); High-dynamic Range Image Acquisition (e.g., in SWIR, e.g., as described in the examples section herein); Dark-current Noise-less imaging (e.g., in SWIR, e.g., as described in the examples section herein); Three-dimensional Imaging (e.g., in SWIR, e.g., as described in the examples section herein); Strobo-Effected Image Acquisition (e.g., in SWIR, e.g., as described in the examples section herein); Emission & Excitation Fingerprint (e.g., as described in the examples section herein)

In some aspects, the system/method of the present invention are provided according to FIG. 1 and/or FIG. 2 and/or Table 1 and/or Table 2 and/or exemplary non-limiting specifications/functionalities as described herein above.

In some aspects, the present invention provides novel SWIR targeted fluorophores, preferably flavylium heptamethine fluorophores/dyes, e.g., as described in the examples section herein below, e.g., Julo7 (or elsewhere, e.g., as in WO 2018/226720 A1).

In some aspects, the present invention provides synthesis of novel SWIR targeted fluorophores, e.g., flavylium heptamethine fluorophores/dyes, e.g., as described in the examples section herein below, e.g., Julo7 (or elsewhere, e.g., WO 2018/226720 A1).

In some aspects, the present invention provides novel SWIR targeted fluorophores, e.g., flavylium heptamethine fluorophores/dyes, e.g., as described in the examples section herein below, e.g., Julo7 synthesised as described in the examples section herein below (or elsewhere, e.g., WO 2018/226720 A1.

In some aspects, the present invention provides SWIR targeted fluorophores, preferably flavylium heptamethine fluorophores/dyes, e.g., ICG and/or Julo7 for use in methods/systems of the present invention.

In some aspects, the systems/methods of the present invention utilize indocyanine green (ICG) fluorophore:

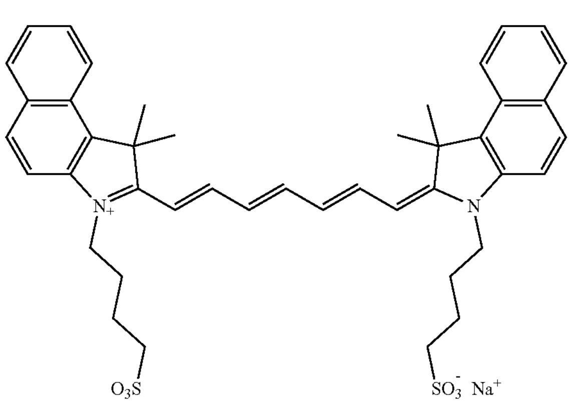

Indocyanine green (ICG)

In some aspects, the systems/methods of the present invention utilize Julo7 fluorophore, a red-shifted by ~35 nm (compared to Flav7 fluorophore) julolidine derivative with absorption at 1061 nm and emission at 1088 nm):

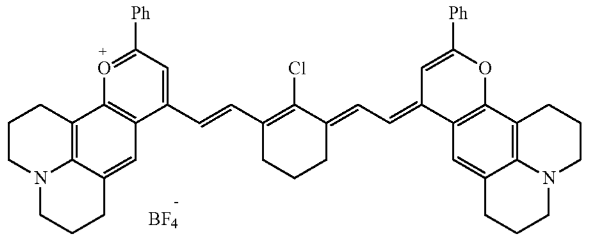

Julo7

Figure 17:
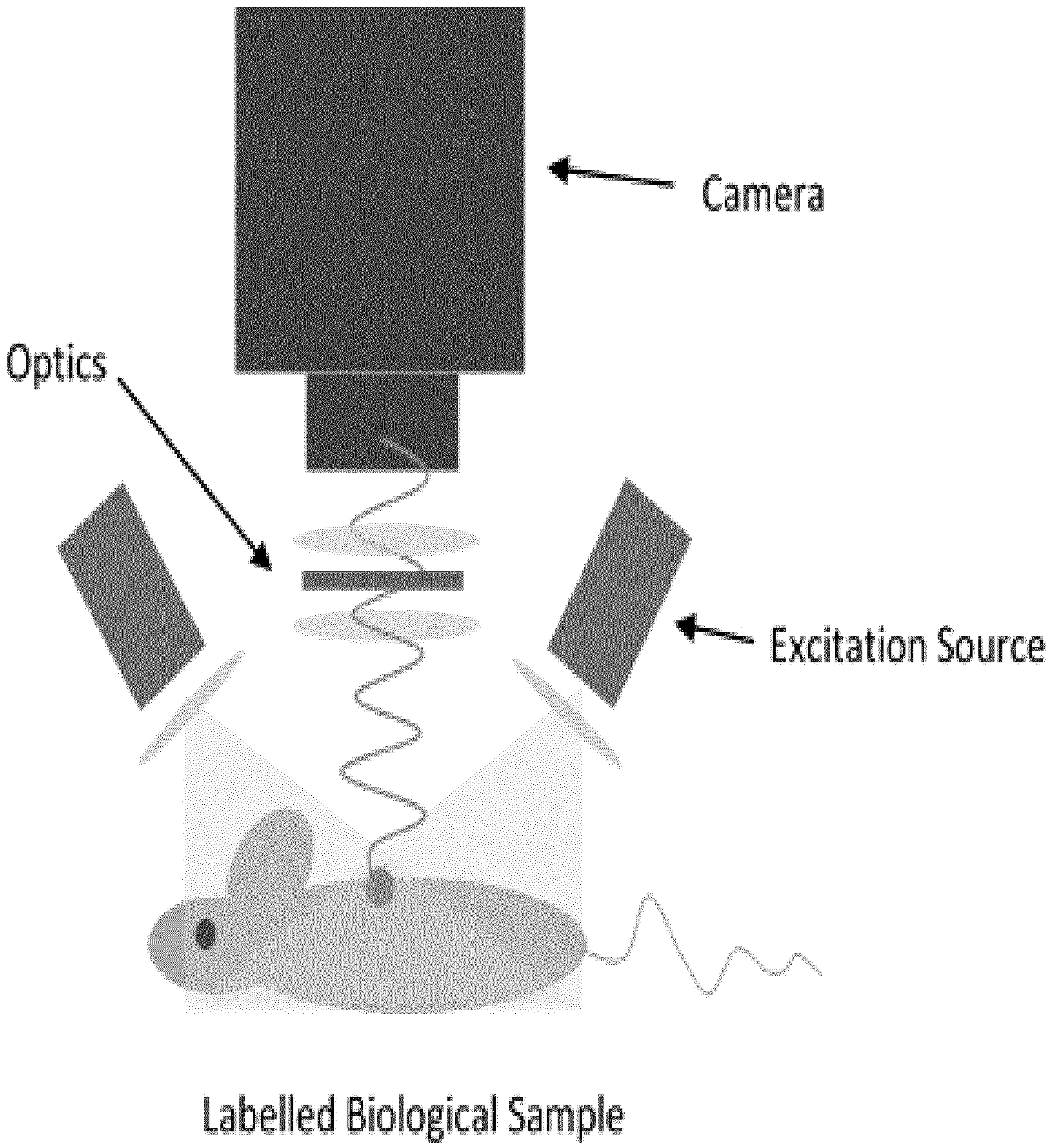
FIG. 17: First exemplary schematics of the method and device for imaging fluorescent proteins in near- and short-wave infrared requiring a (labelled) fluorescent biological sample, an optical setup (e.g., microscopic, mesoscopic or macroscopic) for detection and an excitation light source.
Figure 18:
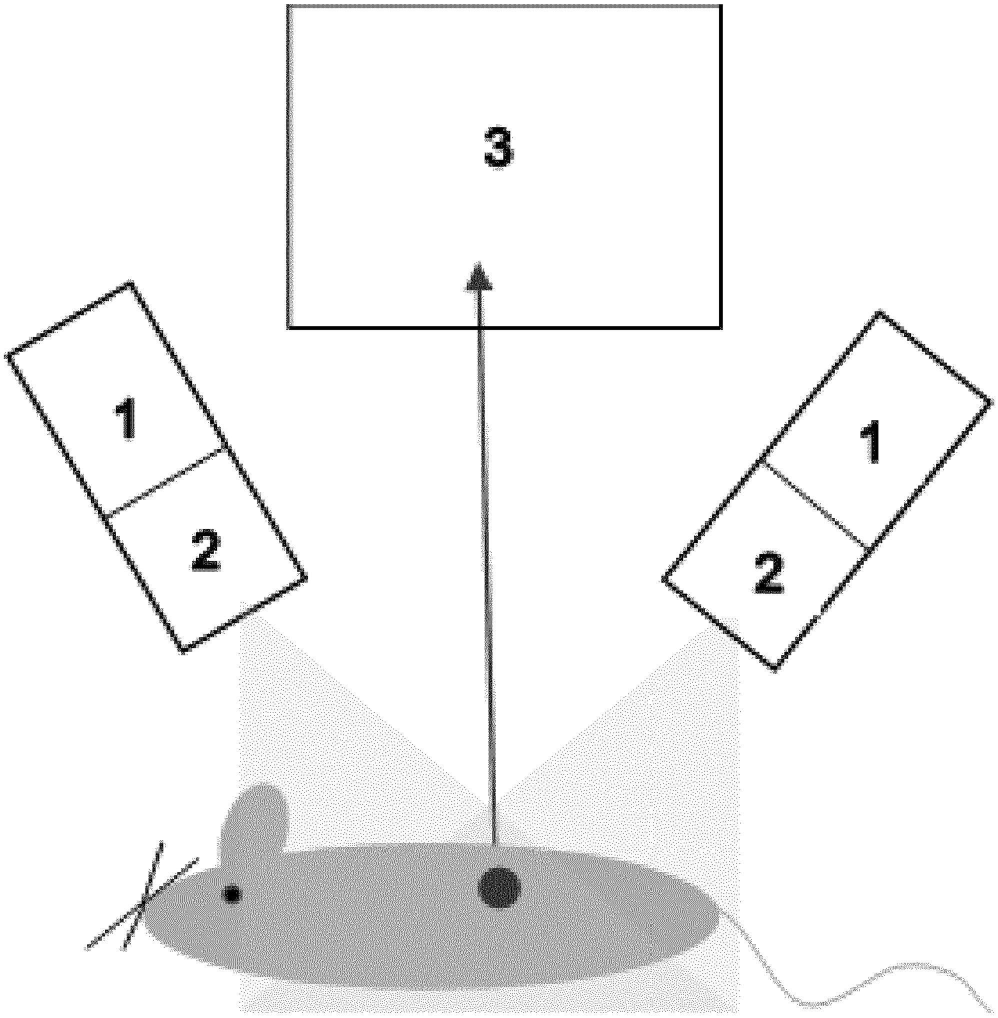
FIG. 18: Second exemplary schematics of the method and device for imaging fluorescent proteins in near- and short-wave infrared requiring a (labelled) fluorescent biological sample, an optical setup for detection and an excitation light source, wherein "1" may be an excitation unit, which may comprise one or more of the following: a power supply and a light source; "2" may be a transmission unit, which may comprise one or more of the following: an excitation filter and optical elements (e.g., lense/s and/or diffuser); "3" may be a detection unit, which may comprise one or more of the following: optical elements, emission filter, detector, processor, data storage and display.

In some aspects, the system/method of the present invention are provided according to FIG. 17 and/or FIG. 18.

In some aspects, the system of the present invention is the system for imaging a biological sample (e.g., a tissue, e.g., in vivo, ex vivo or in vitro tissue; an organ, whole body or a fragment/s or portion/s thereof) comprising: a fluorescent probe comprising a fluorescent polypeptide; an excitation source configured to emit electromagnetic radiation within an absorption spectrum of the fluorescent polypeptide; and a detector configured to detect the tail portion (e.g., said tail portion is not within the emission peak wavelength range of said fluorescent polypeptide) of the fluorescence of the fluorescent polypeptide, wherein said detector is configured to detect in the near infrared (NIR) wavelength range of the electromagnetic spectrum (e.g., in the wavelength range from about 700 nm to about 1000 nm) and/or in the shortwave infrared (SWIR) wavelength range of electromagnetic spectrum (e.g., in the wavelength range from about 1000 nm to about 2500 nm).

In some aspects, the method of the present invention is the method for imaging a biological sample (e.g., a tissue, e.g., in vivo, ex vivo or in vitro tissue; an organ, whole body or a fragment/s or portion/s thereof) comprising: exposing at least a portion of said biological sample (e.g., a portion of said tissue) comprising a fluorescent probe to a suitable excitation source of the fluorescent probe, wherein the fluorescent probe comprises a fluorescent polypeptide; and detecting the tail portion (e.g., said tail portion is not within the emission peak wavelength range of said fluorescent polypeptide) of the fluorescence of the fluorescent polypeptide, wherein said detecting is carried out in the near infrared (NIR) wavelength range of the electromagnetic spectrum (e.g., in the wavelength range from about 700 nm to about 1000 nm) and/or in the shortwave infrared (SWIR) wavelength range of the electromagnetic spectrum (e.g., in the wavelength range from about 1000 nm to about 2500 nm).

In some aspects, the methods/systems of the present invention are the method/system for multiplexed and/or multicolor imaging of the biological sample according to/comprising any one of the embodiments/items/features described herein.

In some aspects, the fluorescent component of the present invention is the fluorescent polypeptide of the present invention.

In some aspects, the present invention provides polypeptides of the present invention for use in the methods/systems of the present invention (e.g., SEQ ID NO: 1-5 and/or other fluorescent polypeptides as described herein).

Compared to existing imaging systems and methods the systems and methods for real-time multicolor shortwave infrared fluorescence imaging of present invention inter alia offer the following advantages that are aspects of the present invention:

- Wide range of high-power fiber-coupled light sources and targeted SWIR probes for multicolor imaging;
- Highly scalable, user controllable and synchronized emitter-detector system for in vivo biomedical imaging;
- High-dynamic range imaging of biological structures in SWIR;
- High throughput detector and microcontroller based sequential trigger for real-time multicolor imaging in SWIR spectrum;
- Synchronizing the emission of light sources and SWIR detectors and acquiring image data faster than the detectable movements of biological systems;
- The synchronized emitter-detector imaging system also enabling high-dynamic range (HDR) imaging and fluid flow-velocimetry mapping of biological structures in SWIR spectrum.
- Full control over excitation and detection enabling multiple applications;
- Imaging in the SWIR region benefiting from less scattering, autofluorescence, etc.
- Possibility to image off-peak, emission signal of fluorophores/fluorescent polypeptides sufficient off-peak;
- Multi-color real-time imaging in the SWIR;
- Compatible with Matlab and Simulink programming environments;
- 16 MHz 32 bit AVR Microcontroller based trigger unit;
- Flexible and reconfigurable optical system;
- Not limited to fluorescence imaging; can be used in reflection imaging without fluorophores;
- The system can be implemented in an event driven control algorithm to increase the time resolution and improve the inter-delays without modifying the hardware of the system.
- The system can integrate high-performance SWIR detector with minimal modification to the existing hardware and software.
- The time-resolution of the system can be greatly reduced by incorporating higher frequency, off-the-shelf microcontrollers. The existing trigger unit will be redesigned to accommodate faster system performance bringing the system time resolution in the order of few nanoseconds. In such instance, there is also potential to expand the number of controllable peripherals (light sources and detectors).
- The time-delays of the system can be further reduced by re-designing the trigger controller as mentioned above and incorporating faster excitation side light source drivers/controllers
- Non-invasive imaging
- Reduction of melanin absorption in the SWIR (e.g., in/for in vivo imaging methods, e.g., in genetically-labelled or transgenic model organisms, e.g., mice e.g., as described in Example 12 herein); Melanin is a hurdle for conventional florescence imaging in VIS/NIR range because black melanin spots on the skin absorb emission signal from deeper structures; This absorption is much weaker in the SWIR range; A majority of commercial genetically-modified mice have strong melanin presence due to their genetic background; imaging in the SWIR range allows any mouse to be used regardless of genetic background;
- SWIR imaging according to/with methods and/or systems of the present invention is a solution for a non-invasive imaging of tissues and organisms (e.g., with or without markers such as fluorescent proteins or dyes) in the presence of melanin e.g., as described in Example 12 herein.

The invention is also characterized by the following items:

1. A method for multiplexed and/or multicolor imaging of a sample location (e.g., a biological sample location, configured to receive, comprising or consisting of: a biological sample (e.g., a cell, tissue or cell culture), a clinical sample (e.g., a biopsy, bodily fluid, total body water, amniotic fluid, pleural fluid, peritoneal fluid, venipuncture, radial artery puncture, intracellular fluid (ICF), extracellular fluid (ECF), blood, serum, saliva, excreta (e.g., feces or urine), sperm, semen, lymphatic fluid, interstitial fluid, intravascular fluid, transcellular fluid, cerebrospinal fluid (CSF), body tissue, tissue fluid or post-mortem sample), a subject (e.g., a mammalian subject, e.g., human), a specimen (e.g., a model organism, e.g., a rodent, e.g., *Mus musculus* or *Rattus norvegicus*), a biocomposite (e.g., comprising a tissue scaffold) and/or mixture/s thereof, e.g., a cell (e.g., in vivo, ex vivo or in vitro cell), a cell culture, a tissue (in vivo, ex vivo or in vitro tissue), a graft (e.g., an autograft, isograft, allograft or xenograft), an organ, an animal or whole body or a fragment/s or portion/s thereof), said method comprising:
   i) exposing a portion of said sample location to a first light pulse/s (e.g., an excitation light pulse/s), wherein said first light pulse/s having:
      (a) a first state (e.g., said state has one or more of the properties of a wavelength and/or spectrum; e.g., linear, circular and elliptical polarization, intensity, incident angle and pulse length); or
      (b) a first wavelength;
      in order to illuminate (e.g., for reflectance imaging) or excite a first component (e.g., fluorescent component, e.g., VIS/NIR/SWIR fluorophores, preferably polymethine fluorophores/dyes, e.g., ICG, IRDye800CW, Julo5 and/or Julo7, e.g., WO 2018/226720A1, or autofluorescent tissue component, e.g. pigments, preferably lipofuscin), chemical composition, surface and/or region in the portion of said sample location (e.g., a first dye comprised by the portion of said sample location);
   ii) exposing the portion of said sample location to at least a second light pulse/s (e.g., a second excitation light pulse/s) having:
      (c) a second state (e.g., said state has one or more of the properties of a wavelength and/or spectrum; e.g., linear, circular and elliptical polarization, intensity, incident angle and pulse length), which is different from the first state of (a); or
      (d) a second wavelength, which is different from the first wavelength of (b);
      in order to illuminate (e.g., for reflectance imaging) or excite a second component (e.g., fluorescent component, e.g., VIS/NIR/SWIR fluorophores, preferably polymethine fluorophores/dyes, e.g., ICG, IRDye800CW, Julo5 and/or Julo7, e.g., WO 2018/226720A1, or autofluorescent tissue component, e.g. pigments, preferably lipofuscin), chemical composition, surface and/or region in the portion of said sample location (e.g., a second dye comprised by the portion of said sample location), preferably said second component, chemical composition, surface or region is different from said first component, chemical composition, surface or region;
   wherein the first light pulse/s (e.g., the first excitation light pulse/s) and the second (and/or subsequent) light pulse/s (e.g. the second excitation light pulse/s) are provided sequentially or alternately;
   iii) detecting light reflected or emitted by the first and the second component (e.g., fluorescent components or dyes), chemical composition, surface and/or region in the portion of said sample location (e.g., the first and the second fluorescent components or dyes) by an imaging device, wherein the peak emission wavelength of at least one component, chemical composition, surface and/or region in the portion of said sample location lies outside of the detection range of the imaging device, the detection process including:
      aa) switching the imaging device, in a sequential or an alternating manner, between a first configuration (or state) during which the imaging device is responsive to a first electromagnetic radiation and a second configuration (or state) during which the imaging device is:
         i') responsive to a second electromagnetic radiation (e.g., said first and second electromagnetic radiations are not identical); or
         ii') unresponsive to electromagnetic radiation,
      wherein the switching of the first configuration (or state) is triggered by the provision of the light pulse/s (e.g., by the means of provision of electrical pulses to the light sources).

2. The method according to any one of preceding items, said method comprising:
   i) exposing a portion of said sample location to a first light pulse (e.g., an excitation light pulse), wherein said first light pulse having a first wavelength;
      in order to illuminate (e.g., for reflectance imaging) or excite a first dye comprised by the portion of said sample location);
   ii) exposing the portion of said sample location to at least a second light pulse (e.g., a second excitation light pulse) having a second wavelength, which is different from the first wavelength; in order to illuminate (e.g., for reflectance imaging) or excite a second dye comprised by the portion of said sample location);
   wherein the first light pulse (e.g., the first excitation light pulse) and the second light pulse (e.g. the second excitation light pulse) are provided sequentially or alternately;
   iii) detecting light reflected or emitted by the first and second component, chemical composition, surface and/or region in the portion of said sample location (e.g., the first dye and the second dye) by an imaging device, wherein the peak emission wavelength of at least one component, chemical composition, surface and/or region in the portion of said sample location lies outside of the detection range of the imaging device, the detection process including:
      aa) switching the imaging device, in a sequential or alternating manner, between a first configuration (or state) during which the imaging device is responsive to a first electromagnetic radiation and a second configuration (or state) during which the imaging device is responsive to a second electromagnetic radiation (e.g., said first and said second electromagnetic radiations are not identical), wherein the switching of the first configuration is triggered by the provision of the light pulse (e.g., by the means of provision of electrical pulses to the light sources).

3. The method according to any one of preceding items, further comprising: providing an optical filter in the optical path between the portion of said sample location and the imaging device, the optical filter being configured to block the first excitation light and the second excitation light.
4. The method according to any one of preceding items, wherein the optical filter is configured as a longpass or bandpass filter with a cut-on wavelength in the micrometer range.
5. The method according to any one of preceding items, wherein the detection range of the imaging device lies in the micrometer range, preferably in the short-wave infrared (SWIR) range.
6. The method according to any one of preceding items, wherein the first and the second excitation light pulses are provided at the same rate or at the different rate.
7. The method according to any one of preceding items, wherein the pulse length of the first and second excitation light pulses is: i) 10 ms or shorter; ii) up to several (e.g., 1, 2, 3, 4, 5, 6, 7, 8, 9, or 10) seconds; or iii) up to several (e.g., 1, 2, 3, 4, 5, 6, 7, 8, 9, or 10) minutes.
8. The method according to any one of preceding items, wherein the duty cycle of the first and second pulses is: i) 1% or less; or ii) up to 100%.
9. The method according to any one of preceding items, wherein the first excitation light pulse/s and the second excitation light pulse/s impinge on the portion of said sample location from the same spatial direction.
10. The method according to any one of preceding items, wherein the first excitation light pulse/s and the second excitation light pulse/s impinge on the portion of said sample location from different spatial directions.
11. The method according to any one of preceding items, as long as dependent on item 4, wherein the peak emission wavelength of at least one of the dyes lies below the cut-on wavelength of the longpass filter.
12. The method according to any one of preceding items, wherein for any wavelength within the detection range of the imaging device the emission intensity of at least one of the dyes amounts to: i) 1% or less, preferably to 0.1% or less, of the peak emission intensity of the respective dye; ii) 30% or less of the peak emission intensity of the respective dye; iii) up to 100% of the peak emission intensity of the respective dye; or iv) in the range between 30%-100% of the peak emission intensity of the respective dye.
13. The method according to any one of preceding items, wherein the switching of the device into the first configuration (or state) is triggered by the provision of the light pulse/s such that the imaging device is switched into the first configuration (or state) simultaneously with or within 2 microseconds after the emission of any one of the first and second excitation light pulse/s.
14. The method according to any one of preceding items, wherein said method does not comprise a moving and/or switching an optical filter or optical filter array.
15. The method according to any one of preceding items, wherein said method comprising providing only one optical filter.
16. The method according to any one of preceding items, wherein said method comprising providing a high-power excitation source in combination with an InGaAs SWIR detectors and VIS/NIR/SWIR illuminated fluorophores (e.g., polymethine dyes, e.g., as described in examples section herein).
17. The method according to any one of preceding items, wherein said method is one or more of the following methods:
    i) an in vivo, ex vivo and/or in vitro method (e.g., a non-invasive method);
    ii) a diagnostic, therapeutic, surgical (e.g., intraoperative imaging, fluorescence guided surgery) and/or screening method (e.g., management and treatment of voice disorders);
    iii) a tissue engineering and/or transplantation method;
    iv) a three-dimensional (3D) bioprinting method;
    v) a real-time imaging method (e.g., real-time multiplexed imaging in non-transparent animals e.g., as described in the examples section herein);
    vi) a High-Dynamic-Range (HDR) imaging method, preferably HDR imaging method of biological structures in SWIR;
    vii) a fluorescence imaging method;
    viii) a multicolor real-time image acquisition (e.g., in SWIR, e.g., as described in the examples section herein, e.g., Imaging of Awake State, Intestinal Mobility Tracking, Lymphatic Imaging);
    ix) a high-dynamic range image acquisition (e.g., in SWIR, e.g., as described in the examples section herein);
    x) a dark-current noise-less imaging (e.g., in SWIR, e.g., as described in the examples section herein);
    xi) a three-dimensional imaging (e.g., in SWIR, e.g., as described in the examples section herein);
    xii) a strobo-effected image acquisition (e.g., in SWIR, e.g., as described in the examples section herein);
    xiii) an emission and excitation fingerprint (e.g., as described in the examples section herein);
    xiv) a method for reduction of melanin absorption in the SWIR (e.g., as described in the examples section herein);
    xv) a method fora non-invasive imaging of tissues and/or organisms (e.g., with or without markers such as fluorescent proteins or dyes) in the presence of melanin (e.g., as described in the examples section herein).
18. A system for multiplexed and/or multicolor imaging of a sample location (e.g., a biological sample location, configured to receive, comprising or consisting of: a biological sample (e.g., a cell, tissue or cell culture), a clinical sample (e.g., a biopsy, bodily fluid, total body water, amniotic fluid, pleural fluid, peritoneal fluid, venipuncture, radial artery puncture, intracellular fluid (ICF), extracellular fluid (ECF), blood, serum, saliva, excreta (e.g., feces or urine), sperm, semen, lymphatic fluid, interstitial fluid, intravascular fluid, transcellular fluid, cerebrospinal fluid (CSF), body tissue, tissue fluid or post-mortem sample), a subject (e.g., a mammalian subject, e.g., human), a specimen (e.g., a model organism, e.g., a rodent, e.g., *Mus musculus* or *Rattus norvegicus*), a biocomposite (e.g., comprising a tissue scaffold) and/or mixture/s thereof, e.g., a cell (e.g., in vivo, ex vivo or in vitro cell), a cell culture, a tissue (in vivo, ex vivo or in vitro tissue), a graft (e.g., an autograft, isograft, allograft or xenograft), an organ, an animal or whole body or a fragment/s or portion/s thereof), said system comprising:
    i) a first light source (e.g., a laser, LED, lamp or any other suitable light source) configured to operate at a first wavelength;

ii) at least a second light source (e.g., a laser, LED, lamp or any other suitable light source) configured to operate at a second wavelength;

iii) an imaging device configured to detect electromagnetic radiation;

iv) a control unit coupled to the first light source (e.g., a laser, LED, lamp or any other suitable light source), the second light source (e.g., a laser, LED, lamp or any other suitable light source) and the imaging device, wherein the control unit is configured to control the first light source to provide first excitation light pulse/s and to control the second light source to provide second excitation light pulse/s in sequential or an alternating manner; wherein the control unit is further configured to switch the imaging device in a sequential or an alternating manner, between a first state during which the imaging device is responsive to a first electromagnetic radiation and a second state during which the imaging device is a) responsive to a second electromagnetic radiation (e.g., said first and second electromagnetic radiations are not identical); or b) unresponsive to electromagnetic radiation;

wherein the system is configured such that the switching of the imaging device into the first state is triggered by the provision of the light pulse/s (e.g., by the means of provision of electrical pulses to the light sources).

19. The system according to any one of preceding items, wherein said system comprises two or more light sources (e.g., lasers, LEDs, lamps or any other suitable light sources), preferably said light sources are configured to be operated (e.g., be switched on) simultaneously during pulses (e.g., definable, e.g., operator-definable or certain, pulses).

20. The system according to any one of preceding items, further comprising: an optical filter in the optical path between the portion of said sample location and the imaging device, the optical filter being configured to block the first excitation light and the second excitation light.

21. The system according to any one of preceding items, wherein the optical filter is configured as a longpass or bandpass filter with a cut-on wavelength in the micrometer range.

22. The system according to any one of preceding items, wherein the detection range of the imaging device lies in the micrometer range, preferably in the short-wave infrared (SWIR) range.

23. The system according to any one of preceding items, wherein the first and the second excitation light pulses are provided at the same rate or at the different rate.

24. The system according to any one of preceding items, wherein the pulse length of the first and second excitation light pulses is: i) 10 ms or shorter; ii) up to several (e.g., 1, 2, 3, 4, 5, 6, 7, 8, 9, or 10) seconds; or iii) up to several (e.g., 1, 2, 3, 4, 5, 6, 7, 8, 9, or 10) minutes.

25. The system according to any one of preceding items, wherein the duty cycle of the first and second pulses is: i) 1% or less; or ii) up to 100%.

26. The system according to any one of preceding items, wherein the first excitation light pulse/s and the second excitation light pulse/s impinge on the portion of said sample location from the same spatial direction.

27. The system according to any one of preceding items, wherein the first excitation light pulse/s and the second excitation light pulse/s impinge on the portion of said sample location from different spatial directions.

28. The system according to any one of preceding items, as long as dependent on item 20, wherein the peak emission wavelength of at least one of the dyes lies below the cut-on wavelength of the longpass filter.

29. The system according to any one of preceding items, wherein for any wavelength within the detection range of the imaging device the emission intensity of at least one of the dyes amounts to: i) 1% or less, preferably to 0.1% or less, of the peak emission intensity of the respective dye; ii) 30% or less of the peak emission intensity of the respective dye; iii) up to 100% of the peak emission intensity of the respective dye; or iv) in the range between 30%-100% of the peak emission intensity of the respective dye.

30. The system according to any one of preceding items, wherein the switching of the device into the first configuration (or state) is triggered by the provision of the light pulse/s such that the imaging device is switched into the first configuration (or state) simultaneously with or within 2 microseconds after the emission of any one of the first and second excitation light pulse/s.

31. The system according to any one of preceding items, further comprising one or more of the following: a trigger unit (e.g., an exemplary trigger unit as described herein), an excitation unit (e.g., an excitation unit as described herein), a transmission unit (e.g., an exemplary transmission unit as described herein), a detection unit (e.g., an exemplary detection unit as described herein) and safety enclosure (e.g., an exemplary safety enclosure as described herein).

32. The system according to any one of preceding items, wherein said system does not comprise a movable optical filter or a movable optical filters array.

33. The system according to any one of preceding items, wherein said system comprises only one optical filter.

34. The system according to any one of preceding items, wherein said system comprises a high-power excitation source in combination with InGaAs SWIR detectors and SWIR illuminated fluorophores (e.g., polymethine dyes, e.g., as described in examples section herein, e.g., ICG and/or Julo7 or elsewhere, e.g., in WO 2018/226720A1).

35. The system according to any one of preceding items, wherein said system is capable of High Dynamic Range (HDR) imaging.

36. The system according to any one of preceding items, wherein said system is capable of a real-time imaging.

37. Use of the system according to any one of preceding items in one or more of the following:

i) an in vivo, ex vivo and/or in vitro method (e.g., a non-invasive method);

ii) a diagnostic, therapeutic, surgical (e.g., intraoperative imaging, fluorescence guided surgery) and/or screening method (e.g., management and treatment of voice disorders);

iii) a tissue engineering and/or transplantation method;

iv) a three-dimensional (3D) bioprinting method;

v) a real-time imaging method (e.g., real-time multiplexed imaging in non-transparent animals e.g., as described in the examples section herein);

vi) a fluorescence imaging method;

vii) a multicolor real-time image acquisition (e.g., in SWIR, e.g., as described in the examples section herein, e.g., Imaging of Awake State, Intestinal Mobility Tracking, Lymphatic Imaging);

viii) a high-dynamic range image acquisition (e.g., in SWIR, e.g., as described in the examples section herein);

ix) a dark-current noise-less imaging (e.g., in SWIR, e.g., as described in the examples section herein);

x) a three-dimensional imaging (e.g., in SWIR, e.g., as described in the examples section herein);

xi) a strobo-effected image acquisition (e.g., in SWIR, e.g., as described in the examples section herein);

xii) an emission and excitation fingerprint (e.g., as described in the examples section herein);

xiii) for reduction of melanin absorption in the SWIR (e.g., as described in the examples section herein);

xiv) for a non-invasive imaging of tissues and/or organisms (e.g., with or without markers such as fluorescent proteins or dyes) in the presence of melanin (e.g., as described in the examples section herein).

38. A polymethine fluorophore compound (e.g., as described in Example 9 herein below, or elsewhere, e.g., in WO 2018/226720 A1), preferably said compound comprises the moiety having the following formula:

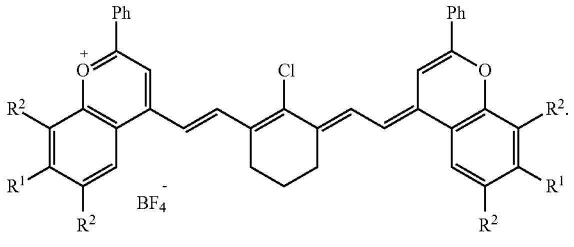

39. A composition comprising the polymethine fluorophore compound according to any one of preceding items.

40. The composition according to any one of preceding items, wherein said composition is a diagnostic composition.

41. The polymethine fluorophore compound according to any one of preceding items, for use in one or more of the method or system according to any one of preceding items.

42. Use of the polymethine fluorophore compound according to any one of preceding items in one or more of the following:

i) an in vivo, ex vivo and/or in vitro method (e.g., a non-invasive method);

ii) a diagnostic, therapeutic, surgical (e.g., intraoperative imaging) and/or screening method (e.g., management and treatment of voice disorders);

iii) a tissue engineering and/or transplantation method;

iv) a three-dimensional (3D) bioprinting method;

v) a real-time imaging method (e.g., real-time multiplexed imaging in non-transparent animals e.g., as described in the examples section herein);

vi) a fluorescence imaging method;

vii) a multicolor real-time image acquisition (e.g., in SWIR, e.g., as described in the examples section herein, e.g., Imaging of Awake State, Intestinal Mobility Tracking, Lymphatic Imaging);

viii) a high-dynamic range image acquisition (e.g., in SWIR, e.g., as described in the examples section herein);

ix) a dark-current noise-less imaging (e.g., in SWIR, e.g., as described in the examples section herein);

x) a three-dimensional imaging (e.g., in SWIR, e.g., as described in the examples section herein);

xi) a strobo-effected image acquisition (e.g., in SWIR, e.g., as described in the examples section herein);

xii) an emission and excitation fingerprint (e.g., as described in the examples section herein).

43. A system for imaging a biological sample (e.g., a tissue, e.g., in vivo, ex vivo or in vitro tissue; an organ, whole body or a fragment/s or portion/s thereof) comprising:

i) a fluorescent probe comprising a fluorescent polypeptide;

ii) an excitation source configured to emit electromagnetic radiation within an absorption spectrum of the fluorescent polypeptide; and iii) a detector configured to detect the tail portion (e.g., said tail portion is not within the emission peak wavelength range of said fluorescent polypeptide) of the fluorescence of the fluorescent polypeptide, wherein said detector is configured to detect in the near infrared (NIR) wavelength range of the electromagnetic spectrum (e.g., in the wavelength range from about 700 nm to about 1000 nm) and/or in the shortwave infrared (SWIR) wavelength range of electromagnetic spectrum (e.g., in the wavelength range from about 1000 nm to about 2500 nm).

44. The system of any one of the preceding items, further comprising a computing device, wherein the detector outputs a detected tail portion signal from the fluorescent probe to the computing device.

45. The system of any one of the preceding items, wherein the computing device compares the detected fluorescence signal to an intensity threshold to a subject condition.

46. The system of any one of the preceding items, wherein the subject condition is cirrhotic liver disease.

47. The system of any one of the preceding items, further comprising a display, wherein the detector outputs a detected tail portion signal from the fluorescent probe to the display.

48. The system of any one of the preceding items, wherein said fluorescent polypeptide is capable of emitting the largest portion of its light (e.g., more than 50%, e.g., 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%) in the visible wavelength range of the electromagnetic spectrum, preferably in the wavelength range from about 400 nm to about 800 nm.

49. The system of any one of the preceding items, wherein more than 50% (e.g., 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%) of the emission intensity of said fluorescent polypeptide is in the visible wavelength range of the electromagnetic spectrum, preferably in the wavelength range from about 400 nm to about 800 nm.

50. The system of any one of the preceding items, wherein said fluorescent polypeptide is expressed in said biological sample (e.g., said portion of the tissue).
51. The system of any one of the preceding items, wherein said fluorescent polypeptide is excitable at a wavelength of less than about 800 nm.
52. The system of any one of the preceding items, wherein said fluorescent polypeptide is detectable in the tail of the emission spectrum of said fluorescent polypeptide (e.g., said tail portion is not within the emission peak wavelength range of said fluorescent polypeptide).
53. The system of any one of the preceding items, wherein said fluorescent polypeptide is detectable (e.g., at least partially having its emission) in the near infrared (NIR, e.g., in the range from about 700 nm to about 1000 nm) electromagnetic spectrum and/or in the shortwave infrared (SWIR, e.g., in the range from about 1000 nm to about 2500 nm) electromagnetic spectrum, preferably said fluorescent polypeptide is detectable in the range from about 700 nm to about 2500 nm, further preferably in the range from about 700 nm to about 2000 nm.
54. The system of any one of the preceding items, wherein said fluorescent polypeptide comprises one or more of the following polypeptides:
   i) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to tdTomato polypeptide (SEQ ID NO: 1) (e.g., detectable in SWIR spectrum);
   ii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to SMURF polypeptide (SEQ ID NO: 2);
   iii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iRFP720 polypeptide (SEQ ID NO: 3);
   iv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to 22G (Dronpa) from *Echinophyllia* sp. SC22, Genbank ADE48854.1,
   v) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to aceGFP from *Aequorea coerulescens*, Genbank AAN41637,
   vi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to amFP486 from *Anemonia majano*, Genbank AAF03371,
   vii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to anm2CP from Anthoathecata, Genbank AAR85352,
   viii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to avGFP (classic GFP) from *Aequorea victoria*, Genbank AAA27721,
   ix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to cFP484 from *Clavularia* sp., Genbank AAF03374,
   x) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dendFP from *Dendronephthya* sp., Genbank AAM10625,
   xi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dfGFP from *Olindias formosus*, Genbank BBC28143,
   xii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to DrCBD from *Deinococcus radiodurans*, Genbank AE001825,
   xiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to DsRed from *Discosoma* sp., Genbank AAF03369,
   xiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to EosFP from *Lobophyllia hemprichii*, Genbank AAV54099,
   xv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eqFP578 from *Entacmaea quadricolor*, Genbank H3JQU7,
   xvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eqFP611 from *Entacmaea quadricolor*, Genbank AAN05449,
   xvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to HcRed from *Heteractis crispa*, Genbank Q95W85.1,
   xviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to KikG from *Favia favus*, Genbank BAD95670.1, xix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to KO from *Verrillofungia concinna*, Genbank BAD24721, xx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to LanYFP from *Branchiostoma lanceolatum*, Genbank ACA48232, xxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to SEQ ID NO: 4, xxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mRed7 having SEQ ID NO: 5, xxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to pR3784g from *Nostoc punctiforme*, Genbank WP_012410140, xxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RpBphP1 from *Rhodopseudomonas palustris*, Genbank 5OY5_A, xxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RpBphP2 from *Rhodopseudomonas palustris*, Genbank WP_011158562, xxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RpBphP6 from *Rhodopseudomonas palustris*, Genbank WP_011156523, xxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to TeAPCalpha from *Trichodesmium erythraeum* IMS101, Genbank CP000393.1, xxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to zFP538 from *Zoanthus* sp., Genbank AAF03373, xxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to BphP AGP1 from *Agrobacterium tumefaciens*, Genbank F7UC55_RHIRD, xxx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to sGPC2 from *Acaryochloris marina* (Chee et al., Journal of Biomedical Optics 23(10), 106006 (October 2018)), xxxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to APCF2 from *Chroococcidiopsis thermalis*, Genbank WP_015153831, xxxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to UnaG from *Anguilla japonica*, Genbank AB763906, xxxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RRvT polypeptide (SEQ ID NO: 6), xxxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to tdTomato polypeptide (SEQ ID NO: 7), xxxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to tdimer2(12) polypeptide (SEQ ID NO: 8), xxxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to pcDronpa2 polypeptide (SEQ ID NO: 9), xxxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mScarlet polypeptide (SEQ ID NO: 10), xxxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mKO kappa polypeptide (SEQ ID NO: 11), xxxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Turbo RFP polypeptide (SEQ ID NO: 12), xl) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to PsmOrange polypeptide (SEQ ID NO: 13), xli) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RFP611 polypeptide (SEQ ID NO: 14), xlii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mRuby3 polypeptide (SEQ ID NO: 15), xliii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to vsfGFP-0 polypeptide (SEQ ID NO: 16), xliv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to bfloGFPa1 polypeptide (Bomati et al. (2014). Scientific Reports, 4(1), 5469. doi: 10.1038/srep05469), xlv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to LanYFP polypeptide (SEQ ID NO: 17), xlvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dLanYFP polypeptide (SEQ ID NO: 18), xlvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dVFP polypeptide (SEQ ID NO: 19), xlviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to ccalYFP polypeptide (SEQ ID NO: 20), xlix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to efasGFP polypeptide (SEQ ID NO: 21), l) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to pcDronpa (green) polypeptide (SEQ ID NO: 22), li) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to aeurGFP polypeptide (SEQ ID NO: 23), lii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to miRFP720 polypeptide (SEQ ID NO: 24), liii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iRFP720 polypeptide (SEQ ID NO: 25), liv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Wi-Phy polypeptide (SEQ ID NO: 26), lv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to SNIFP polypeptide (SEQ ID NO: 27), lvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iFP2.0 polypeptide (SEQ ID NO: 28), lvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iRFP713 polypeptide (SEQ ID NO: 29), lviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iFP1.4 polypeptide (SEQ ID NO: 30), lix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mIFP polypeptide (SEQ ID NO: 31), lx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to miRFP709 polypeptide (SEQ ID NO: 32), lxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to miRFP polypeptide (SEQ ID NO: 33), lxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to M35NA polypeptide (SEQ ID NO: 34), lxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to smURFP polypeptide (SEQ ID NO: 35), lxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to TDsmURFP polypeptide (SEQ ID NO: 36), lxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to LanFP2 polypeptide (SEQ ID NO: 37), lxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to HcRed-Tandem polypeptide (SEQ ID NO: 38), lxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Skylan-S polypeptide (SEQ ID NO: 39), lxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to VFP polypeptide (SEQ ID NO: 40), lxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to GFPxm163 polypeptide (SEQ ID NO: 41), lxx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to PlamGFP polypeptide (SEQ ID NO: 42), lxxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to sarcGFP polypeptide (SEQ ID NO: 43), lxxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to psamCFP polypeptide (SEQ ID NO: 44), lxxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to GFPxm18 polypeptide (SEQ ID NO: 45), lxxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Gamillus 0.2 polypeptide (SEQ ID NO: 46), lxxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eGFP polypeptide (SEQ ID NO: 47), lxxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eYFP polypeptide (SEQ ID NO: 48), lxxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Venus polypeptide (SEQ ID NO: 49), lxxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mOrange2 polypeptide (SEQ ID NO: 50), lxxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mCherry polypeptide (SEQ ID NO: 51), lxxx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mTagBFP polypeptide (SEQ ID NO: 52), lxxxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to ZsGreen polypeptide (SEQ ID NO: 53), lxxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to YPet polypeptide (SEQ ID NO: 54), lxxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mCitrine polypeptide (SEQ ID NO: 55), lxxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to CFP polypeptide (SEQ ID NO: 56), lxxxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eCFP polypeptide (SEQ ID NO: 57), lxxxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to GFP polypeptide (SEQ ID NO: 58), lxxxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the iRFP720 polypeptide (SEQ ID NO: 59), lxxxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the tdTomato polypeptide (SEQ ID NO: 60), lxxxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the sfGFP polypeptide (SEQ ID NO: 61), xc) a fluorescent fragment of any one of (i)-(lxxxix).

55. The system of any one of the preceding items, wherein said tdTomato polypeptide (SEQ ID NO: 1) is detectable in the SWIR spectrum (e.g., by the means of a longpass filter configured to isolate the emission electromagnetic radiation of said tdTomato polypeptide with a wavelength greater than 1000 nm).

56. The system of any one of the preceding items, wherein said tdTomato polypeptide (SEQ ID NO: 1) is excitable at a wavelength of about 565 nm.

57. The system of any one of the preceding items, wherein said fluorescent probe comprises two or more different fluorescent polypeptides, preferably said two or more different fluorescent polypeptides are according any one of the preceding items.

58. The system of any one of the preceding items, wherein said system is the system for multiplexed and/or multicolor imaging of said biological sample.

59. The system for multiplexed and/or multicolor imaging of the biological sample of any one of the preceding items, comprising:

i) a first laser light source configured to operate at a first wavelength;

ii) at least a second laser light source configured to operate at a second wavelength;

iii) an imaging device configured to detect electromagnetic radiation;

iv) a control unit coupled to the first laser light source, the second laser light source and the imaging device, wherein the control unit is configured to control the first laser light source to provide first excitation light pulse/s and to control the second laser light source to provide second excitation light pulse/s in sequential manner; wherein the control unit is further configured to switch the imaging device in a sequential manner, between a first state during which the imaging device is responsive to a first electromagnetic radiation and a second state during which the imaging device is responsive to a second electromagnetic radiation, wherein said first and second electromagnetic radiations are not identical;

wherein the system is configured such that the switching of the imaging device into the first state is triggered by the provision of the light pulse/s.

60. Use of the system according to any one of preceding items in one or more of the following:

i) an in vivo, ex vivo and/or in vitro method (e.g., a non-invasive method);

ii) a diagnostic, therapeutic, surgical (e.g., intraoperative imaging, fluorescence guided surgery) and/or screening method (e.g., management and treatment of voice disorders);

iii) a tissue engineering and/or transplantation method;

iv) a three-dimensional (3D) bioprinting method;

v) a real-time imaging method (e.g., real-time multiplexed imaging in non-transparent animals);

vi) a fluorescence imaging method;

vii) a multicolor real-time image acquisition method viii) for reduction of melanin absorption in the SWIR (e.g., as described in the examples section herein);

ix) for a non-invasive imaging of tissues and/or organisms (e.g., with or without markers such as fluorescent proteins or dyes) in the presence of melanin (e.g., as described in the examples section herein.

61. A method for imaging a biological sample (e.g., a tissue, e.g., in vivo, ex vivo or in vitro tissue; an organ, whole body or a fragment/s or portion/s thereof) comprising:

i) exposing at least a portion of said biological sample (e.g., a portion of said tissue) comprising a fluorescent probe to a suitable excitation source of the fluorescent probe, wherein the fluorescent probe comprises a fluorescent polypeptide; and ii) detecting the tail portion (e.g., said tail portion is not within the emission peak wavelength range of said fluorescent polypeptide) of the fluorescence of the fluorescent polypeptide, wherein said detecting is carried out in the near infrared (NIR) wavelength range of the electromagnetic spectrum (e.g., in the wavelength range from about 700 nm to about 1000 nm) and/or in the shortwave infrared (SWIR) wavelength range of the electromagnetic spectrum (e.g., in the wavelength range from about 1000 nm to about 2500 nm).

62. The method of any one of the preceding items, wherein said fluorescent polypeptide is capable of emitting the largest portion of its light (e.g., more than 50%, e.g., 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%) in the visible wavelength range of the electromagnetic spectrum, preferably in the wavelength range from about 400 nm to about 800 nm.

63. The method of any one of the preceding items, wherein more than 50% (e.g., 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%) of the emission intensity of said fluorescent polypeptide is in the visible wavelength range of the electromagnetic spectrum, preferably in the wavelength range from about 400 nm to about 800 nm.

64. The method of any one of the preceding items, wherein said fluorescent polypeptide is expressed in said biological sample (e.g., said portion of the tissue).

65. The method of any one of the preceding items, wherein said fluorescent polypeptide is excitable at a wavelength of less than about 800 nm.

66. The method of any one of the preceding items, wherein said fluorescent polypeptide is detectable in the tail of the emission spectrum of said fluorescent polypeptide (e.g., said tail portion is not within the emission peak wavelength range of said fluorescent polypeptide).

67. The method of any one of the preceding items, wherein said fluorescent polypeptide is detectable (e.g., at least partially having its emission) in the near infrared (NIR, e.g., in the range from about 700 nm to about 1000 nm) electromagnetic spectrum and/or in the short-wave infrared (SWIR, e.g., in the range from about 1000 nm to about 2500 nm) electromagnetic spectrum, preferably said fluorescent polypeptide is detectable in the range from about 700 nm to about 2500 nm, further preferably in the range from about 700 nm to about 2000 nm.

68. The method of any one of the preceding items, wherein said fluorescent polypeptide comprises one or more of the following polypeptides:

i) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to tdTomato polypeptide (SEQ ID NO: 1) (e.g., detectable in SWIR spectrum);

ii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to SMURF polypeptide (SEQ ID NO: 2);

iii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iRFP720 polypeptide (SEQ ID NO: 3);

iv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to 22G (Dronpa) from *Echinophyllia* sp. SC22, Genbank ADE48854.1, v) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to aceGFP from *Aequorea coerulescens*, Genbank AAN41637, vi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to amFP486 from *Anemonia majano*, Genbank AAF03371, vii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to anm2CP from Anthoathecata, Genbank AAR85352, viii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to avGFP (classic GFP) from *Aequorea victoria*, Genbank AAA27721, ix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to cFP484 from *Clavularia* sp., Genbank AAF03374, x) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dendFP from *Dendronephthya* sp., Genbank AAM10625, xi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dfGFP from *Olindias formosus*, Genbank BBC28143, xii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to DrCBD from *Deinococcus radiodurans*, Genbank AE001825, xiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to DsRed from *Discosoma* sp., Genbank AAF03369, xiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to EosFP from *Lobophyllia hemprichii*, Genbank AAV54099, xv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eqFP578 from *Entacmaea quadricolor*, Genbank H3JQU7, xvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eqFP611 from *Entacmaea quadricolor*, Genbank AAN05449, xvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to HcRed from *Heteractis crispa*, Genbank Q95W85.1, xviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to KikG from *Favia favus*, Genbank BAD95670.1, xix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to KO from *Verrillofungia concinna*, Genbank BAD24721, xx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to LanYFP from *Branchiostoma lanceolatum*, Genbank ACA48232, xxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to SEQ ID NO: 4, xxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mRed7 having SEQ ID NO: 5, xxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to pR3784g from *Nostoc punctiforme*, Genbank WP_012410140, xxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RpBphP1 from *Rhodopseudomonas palustris*, Genbank 5OY5_A, xxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RpBphP2 from *Rhodopseudomonas palustris*, Genbank WP_011158562, xxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RpBphP6 from *Rhodopseudomonas palustris*, Genbank WP_011156523, xxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to TeAPCalpha from *Trichodesmium erythraeum* IMS101, Genbank CP000393.1, xxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to zFP538 from *Zoanthus* sp., Genbank AAF03373, xxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to BphP AGP1 from *Agrobacterium tumefaciens*, Genbank F7UC55_RHIRD, xxx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to sGPC2 from *Acaryochloris marina* (Chee et al., Journal of Biomedical Optics 23(10), 106006 (October 2018)), xxxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to APCF2 from *Chroococcidiopsis thermalis*, Genbank WP_015153831, xxxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to UnaG from *Anguilla japonica*, Genbank AB763906, xxxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RRvT polypeptide (SEQ ID NO: 6), xxxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to tdTomato polypeptide (SEQ ID NO: 7), xxxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to tdimer2(12) polypeptide (SEQ ID NO: 8), xxxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to pcDronpa2 polypeptide (SEQ ID NO: 9), xxxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mScarlet polypeptide (SEQ ID NO: 10), xxxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mKO kappa polypeptide (SEQ ID NO: 11), xxxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Turbo RFP polypeptide (SEQ ID NO: 12), xl) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to PsmOrange polypeptide (SEQ ID NO: 13), xli) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to RFP611 polypeptide (SEQ ID NO: 14), xlii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mRuby3 polypeptide (SEQ ID NO: 15), xliii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to vsfGFP-0 polypeptide (SEQ ID NO: 16), xliv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to bfloGFPa1 polypeptide (Bomati et al. (2014). Scientific Reports, 4(1), 5469. doi: 10.1038/srep05469), xlv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to LanYFP polypeptide (SEQ ID NO: 17), xlvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dLanYFP polypeptide (SEQ ID NO: 18), xlvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to dVFP polypeptide (SEQ ID NO: 19), xlviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to ccalYFP polypeptide (SEQ ID NO: 20), xlix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to efasGFP polypeptide (SEQ ID NO: 21), l) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to pcDronpa (green) polypeptide (SEQ ID NO: 22), li) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to aeurGFP polypeptide (SEQ ID NO: 23), lii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to miRFP720 polypeptide (SEQ ID NO: 24), liii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iRFP720 polypeptide (SEQ ID NO: 25), liv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Wi-Phy polypeptide (SEQ ID NO: 26), lv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to SNIFP polypeptide (SEQ ID NO: 27), lvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iFP2.0 polypeptide (SEQ ID NO: 28), lvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iRFP713 polypeptide (SEQ ID NO: 29), lviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to iFP1.4 polypeptide (SEQ ID NO: 30), lix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mIFP polypeptide (SEQ ID NO: 31), lx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to miRFP709 polypeptide (SEQ ID NO: 32), lxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to miRFP polypeptide (SEQ ID NO: 33), lxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to M35NA polypeptide (SEQ ID NO: 34), lxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to smURFP polypeptide (SEQ ID NO: 35), lxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to TDsmURFP polypeptide (SEQ ID NO: 36), lxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to LanFP2 polypeptide (SEQ ID NO: 37), lxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to HcRed-Tandem polypeptide (SEQ ID NO: 38), lxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Skylan-S polypeptide (SEQ ID NO: 39), lxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to VFP polypeptide (SEQ ID NO: 40), lxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to GFPxm163 polypeptide (SEQ ID NO: 41), lxx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to PlamGFP polypeptide (SEQ ID NO: 42), lxxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to sarcGFP polypeptide (SEQ ID NO: 43), lxxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to psamCFP polypeptide (SEQ ID NO: 44), lxxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to GFPxm18 polypeptide (SEQ ID NO: 45), lxxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Gamillus 0.2 polypeptide (SEQ ID NO: 46), lxxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eGFP polypeptide (SEQ ID NO: 47), lxxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eYFP polypeptide (SEQ ID NO: 48), lxxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to Venus polypeptide (SEQ ID NO: 49), lxxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mOrange2 polypeptide (SEQ ID NO: 50), lxxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mCherry polypeptide (SEQ ID NO: 51), lxxx) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mTagBFP polypeptide (SEQ ID NO: 52), lxxxi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to ZsGreen polypeptide (SEQ ID NO: 53), lxxxii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to YPet polypeptide (SEQ ID NO: 54), lxxxiii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to mCitrine polypeptide (SEQ ID NO: 55), lxxxiv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to CFP polypeptide (SEQ ID NO: 56), lxxxv) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to eCFP polypeptide (SEQ ID NO: 57), lxxxvi) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to GFP polypeptide (SEQ ID NO: 58), lxxxvii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the iRFP720 polypeptide (SEQ ID NO: 59), lxxxviii) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the tdTomato polypeptide (SEQ ID NO: 60), lxxxix) a fluorescent polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the sfGFP polypeptide (SEQ ID NO: 61), xc) a fluorescent fragment of any one of (i)-(lxxxix).

69. The method of any one of the preceding items, wherein said tdTomato polypeptide (SEQ ID NO: 1) is detectable in the SWIR spectrum (e.g., by the means of a longpass filter configured to isolate the emission electromagnetic radiation of said tdTomato polypeptide with a wavelength greater than 1000 nm).

70. The method of any one of the preceding items, wherein said tdTomato polypeptide (SEQ ID NO: 1) is excitable at a wavelength of about 565 nm.

71. The method of any one of the preceding items, wherein said fluorescent probe comprises two or more different fluorescent polypeptides, preferably said two or more different fluorescent polypeptides are according any one of the preceding items.

72. The method of any one of the preceding items, wherein said method is the method for multiplexed and/or multicolor imaging of said biological sample.

73. The method for multiplexed and/or multicolor imaging of the biological sample of any one of the preceding items, comprising:

i) exposing the portion of said biological sample (e.g., a portion of said tissue) comprising a fluorescent probe to a suitable excitation source of the fluorescent probe, wherein the fluorescent probe comprises a fluorescent polypeptide; wherein said suitable excitation source is configured to provide a first light pulse/s (e.g., an excitation light pulse/s), wherein said first light pulse/s having a first wavelength in order to excite a first fluorescent polypeptide in the portion of said biological sample;

ii) exposing the portion of said biological sample to at least a second light pulse/s (e.g., a second excitation light pulse/s) having a second wavelength, which is different from the first wavelength in order to excite the second fluorescent polypeptide in the portion of said biological sample;

wherein the first light pulse/s (e.g., the first excitation light pulse/s) and the second (and/or subsequent) light pulse/s (e.g. the second excitation light pulse/s) are provided sequentially;

iii) detecting the tail portion of the light emitted by the first and the second fluorescent polypeptides in the portion of said biological sample by an imaging device, wherein the peak emission wavelength of at least one polypeptide in the portion of said biological sample lies outside of the detection range of the imaging device, the detection process including:

aa) switching the imaging device, in a sequential manner, between a first configuration during which the imaging device is responsive to a first electromagnetic radiation and a second configuration during which the imaging device is responsive to a second electromagnetic radiation, wherein said first and second electromagnetic radiations are not identical; wherein the switching of the first configuration is triggered by the provision of the light pulse.

74. The method according to any one of preceding items, further comprising: providing an optical filter in the optical path between the portion of said biological sample and the imaging device, the optical filter being configured to block the first excitation light and the second excitation light.

75. The method according to any one of preceding items, wherein the optical filter is configured as a longpass or bandpass filter with a cut-on wavelength in the micrometer range.

76. The method according to any one of preceding items, wherein the detection range of the imaging device lies in the micrometer range, preferably in the short-wave infrared (SWIR) range.

77. The method according to any one of preceding items, wherein the first and the second excitation light pulses are provided at the same rate or at the different rate.

78. The method according to any one of preceding items, wherein the pulse length of the first and second excitation light pulses is 10 ms or shorter.

79. The method according to any one of preceding items, wherein the duty cycle of the first and second pulses is 1% or less.

80. The method according to any one of preceding items, wherein the first excitation light pulse/s and the second excitation light pulse/s impinge on the portion of said biological sample from the same spatial direction.

81. The method according to any one of preceding items, wherein the first excitation light pulse/s and the second excitation light pulse/s impinge on the portion of said biological sample from different spatial directions.

82. The method according to any one of preceding items, as long as dependent on item 70, wherein the peak emission wavelength of at least one of the dyes lies below the cut-on wavelength of the longpass filter.

83. The method according to any one of preceding items, wherein for any wavelength within the detection range of the imaging device the emission intensity of at least one of the dyes amounts to 1% or less, preferably to 0.1% or less, of the peak emission intensity of the respective dye.

84. The method according to any one of preceding items, wherein the switching of the device into the first configuration is triggered by the provision of the light pulse/s such that the imaging device is switched into the first configuration simultaneously with or within 2 microseconds after the emission of any one of the first and second excitation light pulse/s.

85. The method according to any one of preceding items, wherein said method: i) does not comprise a moving and/or switching an optical filter or an array of optical filters; or ii) comprising providing only one optical filter.
86. The method according to any one of preceding items, wherein said method is one or more of the following methods:
    - i) an in vivo, ex vivo and/or in vitro method (e.g., a non-invasive method);
    - ii) a diagnostic, therapeutic, surgical (e.g., intraoperative imaging, fluorescence guided surgery) and/or screening method (e.g., management and treatment of voice disorders);
    - iii) a tissue engineering and/or transplantation method;
    - iv) a three-dimensional (3D) bioprinting method;
    - v) a real-time imaging method (e.g., real-time multiplexed imaging in non-transparent animals);
    - vi) a High-Dynamic-Range (HDR) imaging method, preferably HDR imaging method of biological structures in SWIR;
    - vii) a fluorescence imaging method;
    - viii) a multicolor real-time image acquisition method;
    - ix) a method for reduction of melanin absorption in the SWIR (e.g., as described in the examples section herein);
    - x) a method fora non-invasive imaging of tissues and/or organisms (e.g., with or without markers such as fluorescent proteins or dyes) in the presence of melanin (e.g., as described in the examples section herein.
87. The method of any one of the preceding items, further comprising determining a condition of a subject based on the detected portion of the fluorescent signal.
88. The method of any one of the preceding items, wherein the condition of a subject includes cirrhotic liver disease.
89. The method of any one of the preceding items, further comprising administering a therapeutic amount of the fluorescent probe.

EXAMPLES OF THE INVENTION

The imaging system was assembled according to FIG. 2, Table 1 (e.g., a component of the system of the present invention) and Table 2 and exemplary non-limiting specifications as described herein above.

Example 1: High-Dynamic Range (HDR) Image Acquisition in SWIR

Due to reduced photon scattering in tissues and distinguished optical properties of biological-structures in SWIR, the florescence imaging in SWIR range enables observation of complex biological structures. The clarity and detail of the acquired image data are largely constrained by dynamic range limitations of digital imaging. In visible-range digital imaging, HDR imaging methods are employed to increase dynamic range of the acquired image data to improve image detail. Construction of HDR image is performed by combining multiple images obtained with varied exposure times and estimating relative illumination values for each pixel.

Technical Challenge

Applying HDR imaging methods in SWIR imaging is challenged by higher noise levels in SWIR detectors. The cumulative noise in SWIR detectors are combination of read noise, dark-current and random noise. The dark-current noise increases with the operating-temperature of detector. Varied exposure time settings in detector changes the detector operating temperature due to the Ohmic effects in its electronics. Hence, the cumulative noise floor in most commercial SWIR detectors is not identical with varied exposure settings. This varies the achievable dynamic range in each image acquired for HDR image construction. Therefore, mapping functions of conventional HDR image construction methods cannot be extended linearly, challenging the HDR imaging in SWIR range.

Solution Using the Developed Imaging System

Alternative, yet equivalent HDR image data can be generated by employing a controllable light source and constant detector exposure setting. The developed system (depicted in FIG. 2) can acquire HDR source images with constant detector exposure time setting and varying light emission durations of constant intensity. The acquired images with different light exposure duration are then combined to construct HDR images by adopting HDR image generation methods used in the visible-range digital photography. The SWIR illuminated HDR images can represent a greater range of brightness and contrast levels than that can be achieved with single image with constant exposures. This enables more detailed observation of target fluorophores and biological structures in SWIR spectrum.

Demonstration

Figure 6:
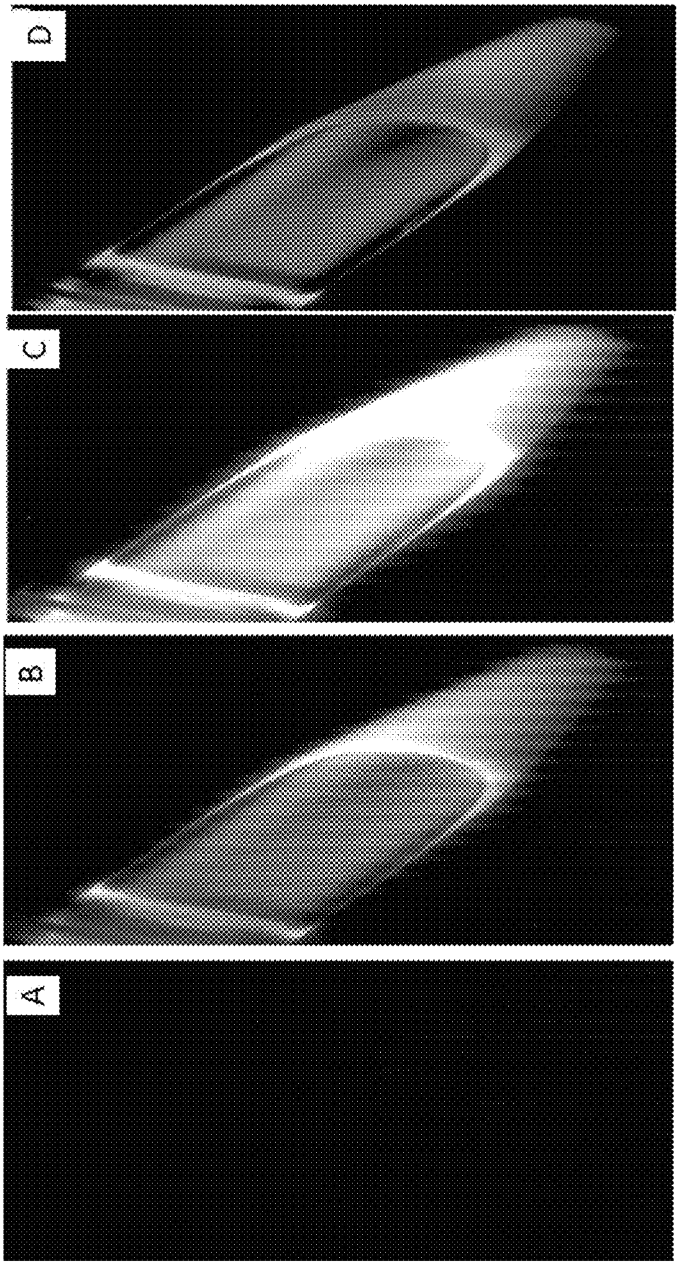
FIG. 6: The FIGS. 6A, 6B and 6C show images of an Indocyanine green sample acquired with constant detector exposure setting of 200 ms excited by a 785 nm wavelength light source. With constant light intensity, they are acquired for 10 ms, 69 ms and 148 ms light pulse durations respectively. The FIG. 6D shows the processed SWIR HDR image.

The FIGS. 6A, 6B and 6C show images of an Indocyanine green sample acquired with constant detector exposure setting of 200 ms excited by a 785 nm wavelength light source. With constant light intensity, they are acquired for 10 ms, 69 ms and 148 ms light pulse durations respectively. The FIG. 6D shows the processed SWIR HDR image.

Excitation-Side Optics:

Light Source (785 nm laser)→Collimator→Mirror→1100 nm Short-pass Filter→Engineered Diffuser→Sample. The arrows represent the light path. Accordingly, the light path has been set up as follows: from Light Source (785 nm laser) to Collimator to Mirror to 1100 nm Short-pass Filter to Engineered Diffuser to Sample.

Emission-Side Optics:

Sample→3×f=500 mm C-Coated lenses→Silver Mirror→1000 nm Long-pass Filter→2×f=200 mm C-coated lenses→InGaAs Detector. The arrows represent the light path. Accordingly, the light path has been set up as follows: from Sample to 3×f=500 mm C-Coated lenses to Silver Mirror to 1000 nm Long-pass Filter to 2×f=200 mm C-coated lenses to InGaAs Detector.

Detector: Allied Vision Goldeye G032 GigE TEC2,

Trigger Controller: Version 1.5 (FIG. 4).

Sample: Indocyanine green dissolved in ethanol (1 mg/ml).

Conclusion: the construction of high dynamic range images (HDRIs) can be performed by combining multiple images obtained with different exposures and estimating the irradiance value for each pixel. This is a method for achieving HDRI acquisition with visible range detectors. By employing a controllable current source, the designed system can acquire images with constant detector exposures and varying light source emission duration with constant intensity. The acquired images with different light exposure durations, then combined to construct high dynamic range images. Such SWIR illuminated HDR images can represent a greater range of brightness and contrast levels than that can be achieved with single image with constant exposure enables more detailed observation of biological structures.

Example 2: Multicolor Real-Time Image Acquisition in SWIR

Real-time acquisition of multicolor image data may open frontiers of biological investigation to study living organisms and develop medical diagnostics. Multicolor traces can be dynamically labelled to identify bio-structures and/or states of a biological sample. Combined with emerging technologies such as machine vision, learning and embedded robotics, the dynamic labels could enable deeper understanding of bio-chemical processes in living organisms and targeted and/or autonomous development of medical diagnosis. The developed system is capable of performing real-time, multicolor fluorescence image acquisitions in short-wave infrared. Some of the direct application of this methodology enabled by the developed system are as follows:

Imaging of Awake Mice: Ability to image an awake mouse in real-time multicolor enables to study the effects of anesthesia on the physiology of mice (cardiovascular function, respiratory function, thermoregulation, metabolism, central nervous system functions). And the ability to acquire such image data in SWIR range of electro-magnetic spectrum adds the advantages of reduced tissue scattering and increased image contrast.

Intestinal Mobility Tracking: Studying the intestinal mobility and its behavior allows monitoring of disease and the effect of pharmaceutic agents. The intestine motion could be affected by the irritable bowel syndrome, inflammatory bowel disease or chronic intestinal pseudo-obstruction. Furthermore, studying intestinal mobility in premature infants might/could allow diagnosing the condition necrotizing enterocolitis earlier and without use of ionizing radiation.

Lymphatic Imaging: Imaging the lymphatic system is useful for surgical imaging for dissection, diagnosis, studying and monitoring of lymphatic diseases such as lymphederna and to assess the tissue rejection in animal models.

Technical Challenge

Existing technologies to realize real-time, multicolor imaging either use multiple detector-light units or mechanically coupled rotating filter components. Use of multiple detector units significantly increases the system cost. And introducing rotating optical filter components impact or change the optical characteristics between the acquired channels.

Solution Using the Developed Imaging System

The developed system performs sequential triggering of the excitation sources and collects image data using a single detector unit. This provides the unique opportunity to image the physiology of awake mice with multiplexed detection in video rate (~30 FPS) without any introduced optical artifacts in the acquired image data. The color channels can be configured by pre-determined combination of excitation sources and VIS/NIR/SWIR probes. Independent controlling of multiple light sources and detection unit eliminates the need for moving parts in the imaging system and increases the system life-time and reliability.

Demonstration I: Imaging of Awake Mouse

The FIGS. 7A, 7B and 7C show merged frames of the awake mouse in motion imaged in real-time with two color spectra of 6 ms detector exposure duration. In this configuration, a frame rate of 50 fps is achieved with the developed system.

Excitation-Side Optics:

Light Sources (785 nm laser & 1064 nm laser sequentially triggered, Pulse Width=8 ms)→Collimator→Mirror→1100 nm Short-pass Filter→Engineered Diffuser→Sample. The arrows represent the light path. Accordingly, the light path has been set up as follows: from Light Sources (785 nm laser & 1064 nm laser sequentially triggered, Pulse Width=8 ms) to Collimator to Mirror to 1100 nm Short-pass Filter to Engineered Diffuser to Sample.

Emission-Side Optics:

Sample→1×f=750 mm C-Coated lenses→Silver Mirror→1100 nm Long-pass Filter→2×f=200 mm C-coated lenses→InGaAs Detector. The arrows represent the light path. Accordingly, the light path has been set up as follows: from Sample to 1×f=750 mm C-Coated lenses to Silver Mirror to 1100 nm Long-pass Filter to 2×f=200 mm C-coated lenses to InGaAs Detector.

Detector: Allied Vision Goldeye G032 GigE TEC2,

Trigger Controller: Version 1.5 (FIG. 4).

Sample: ICG (aqueous, 13 nmol intravenously) and Julo7 (micelles, 35 nmol intravenously).

Demonstration II: Intestinal Mobility Tracking

The FIGS. 8A, 8B and 8C show merged frames representing peristatic motions of a narcotized mouse in real-time two-color spectrum. With detector exposure time of 6 ms, a compound frame rate of 62 fps is achieved with the developed system. The ability to image with two colors removes the necessity to draw overlays of SWIR information on a visible or NIR range image.

Excitation-Side Optics:

Light Sources (785 nm laser & 1064 nm laser sequentially triggered, Pulse Width=8 ms)→Collimator→Mirror→1100 nm Short-pass Filter→Engineered Diffuser→Sample. The arrows represent the light path. Accordingly, the light path has been set up as follows: from Light Sources (785 nm laser & 1064 nm laser sequentially triggered, Pulse Width=8 ms) to Collimator to Mirror to 1100 nm Short-pass Filter to Engineered Diffuser to Sample.

Emission-Side Optics:

Sample→1×f=750 mm C-Coated lenses→Silver Mirror→1100 nm Long-pass Filter→2×f=200 mm C-coated lenses→InGaAs Detector. The arrows represent the light path. Accordingly, the light path has been set up as follows: from Sample to 1×f=750 mm C-Coated lenses to Silver Mirror to 1100 nm Long-pass Filter to 2×f=200 mm C-coated lenses to InGaAs Detector.

Detector: Allied Vision Goldeye G032 GigE TEC2,

Trigger Controller: Version 1.5 (FIG. 4).

Sample: ICG (aqueous, 13 nmol intravenously) and Julo7 (micelles, 35 nmol intravenously).

Demonstration III: Lymphatic Imaging

The FIGS. 9A, 9B and 9C show merged frames representing the lymphatic system of a narcotized mouse in two-color real-time acquisition. With detector exposure time of 20 ms, a frame rate of 21 fps is achieved with the developed system. For this demonstration, ICG has been injected intradermally into footpads and the base tail. After 30 min, ICG has been observed to be efficiently conducted through the lymphatic vessels. Then, Julo 7 micelles have been injected intravenously. The lymphatic functional imaging is later enhanced by the assignment of two distinct colors.

Excitation-Side Optics:

Light Source (785 nm laser & 1064 nm laser sequentially triggered, pulse length=21 ms)→Collimator→Mirror→1100 nm Short-pass Filter→Engineered Diffuser→Sample. The arrows represent the light path. Accordingly, the light path has been set up as follows: from Light Source (785 nm laser & 1064 nm laser sequentially triggered, pulse length=21 ms) to Collimator to Mirror to 1100 nm Short-pass Filter to Engineered Diffuser to Sample.

Emission-Side Optics:

Sample→3×f=500 mm C-Coated lenses→Silver Mirror→1000 nm Long-pass Filter→2×f=200 mm C-coated lenses→InGaAs Detector. The arrows represent the light path. Accordingly, the light path has been set up as follows: from Sample to 3×f=500 mm C-Coated lenses to Silver Mirror to 1000 nm Long-pass Filter to 2×f=200 mm C-coated lenses to InGaAs Detector.

Detector: Allied Vision Goldeye G032 GigE TEC2,

Trigger Controller: Version 1.5 (FIG. 4).

Sample: ICG (aqueous, 13 nmol intradermally [footpads and base of tail]) and Julo7 (micelles, 70 nmol intravenously).

Figure 7:
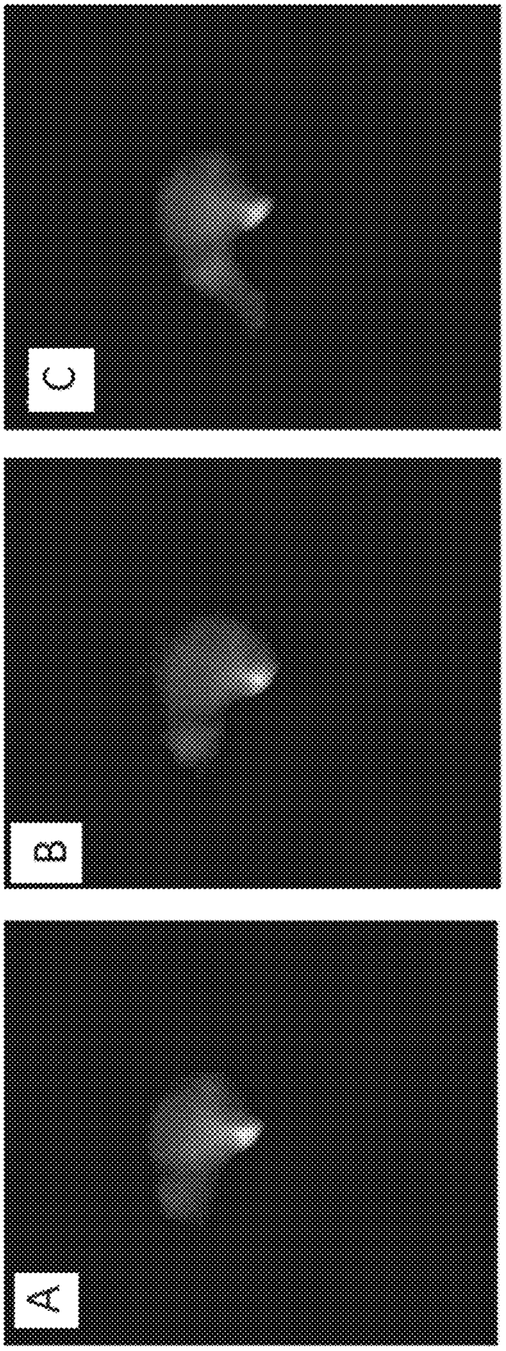
FIG. 7: Multicolor Real-time Image Acquisition in SWIR. The FIGS. 7A, 7B and 7C show merged frames of the awake mouse in motion imaged in real-time with two color spectra of 6 ms detector exposure duration. In this configuration, a frame rate of 50 fps is achieved with the developed system.
Figure 8:
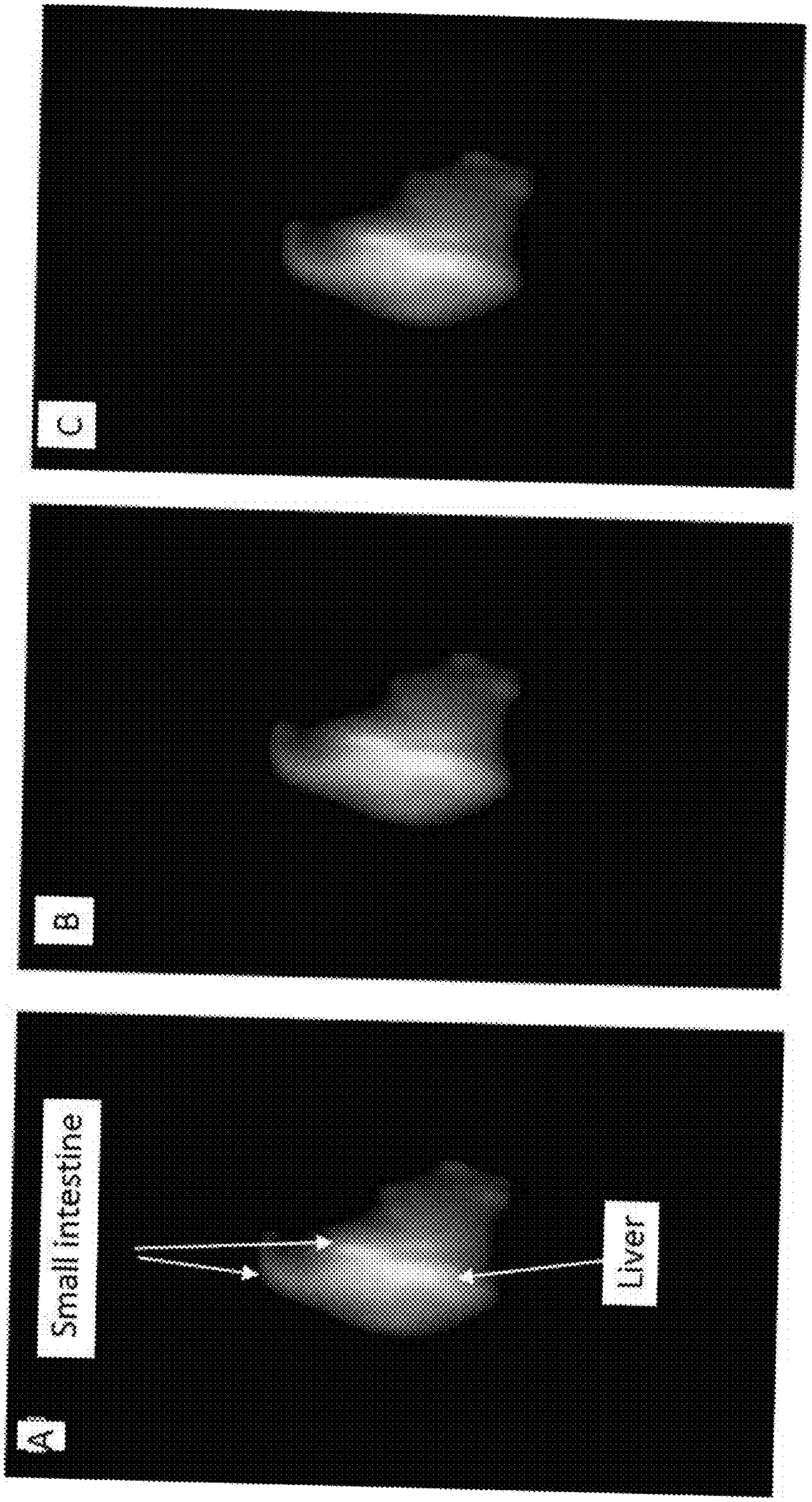
FIG. 8: Multicolor Real-time Image Acquisition in SWIR. The FIGS. 8A, 8B and 8C show merged frames representing peristatic motions of a narcotized mouse in real-time two-color spectrum. With detector exposure time of 6 ms, a compound frame rate of 50 fps is achieved with the developed system. The ability to image with two colors removes the necessity to draw overlays of SWIR information on a visible range image.
Figure 9:
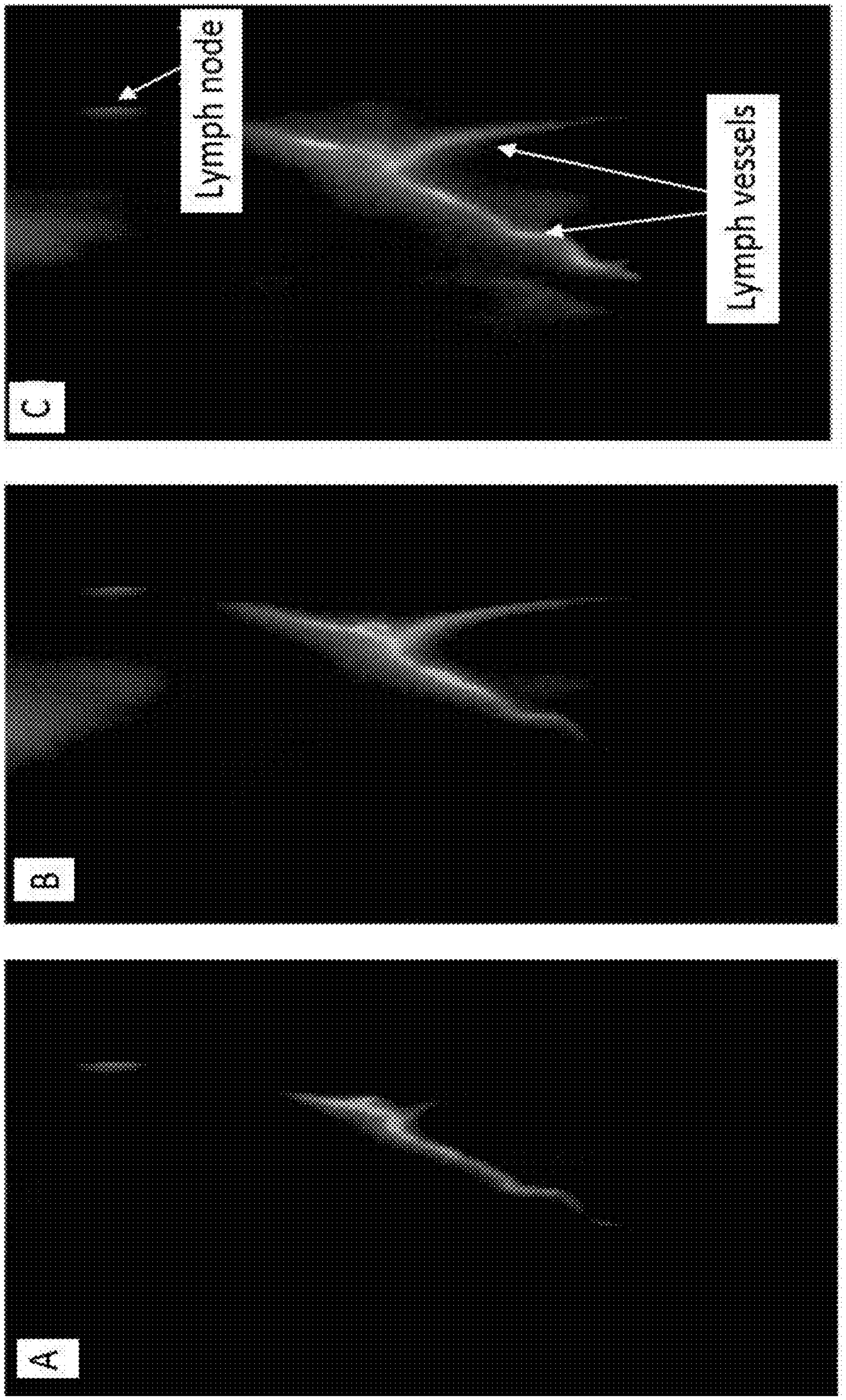
FIG. 9: Multicolor Real-time Image Acquisition in SWIR. The FIGS. 9A, 9B and 9C show merged frames representing the lymphatic system of a narcotized mouse in two-color real-time acquisition. With detector exposure time of 20 ms, a frame rate of 21 fps is achieved with the developed system. For this demonstration, ICG has been injected intradermally into footpads and the base tail. After 40 min, ICG has been observed to be efficiently conducted through the lymphatic vessels. Then, Julo7 micelles have been injected intravenously. The lymphatic functional imaging is later enhanced by the assignment of two distinct colors.

Conclusion: by use of targeted SWIR fluorophores in different biological structures and/or states, the multicolor real-time image data acquisition can be achieved by the presented example (e.g., FIGS. 7, 8 and 9). The multispectral SWIR excitation sources can be switched sequentially and with clear temporal isolation to excite the targeted SWIR probes embedded in the biological sample. Each excitation would then correspond to SWIR emission stimulated by the fluorophores. This emission is then captured by the SWIR detector to form required image data. Using the sequential excitation information, acquired image data can be isolated and rendered in multicolor image information to produce real-time multicolor image data of the target biological subject.

Example 3: Dark-Current Noise-Less SWIR Imaging

A general technical limitation of SWIR imaging is the detector introduced noise in the acquired image data. It greatly reduces the dynamic range of the detector in the long exposure durations due to increased dark-current. Though there exist solutions that can to some extent overcome these noise artifacts, such technologies often come at higher associated cost. A cost-effective solution is to acquire SWIR image in shorter exposure-times where the dark-current noises are significantly less than the read-noise of the detectors. This can be realized by the presented embodiment by producing high-intensity short-duration excitations by the controlled light sources. By keeping the average power within the safety limits, the biological structure can be imaged in short-exposure duration with high-sensitivity of optical signal.

Example 4: Three-Dimensional Imaging in SWIR

By acquiring/illuminating from different angles one can create 3D real-time multicolor images. Which provides the opportunity to assess for example the behavior and physiology in awake and unrestrained animals without motion artefacts which are associated with longer exposure times.

Example 5: Strobo-Effected Image Acquisition in SWIR and Stroboscopy Analysis in SWIR Stroboscopic imaging of vocal fold vibratory function during phonation used to derive diagnostic, therapeutic, and surgical decisions during the management and treatment of voice disorders. While newer laryngeal imaging technologies such as high-speed video-endoscopy (HSV), magnetic resonance imaging, and optical coherence tomography continue to enhance the ability to better define and quantify complex phonatory mechanisms, the cost effectiveness, ease of use, and synchronized audio and visual feedback provided by video-stroboscopic assessment maintain its predominant clinical role in laryngeal imaging. The application of video stroboscopy can be performed in the SWIR spectrum with the developed system.

Technical Challenge

Limitations on sampling rate often prevent stroboscopic imaging from capturing cycle-to-cycle details of vocal fold vibratory characteristics. Therefore, achieving standard video frame rates in multiple spectrum is crucial to synthesize a SWIR stroboscopy. Due to the techno-economic constraints in the SWIR detector development, a video-rate multi-spectral SWIR imaging device is not available for commercial use preventing the extension of video-stroboscopic assessments in short wave infrared.

Solution Using the Developed Imaging System

As explained in the application example 2 and application example 7, the developed system can perform sequential triggering of excitation sources and collect image data using a single detector unit. Hence the basis to acquire images of a same subject in several distinct SWIR spectra in video rate is achieved. By combining the acquired images of the same subject in distinct SWIR spectrum, multicolor movies and the video-stroboscopic assessment can be synthesized in the post processing.

Conclusion: the high-speed triggering and acquisition allows the device to act as a stroboscope, allowing to see continuous moving objects as stationary. Imaging in this way in the SWIR might allow differentiation of fluid filled pathological structures (e.g., abscesses) and non fluid filled structures (e.g., cysts).

Example 6: Emission & Excitation Fingerprint

Acquiring images in different wavelength bands allows the creation of an image that provides a spectrum of the specimen at every pixel location throughout the lateral dimensions. Thus, the image stack can be considered as a collection of different wavelengths at each pixel location. Each fluorophore has a unique spectral signature or emission fingerprint that can be determined independently and used to assign the proper contribution from that probe to individual pixels. The linear unmixing is the generation of distinct emission fingerprints for each fluorophore used in the specimen (or excitation fingerprints if excitation rather than emission spectra were employed to generate the stacks (3)). This allows for separation of autofluorescence background and emission of a label of interest.

Example 7: Real-Time Reflectance Imaging in Short-Wave Infrared

The varying SWIR reflectance and/or absorbance properties of physical matters can be explored using the developed system. Although certain organic and inorganic matters possess indistinguishable properties in the visible spectrum, reflective multicolor imaging in the SWIR spectrum can provide fine details of such matters due to the distinct properties of considered matters in this SWIR range. For example, water with protium hydrogen is an absorbent in certain SWIR range whereas the water with deuterium hydrogen is not. Such difference in the optical properties of different matters can be exploited to construct a multicolor SWIR imaging in real-time to study the motion state and/or structure of the physical samples.

Technical Challenge

Although there exist mature CMOS detectors for multi spectral visible range imaging applications, available SWIR detector technologies (such as InGaAs sensors, MCT sensors etc.) are not capable of performing a direct on-chip real-time multicolor image acquisition due to techno-economic constraints.

Solution Using the Developed Imaging System

As explained in the application example 2 above, the developed system can perform sequential triggering of the excitation sources and collect image data using a single SWIR reflection detector unit. This provides the basis to real-time acquire images of a same subject in several distinct SWIR spectra. Same as in example 2, the color channels can be configured by pre-determined combination of excitation sources. By combining the acquired images of the same subject in distinct SWIR spectrum, multicolor movies can be synthesized in the post processing. The developed system can reach a nominal frame rate of 100 fps shared by two-three color channels, enabling structural changes/motion detection in biological samples.

Example 8: Cost-Effective SWIR Imaging Using Non-Scientific Cameras

Due to the low bandgap of InGaAs material, InGaAs FPA cameras have much higher dark current than Si-CCD cameras. Therefore, it is absolutely critical to minimize InGaAs FPA cameras' dark noise with embedded cooling systems. Scientific InGaAs FPA cameras often use thermoelectric cooling and vacuum technology to cool the camera sensors well below the ambient temperature to achieve the lowest possible dark noise. Use of such embedded cooling systems significantly increases the cost of the camera and its form factor.

Technical Challenge

InGaAs FPAs are dark-noise-limited devices. Deep cooling well below the ambient temperature is required to reduce dark charge and preserve the signal-to-noise ratios needed for scientific applications. However, cooling the sensor below the ambient temperature would precipitate the humid air on the sensor chip. This could lead to reduced camera performance and shorten its lifetime. Commercially available scientific grade InGaAs detector camera systems employ vacuum chamber and liquid nitrogen-based cooling systems to cool the camera sensors without in the absence of humid air. This leads to larger camera form-factor and higher system cost of the detector device.

Solution Using the Developed Imaging System

The need for vacuum based cooling systems in non-scientific InGaAs camera can be eliminated by preserving lower detector exposure time and relatively increasing the intensity of the electromagnetic excitation. The average flux intensity of NIR/SWIR spectrum can be controlled within the limits specified for non-destructive tissue imaging by the SWIR developed imaging system. Here, the synchronized excitation sources provide enough flux intensity to acquire a SWIR image with short-pulsed excitations. By appropriately configuring the time resolution of the system, the average flux density can be maintained within the approved levels. Therefore, effects of dark current can be avoided and small form-factor lower-cost non-scientific cameras can be used for SWIR image acquisitions. This would vastly simplify the design of medical diagnostic instruments and reduce their production costs.

Example 9: Real-Time Multiplexed Imaging in Non-Transparent Animals

Figure 10:
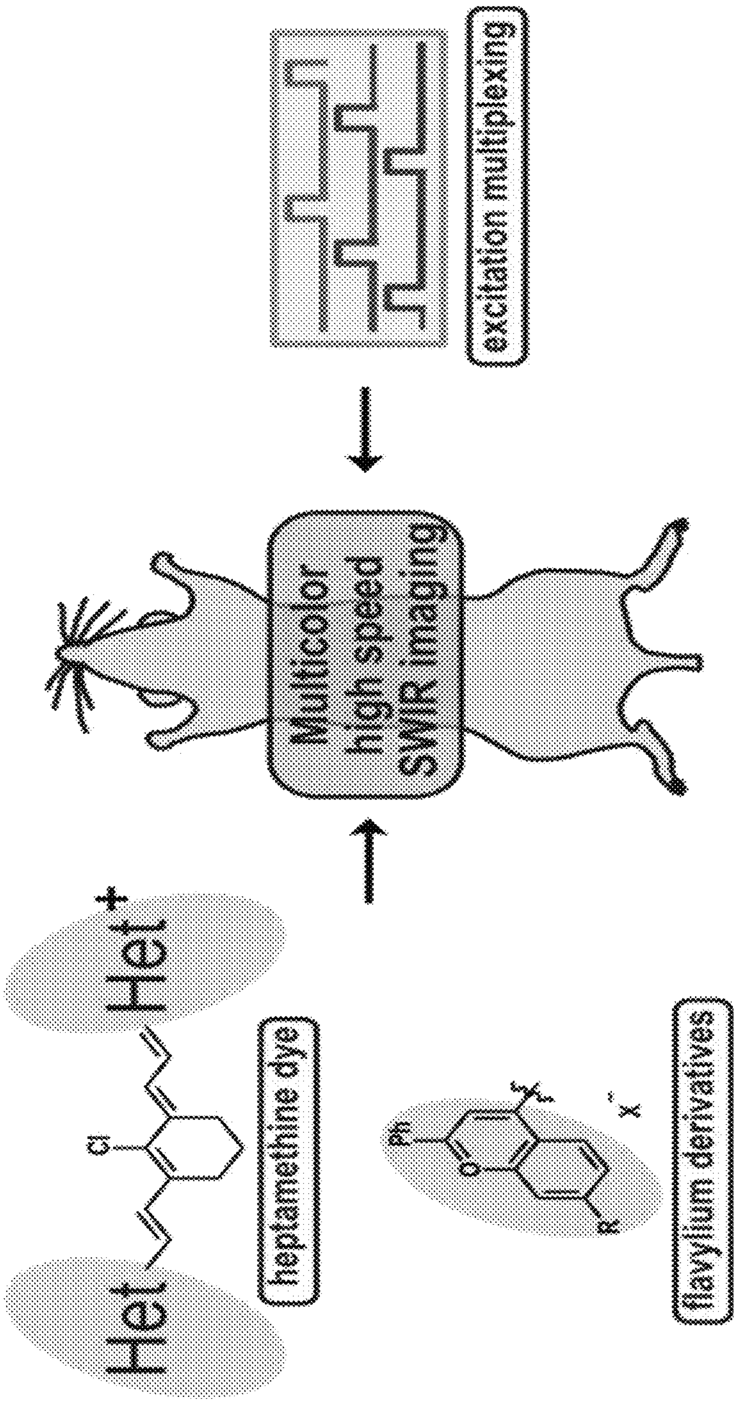
FIG. 10: Approach to achieve multicolor whole animal imaging in high spatial and temporal resolution by parallel advances in flavylium heptamethine fluorophore derivatives and whole animal excitation-multiplexing technologies.

The following approach has been employed to achieve multicolor whole animal imaging in high spatial and temporal resolution by parallel advances in polymethine fluorophore derivatives and whole animal excitation-multiplexing technologies (FIG. 10).

Thus far, non-invasive multiplexed experiments in animals have been limited to excitation of multiple probes with common wavelengths. Differentiation between contrast agents is achieved by either emission filter combinations to section spectral regions of detection, or by spectral unmixing. Approaches using multichannel single-detector imaging have prevented multiplexed fast acquisition to date as the filters employed must be changed for each channel. Additionally, signal is often limited in these methods by suboptimal excitation of multiple probes with a single wavelength, and by collection in narrow windows of the electromagnetic spectrum. Efficient excitation and economic photon detection are especially critical for the SWIR region where quantum yields are often below 1%. Finally, as the contrast and resolution one can obtain varies throughout the NIR and SWIR, this approach results in different resolutions for each channel.

An alternate method relies on differences in fluorophore excitation intensities instead of emission properties. Excitation-multiplexing enables a single "color-blind" detection source to be used, while excitation sources are modulated. Initially deemed pulsed multiline excitation in the development of low concentration DNA sequencing, high signal is favored by tuning excitation to the absorption maxima of each fluorophore and collecting over a larger emission regime. Temporal separation negates the need for spectral unmixing to determine dye identities. Variations on excitation-multiplexed methods including frequency-, as opposed to time-separated methods have been developed for fluorescence lifetime microscopy (FLIM), and super-resolution methods.

To accomplish real-time multiplexed imaging in non-transparent animals, a method is needed in which 1) SWIR detection is employed for high contrast, resolution, and penetration depth; 2) fluorophores are excited at their absorbance maximum and all SWIR photons are collected to achieve ample signal and; 3) detection of each channel can occur in tandem on the millisecond time scale. These requirements could, for example, be met by excitation-multiplexing and "color-blind" detection of custom, bright polymethine fluorophores.

Polymethine dyes, characterized by their narrow absorption and emission bands and high absorption coefficients, are a prime scaffold for excitation multiplexing. The ability to tune wavelengths of excitation and emission relies on structural changes to both the heterocycle and polymethine chain. A marque member of the polymethine dye family is indocyanine green (ICG), an FDA approved contrast agent used on-label for measuring cardiac and hepatic function and observing retinal angiography. Expanded clinical uses, including fluorescence guided surgery, are impending, and responsive probes based on the scaffold are in development. While ICG has been extensively used in NIR optical imaging, it was recently characterized to have a bright SWIR tail which can be imaged with InGaAs detection upon 785 nm excitation to obtain ~2× higher resolution images than can be obtained with NIR detection on a CCD camera.

Capitalizing on the design of the existing fluorophore Flav7 (Cosco et al., 2017), it was hypothesized that functional group changes at the 7-position on flavylium (FIG. 11) could tune the absorption and emission profiles of the re-suiting fluorophore and allow access to a set of dyes which were optimal for real-time imaging via excitation multiplexing.

Symmetric polymethine dyes are obtained through a condensation reaction with two equivalents of an activated heterocycle and a bis-aldehyde or bis-imine vinylene chain. The preparation of the 7-N,N-dimethylamino-4-methyl-flavylium heterocycle 2 employed in Flav7 synthesis, was originally reported by Yang and coworkers (FIG. 11A) (Chen et al., 2008). The route involves a low yielding Fries-rearrangement to obtain 1, followed by an unreliable and unsafe condensation reaction. Furthermore, the success of these reactions is highly dependent on the steric and electronic properties of the heterocycle, limiting derivatization of the scaffold. Thus, to obtain flavylium-based polymethine dyes with diverse functionality on the heterocycle, it was imperative to develop a more versatile synthetic route to 7-amino substituted 4-methyl flavylium derivatives.

Figure 11:
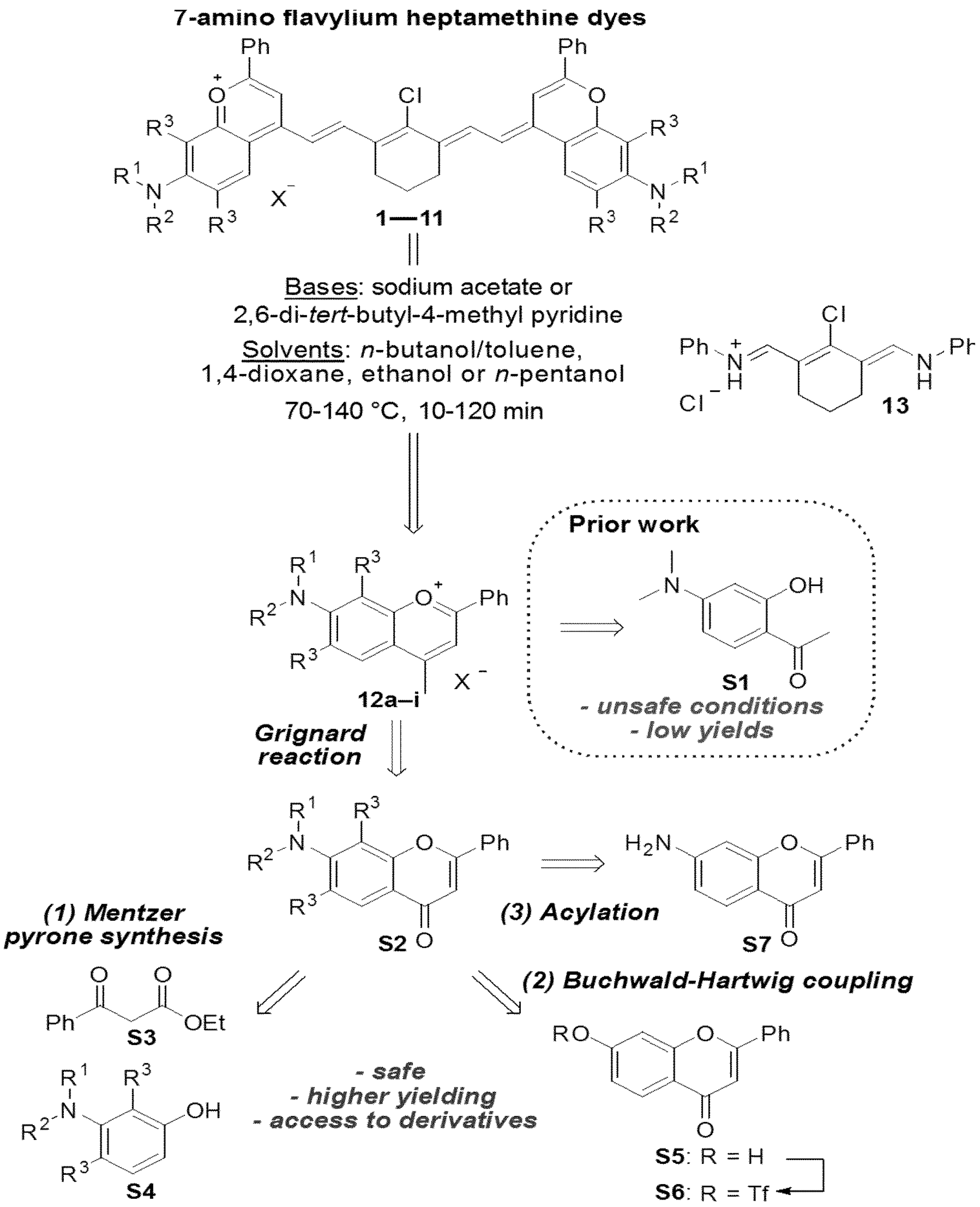
FIG. 11: Synthetic route to 7-amino flavylium heptamethine derivatives.

We envisioned that that diverse 4-methyl flavylium derivatives could be obtained from the requisite 7-substituted flavone by treatment with a methyl nucleophile and dehydration. Flavones have been common synthetic targets due to their pharmacological activity. Using three general routes to flavones: 1) Mentzer pyrone synthesis, a thermally induced condensation between a beta-keto-ester and a phenol; 2) functionalization of a commercial 7-hydroxy flavone by Buchwald-Hartwig coupling of the corresponding triflate; 3) acylation of the commercial 7-amino flavone, we were able to access a diverse set of 7-amino flavylium heterocycles (FIG. 11).

Specifically, by route 1), the alkylated amino flavones S2a-c were obtained in moderate yields, 51-55%, by subjecting a substituted 3-aminophenol (s4a-c) to ethylbenzoylacetate (53) and heating neat for 20-48 h. In route 2) aliphatic and aromatic aminoflavones s2d-h were acquired by palladium catalyzed C—N coupling reactions of triflate S6 with a variety of secondary amines in 63-83% yield. Finally, by route 3), a BOC substituted 7-aminoflavone was synthesized by treatment of 7-aminoflavone S7 with BOC-anhydride in base with catalytic dimethylaminopyridine to obtain the doubly BOC protected product S2i in 75% yield. Each flavone was subsequently converted to the corresponding 4-methyl flavylium 12a-i in moderate to good yields (39-86%) by treatment with methyl Grignard and quenching with fluoroboric acid. The fluoroboric acid gives rise to a tetrafluoroborate counterion that is retained in the final dye species, as confirmed by 19F NMR. The 7-methoxy substituted 4-methyl flavylium 12j was synthesized according to a known route.

The heptamethine dyes were synthesized by the base-promoted reaction of 4-methyl flavylium heterocycles with bis(phenylimine) 13. The conditions required for successful dye formation proved to be dependent on the heterocycle used. Thus, the solvent and base used were tailored to each heterocycle and are summarized in Table 3.

Notably, the non-nucleophilic base 2,6-di-tert-butyl-4-methylpyridine facilitated efficient polymethine formation with few signs of degradation of the dye, as monitored by UV-Vis-NIR spectrophotometry. For most heterocycles (12a-d; 12g-j), 90-100° C. was sufficient to achieve fast (10-15 min) conversion to the heptamethine. The cyclic alkyl amine heterocycles 12e and 12f required either extended time (up to 120 min), or higher temperatures (up to 140° C.) for efficient reaction conversion.

TABLE 3

Parameters of flavylium heptamethine fluorophore synthesis.

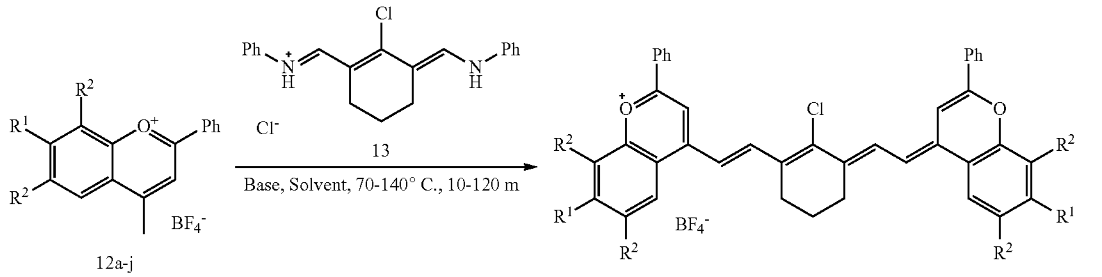

12a-j 13 1-11

| Flavylium 8 | $R^1$ | $R^2$ | base[a] | solvent | temp (° C.) | time (m) | yield # (%) | dye |
|---|---|---|---|---|---|---|---|---|
| 12a | 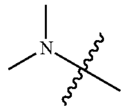 [SMILES: *N(C)C] | H | A | n-butanol/toluene | 100 | 15 | 51 | 1 |
| 12b | 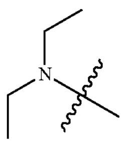 [SMILES: *N(CC)CC] | H | A | n-butanol/toluene | 100 | 10 | 40 | 2 |

TABLE 3-continued
Parameters of flavylium heptamethine fluorophore synthesis.
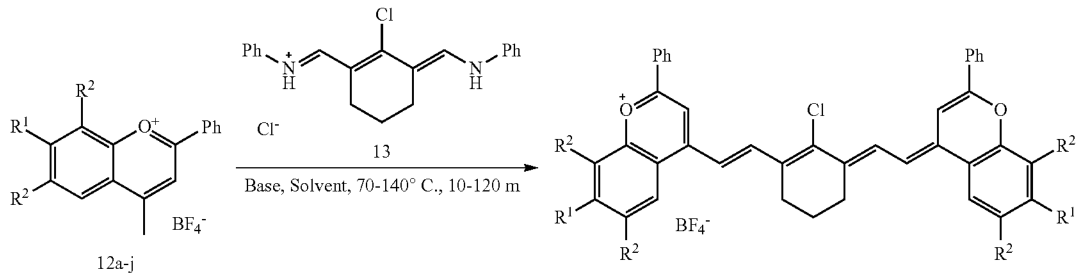
12a-j
1-11
| Flavylium 8 | $R^1$ | $R^2$ | base[a] | solvent | temp (° C.) | time (m) | yield # (%) | dye |
|---|---|---|---|---|---|---|---|---|
| 12c | 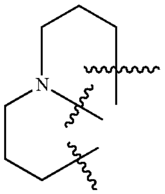 [SMILES: *CCCN(*)CCC*] | | A | ethanol | 70 | 120 | 37 | 3 |
| 12d | 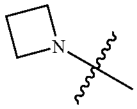 [SMILES: *N1CCC1] | H | A | n-butanol/toluene | 100 | 10 | 37 | 4 |
| 12e | 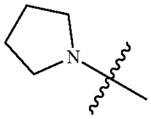 [SMILES: *N1CCCC1] | H | B | n-pentanol | 140 | 50 | 8 | 5 |
| 12f | 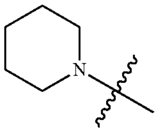 [SMILES: *N1CCCCC1] | H | B | n-butanol/toluene | 100 | 120 | 26 | 6 |
| 12g | 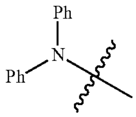 | H | B | 1,4-dioxane | 100 | 15 | 11 | 7 |
| 12h | 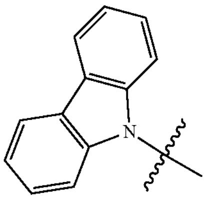 [SMILES: *n1c2ccccc2c2ccccc21] | H | B | 1,4-dioxane | 90 | 15 | 13 | 8 |
| 12i | 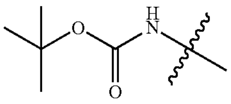 [SMILES: *NC(=O)OC(C)(C)C] | H | B | 1,4-dioxane | 95 | 15 | 33[b] | 9 |
| 12j[c] | 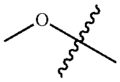 | H | B | n-butanol/toluene | 100 | 15 | 33 | 10 |
| — | 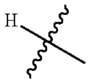 | H | B | n-butanol/toluene | 90 | 45 | 5 | 11 |

TABLE 3-continued

Parameters of flavylium heptamethine fluorophore synthesis.

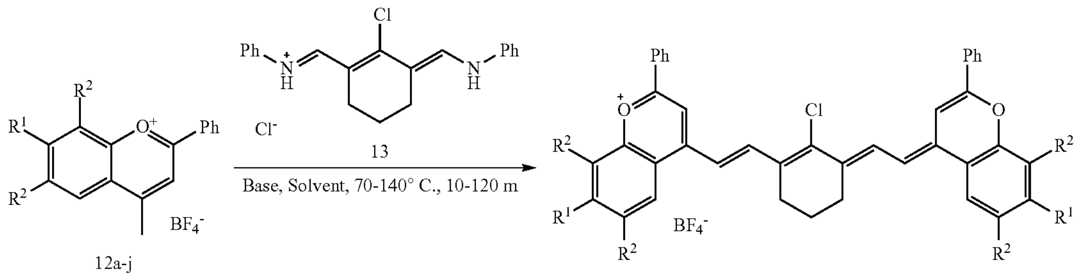

12a-j 1-11

| Flavylium 8 | $R^1$ | $R^2$ | base[a] | solvent | temp (° C.) | time (m) | yield # (%) | dye |
|---|---|---|---|---|---|---|---|---|

Figure 12:
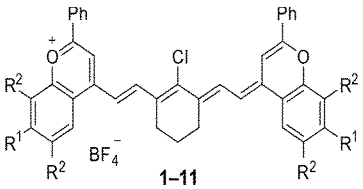
FIG. 12: Photophysical properties of flavylium polymethine fluorophores. A) Flavylium polymethine dye scaffold B) Absorption wavelength maxima visualized graphically on the electromagnetic spectrum. C) Absorption profiles of selected polymethine dyes 1, 3, 7, 9, 10 D) Emission profiles of selected polymethine dyes 1, 3, 7, 9, 10. E) Tabulated photophysical properties of heptamethine dyes.
Figure 12:
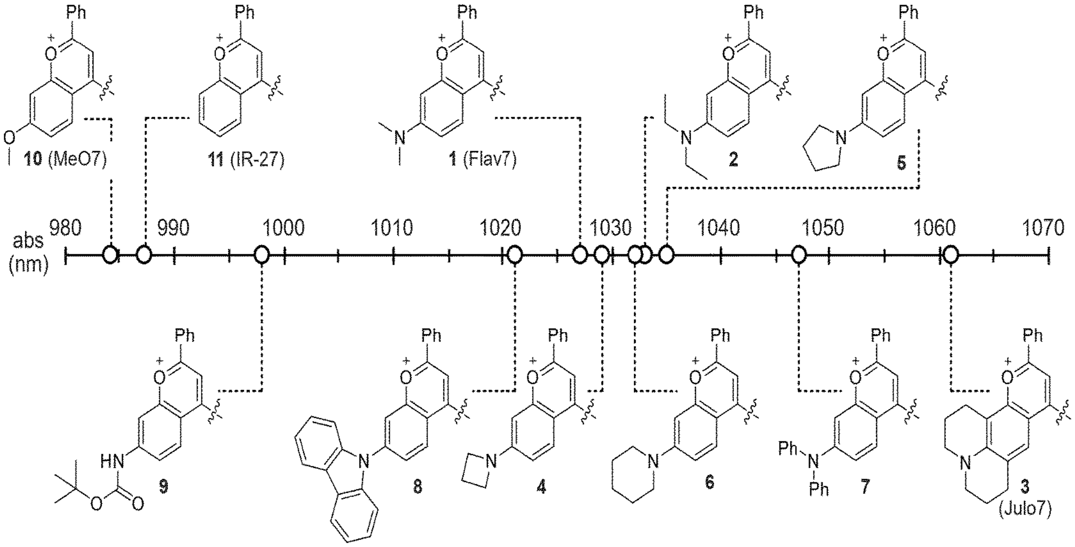
Figure 12:
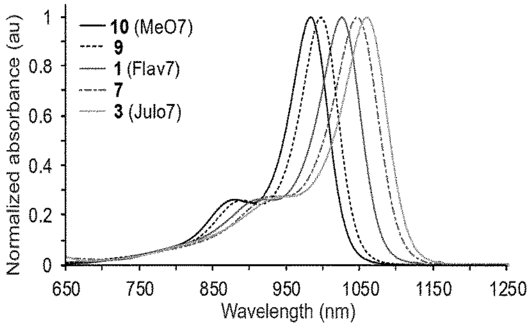
Figure 12:
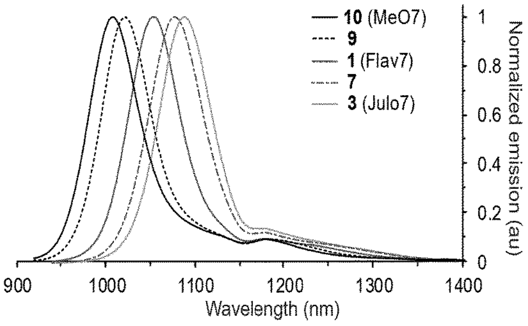

[a]base: A = sodium acetate; B = 2,6-di-tert-butyl-4-methyl pyridine
[b]yield over two steps, flavylum #i not isolated in dye synthesis
[c]counterion is $Cl^-$ We characterized the absorptive and emissive properties of 1-11 in dichloromethane and found that the flavylium heptamethine dyes accessed have absorption and emission spanning the far-NIR to SWIR regions of the electromagnetic spectrum (FIG. 12). Compared to Flav7 1, with λmax, abs=1027 nm and λmax,em=1053 nm, 9 and 10 achieved significant hypsochromic shifts. As the highest energy absorber of the series, the 7-methoxy substituted dye 10 is ~44 nm blue shifted from Flav7, with absorption at 984 nm, close to the 980 nm laser line, and emission at 1008 nm. Notably, the un-substituted flavylium dye 11, which was previously reported by Drexhage as IR-27, is ~41 nm blue shifted from Flav7 and has a lower brightness (εmax). A carbazole derivative 8, has slightly blue shifted properties. Linear and cyclic aliphatic amine substituents resulted in dyes 2, 4-6, which exhibit minor red-shifts compared to Flav7. Conversely, dyes 3 and 7 underwent substantial batho-chromic shifts compared to Flav7. The diphenylamino substituted 7 is ~23 nm red-shifted compared to Flav7, while julolidine derivative 3 is red-shifted by ~35 nm with absorption at 1061 nm and emission at 1088 nm. Due to its absorption maximum and high brightness (εmax), 3 was a promising candidate for SWIR imaging with 1064 nm excitation and was named Julo7. Plotting absorption and emission wavelengths of nine dyes in the series (omitting the aromatic derivatives 7 and 8) against the Hammett am values, resulted in a linear correlation ($R^2$=0.96). The empirical relationship of negative am values to longer absorption wavelengths indicates that the electronic donating ability of the substituent is indeed responsible for the red-shifted photophysical behavior. This increased understanding of the relationship between structural and absorption/emission wavelengths sets-up opportunities for predicting photophysical properties of the scaffold.

The absorption coefficients (ε) of the series vary from ~110,000 to ~240,000 $M^{-1}cm^{-1}$. High absorption cross sections are characteristic for many polymethine fluorophores and are essential for obtaining high-quality video-rate images in the SWIR. The fluorescence quantum yields ($\varphi_F$) (relative measurements to IR-26=0.05%) remain rather constant, in the 0.4 to 0.6% range, despite red- or blue-shifted behavior, providing a platform for intensity-matched probes. Combined, high ε and $\phi_F$ values for the SWIR result in a bright dye series: six dyes (1-5, 7, and 10) have a brightness ($\varepsilon_{max}$) 1000 $M^{-1}cm^{-1}$. High brightness, combined with varied absorption and emission wavelengths, poise the series for real-time, excitation multiplexing in the SWIR.

Figure 13:
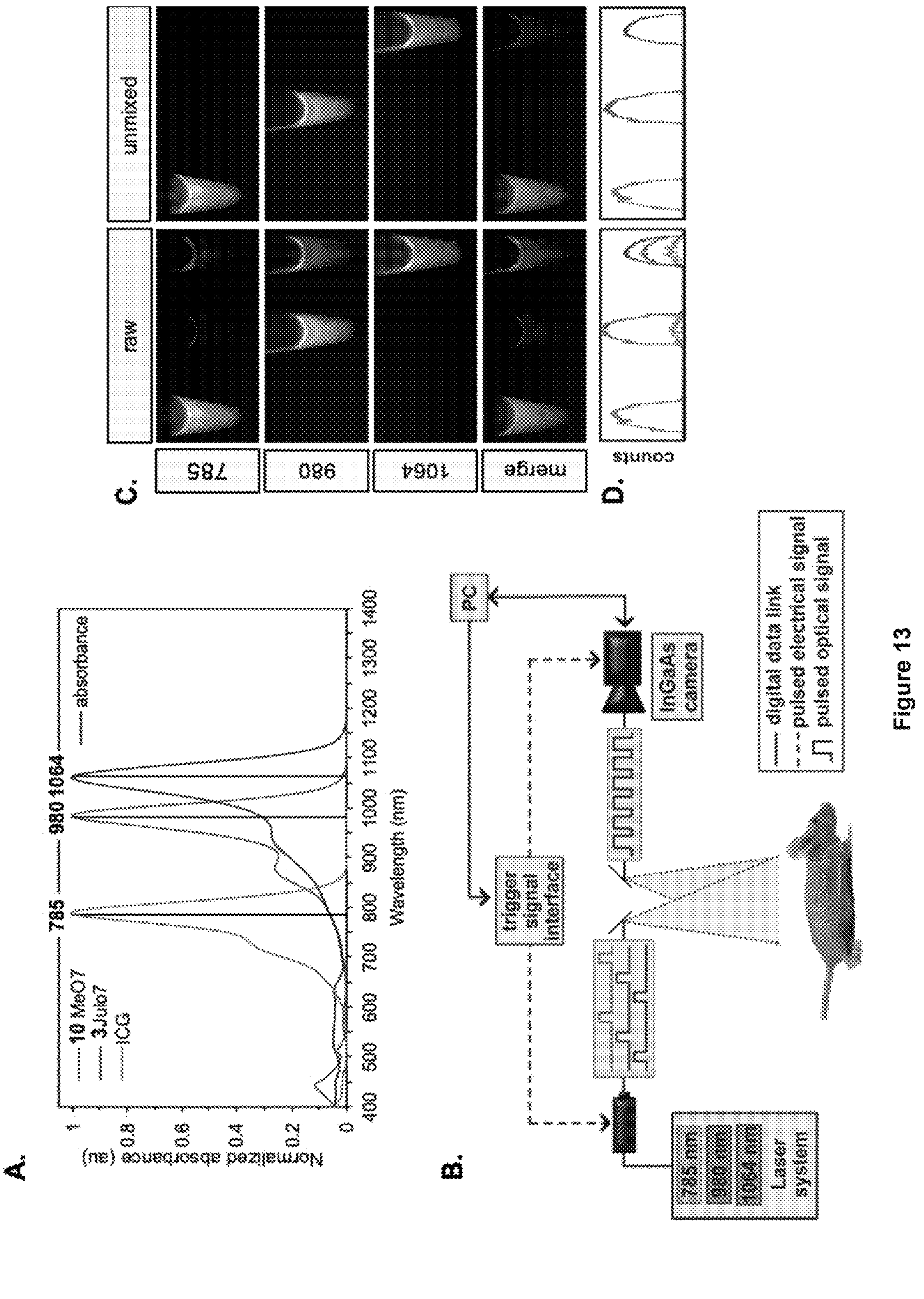
FIG. 13: Excitation-multiplexed SWIR imaging configuration. A) Absorption profiles of heptamethine dyes ICG (in ethanol), and 10 and 3 (in DCM), aligned with common laser wavelengths 785 nm, 980 nm, and 1064 nm, respectively. B) A central trigger signal interface controls the excitation sources and InGaAs camera and integrates data with computer (PC). Sequential pulsed excitation light is delivered to the biological sample. Color-blind detection by the InGaAs camera collects frames which are separated temporally by color. The PC collects, stores, and displays raw data in real-time during image acquisition. C) Intensity profile of three successive frames and D) merged 3 color images of vials containing ICG in ethanol (left), 10 in DCM (center), and 3 in DCM (right). Dye concentrations were 0.004 mg/mL in the respective solvents. Samples were excited with laser wavelengths 785 nm, 980 nm, and 1064 nm. Frames were acquired with 5 ms exposure time, 33 fps, and collection between 1300-1700 nm. Raw and unmixed data are shown on the left, and right, respectively. D) Intensity plots of the data presented in (C).

For excitation multiplexing, we are most interested in properties of the series of polymethine fluorophores when exited at 980 and 1064 nm. Thus, we calculated brightness ($\varepsilon_A$) values for each dye using the absorbance coefficient at the respective wavelengths. It is clear that the original fluorophore Flav7 is not suited for excitation multiplexing as it has similar brightness ($\varepsilon_A$) values at λ=980 and λ=1064 nm. Gratifyingly, clear candidates emerge for imaging at these common wavelengths, with 3 (Julo7) being superior for imaging at 1064 nm (brightness ($\varepsilon_{1064}$)=1090±40 $M^{-1}$ $cm^{-1}$) and 10 (MeO7) having the advantage at 980 nm (brightness ($\varepsilon_{980}$)=980±20 $M^{-1}$ $cm^{-1}$). The parings can be further visualized by observing the absorption profiles and excitation wavelengths on the same plot (FIG. 13A). A third color can be achieved with the heptamethine ICG, which is well-matched to 785 nm excitation.

To perform excitation multiplexing in the SWIR, a custom SWIR imaging configuration with three lasers and an InGaAs detector was built (FIG. 13B). With laser lines at 785 nm, 980 nm, and 1064 nm, tailored excitation could uniquely excite three fluorophores. Emission is detected in a color-blind fashion using identical filters and settings in the SWIR, providing high-resolution images. To enable this process to occur in real-time, we constructed an electronic triggering system which is coupled to both the camera and laser excitation sources. Triggers on the millisecond time scale are sent independently to each CW laser and the detector and programmed to collect a single frame for each sequential excitation pulse. The detection unit and triggering unit were integrated with MATLAB into a control unit (PC) which collects, stores and displays the collected data in real-time. In effect, a modular system resulted, in which wavelengths used and exposure time could be tuned to the experimental conditions. While the effective frame rate of collection was slowed by a factor equal to the number of channels, video-rate acquisition was still achievable in this method due to the low exposure times needed.

To test the performance in vitro, vials containing solutions of ICG (left), and flavylium dyes 10 (center) and 3 (right) were imaged with the custom configuration (FIG. 13B). Three successive frames show high intensities at the left (frame 1), center (frame 2) and right (frame 3), matching the locations of each vial (FIG. 13C-D). Merging the 3 frames together yields a three colored image representing one effective multiplexed frame (FIG. 13C-D). Because molecules cannot absorb light at energies lower than their S0 to S1 transition, cross-talk occurs only in one direction, is minimal, and can be unmixed by image processing.

Figure 14:
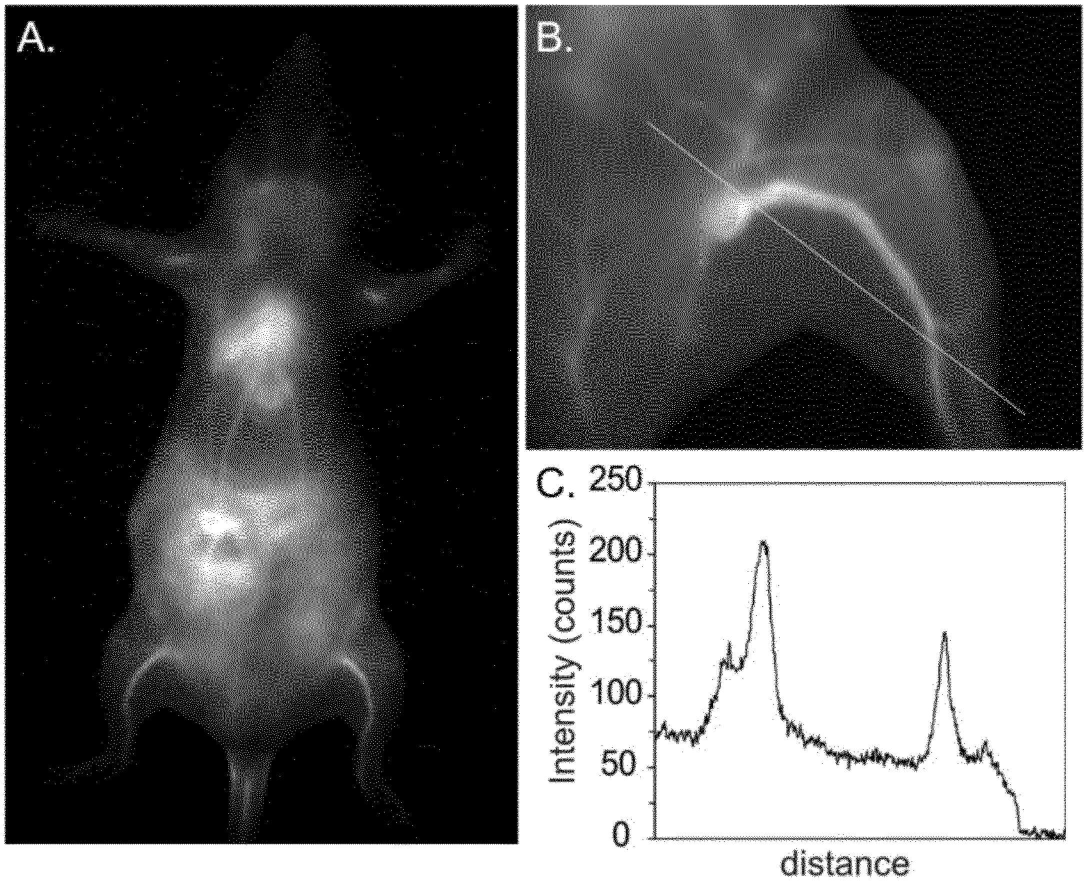
FIG. 14: In vivo imaging with 1064 nm excitation. A) Whole mouse imaging at 100 fps, seconds after injection of 12 micelles, collection 1100-1700 nm. B) Close up of the hindlimb after 12 micelle injection, collection 1200-1700 nm. Yellow line indicates roi used in (C). C) Intensity profile of (B), demonstrating the contrast observed in veins and arteries versus diffuse tissue signal.

Before performing multiplexed experiments in vivo, imaging with 1064 nm excitation using 3 (Julo7) as a contrast agent was optimized. To facilitate its dispersion in water, 3 was encapsulated in PEG-phospholipid micelles. The resulting micelles remained stable for at least one week and retained absorptive and emissive properties of the dye in organic solvent. Micelles were introduced by tail vein injection into anesthetized mice and immediately imaged with ex. 1064 nm (FIG. 14A). Due to the large amount of signal achieved, we were able to obtain images at 100 fps, with an 8 ms exposure time, collecting from 1100-1700 nm. These fast speeds suggested that high-quality images could still be obtained upon multiplexing. Moving to detection with 1200 nm LP allowed for more enhanced contrast and spatial resolution FIG. 14B-C).

Figure 15:
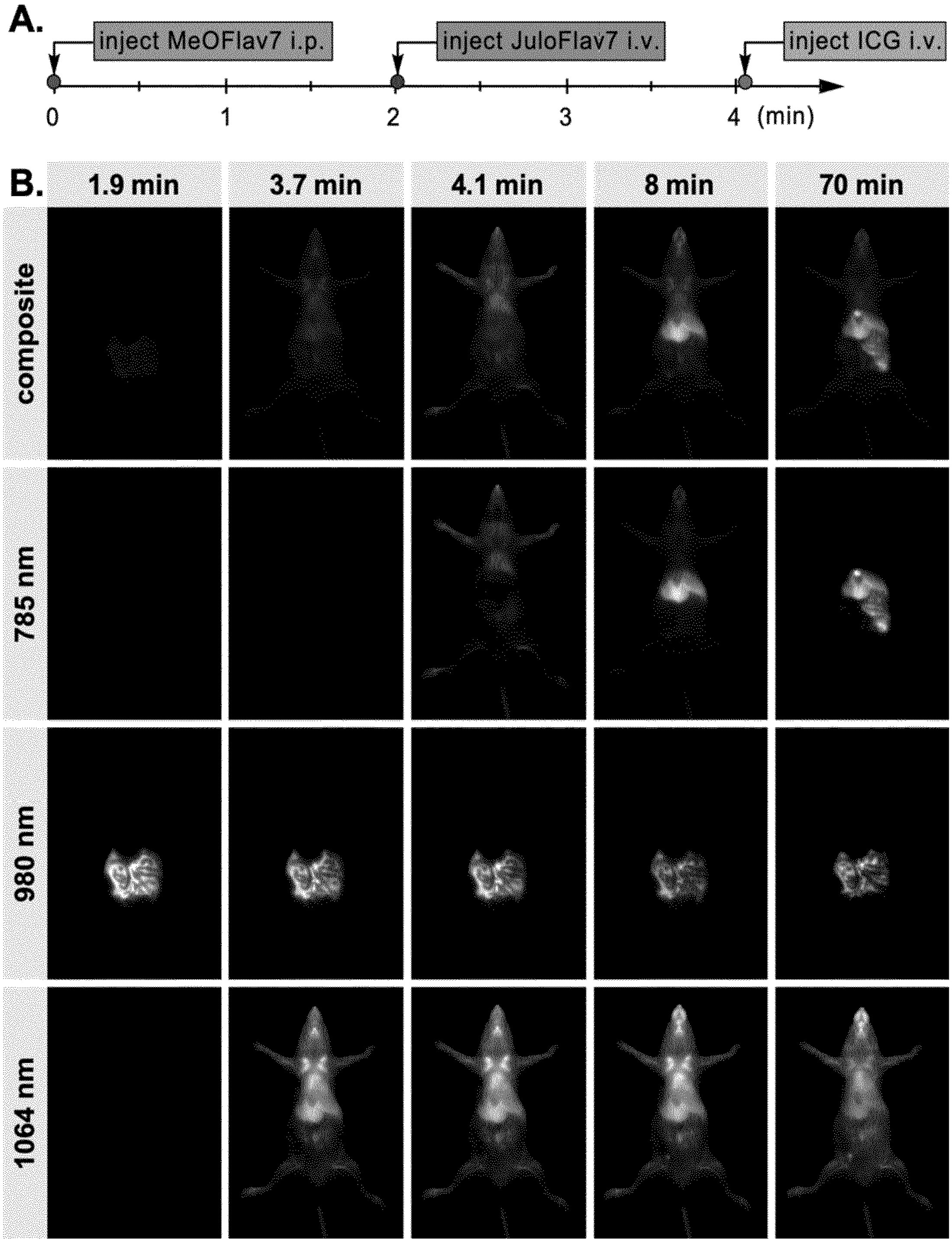
FIG. 15: Excitation-multiplexed SWIR imaging. A) Administration of three probes: emulsions of 10 i.p., and micelles of 3 and ICG i.v. B) Multiplexed in vivo images using 785 nm, 980 nm, and 1064 nm excitation, acquired at timepoints before and after injection of ICG. Collection occurred between 1150-1700 nm, with 10 ms exposure time, 27.8 fps. The contrasting biodistribution can be visualized over time in the merged images and in each individual wavelength channel.

To obtain real-time images in three colors, heptamethine 10 was encapsulated in PEG-coated micelles to impart water solubility. In vivo, we introduced 10 micelles by intraperitoneal injection, and 3 micelles followed by ICG by intravenous injection. Representative time points of the three-color video are displayed in FIG. 15. After establishing both the technology and the molecular tools for multiplexed real-time observation of function in mice, the next goal was to enhance existing SWIR imaging applications.

Figure 16:
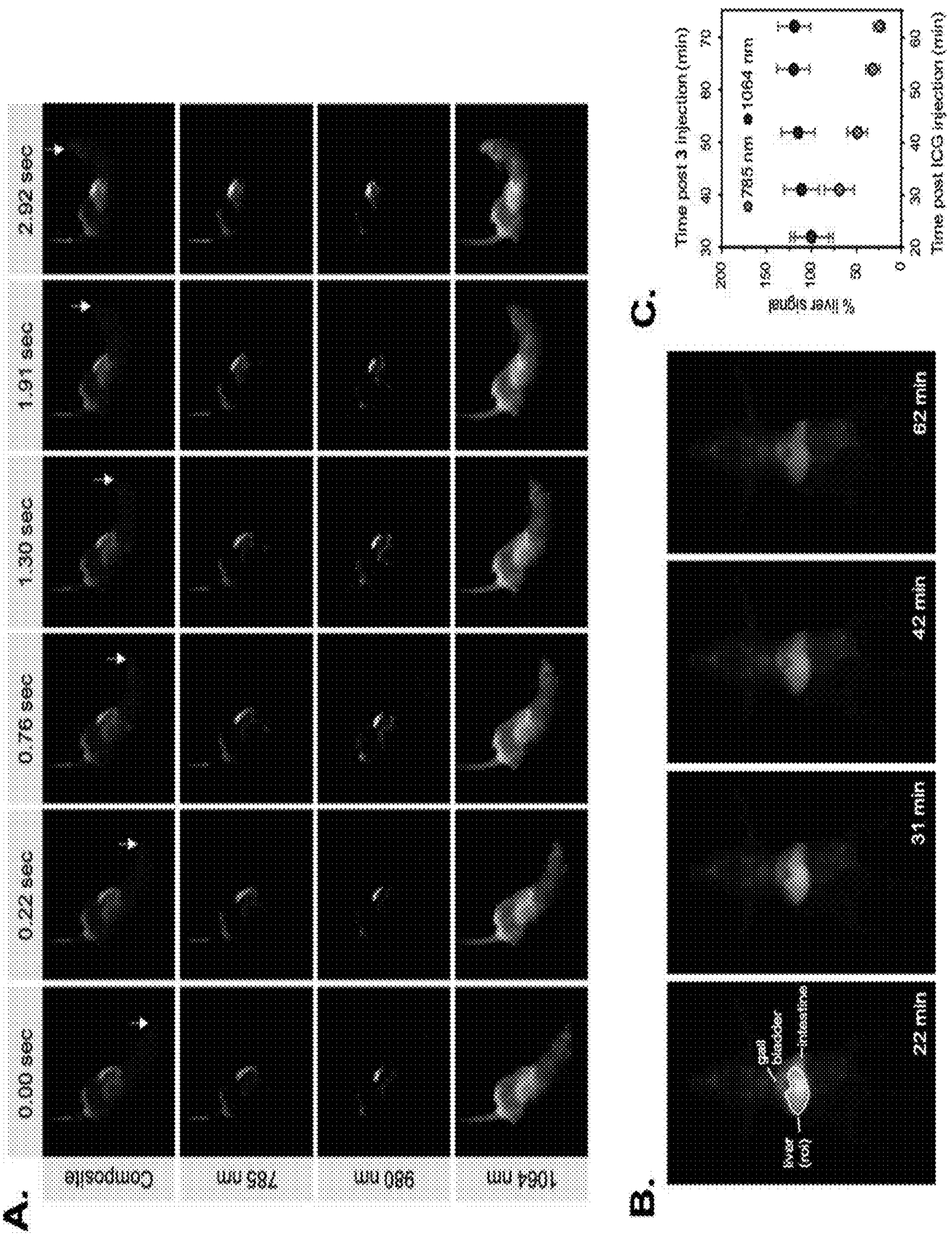
FIG. 16: Applications enhanced by SWIR multiplexed imaging. A) Multiplexed imaging of an awake mouse, in 3 colors i.p. injection of 10 micelles, i.v. injection of ICG, and i.v injection of 3 micelles. Shown are closely acquired frames during one continuous movement of the head. Images were acquired with 785 nm, 980 nm, and 1064 nm ex. (110 $mWcm^{-1}$) and 1150-1700 nm collection (10 ms exposure time; 27.8 fps). B) Imaging of ICG clearance with systemic labelling by 3 micelles. Multiplexed in vivo images using 785 nm and 1064 nm ex. (100 $mWcm^{-1}$) and 1150-1700 nm collection (5 ms exposure time; 50 fps). C) Percent signal in the liver of ICG and micelles of 3 over one hour.

Physiological properties such as heart-rate, respiratory rate, thermoregulation, metabolism, and the function of the central nervous system, are highly impacted by anesthesia. Methods to observe animals in their natural state are necessary to study physiology, but are currently limited to telemetric sensors and electrocardiography, which involve surgical implantation or external contact, respectively. Recently, high-speed SWIR imaging has enabled contact-free monitoring of physiology in awake mice. Due to frame rates which are faster than macroscopic movements in animals, the heart rate and respiratory rate in awake animals can be quantified. In this study, we expanded this technique by observing awake mice in three colors. The method allows physiology to be monitored with minimal perturbation of the animal's usual environment. In FIG. 16A, awake mouse imaging was performed 80 minutes after i.p. administration of 10 micelles and consecutive i.v. administration of 3 micelles and ICG. From the top-view of the mouse, ICG could be visualized exclusively in the liver, 10 micelles in the abdomen, while 3 micelles remained systemically distributed throughout the mouse. The real-time collection can be visualized by observing close time-points in which a continuous movement is monitored without visual aberrations (FIG. 16A). In addition to assessing natural physiology, these tools foreshadow more complex experiments in which the location of multiple probes could be monitored over long periods of time, non-invasively and without the need for anesthesia.

Secondly, biological reference can be added to existing experiments which visualize a single organ or organ system. Beyond its approved clinical practices, many off-label uses of ICG have been established. ICG clears efficiently and exclusively from the liver. Relying on this property, methods to study intestinal mobility in the presence of disease or pharmacological agents have been developed. By adding a second channel in these experiments, we anticipated that the liver and intestines could be visualized within the context of the adjacent structures. To demonstrate this application, we injected 3 micelles and ICG consecutively through the tail vein and imaged the whole mouse at several time points over a one-hour period. In the duration of the experiment, the signal from the 1064 nm channel remained constant, serving as a stationary reference for changes in the 785 nm channel in the intestine (FIG. 16B-16C).

Conclusion: enabled by a set of flavylium heptamethine dyes with diverse wavelength excitation and by a triggered multi-excitation SWIR optical configuration, multiplexed whole animal imaging with high spaciotemporal resolution was demonstrated. The technologies developed in the course of this invention advance the ability to monitor orthogonal function in animals, a major advance in imaging methods.

Example 10: Method and Device for Imaging Fluorescent Proteins in Near- and Short-Wave Infrared This examples was carried out according to the second exemplary schematics of the method and device for imaging fluorescent proteins in near- and short-wave infrared requiring a (labelled) fluorescent biological sample (FIG. 18), an optical setup for detection and an excitation light source, wherein "1" is an excitation unit comprising: a power supply and a light source; "2" is a transmission unit comprising: an excitation filter and optical elements (lenses and diffuser); "3" is a detection unit comprising: optical elements, emission filter, detector, processor, data storage and display.

Figure 19:
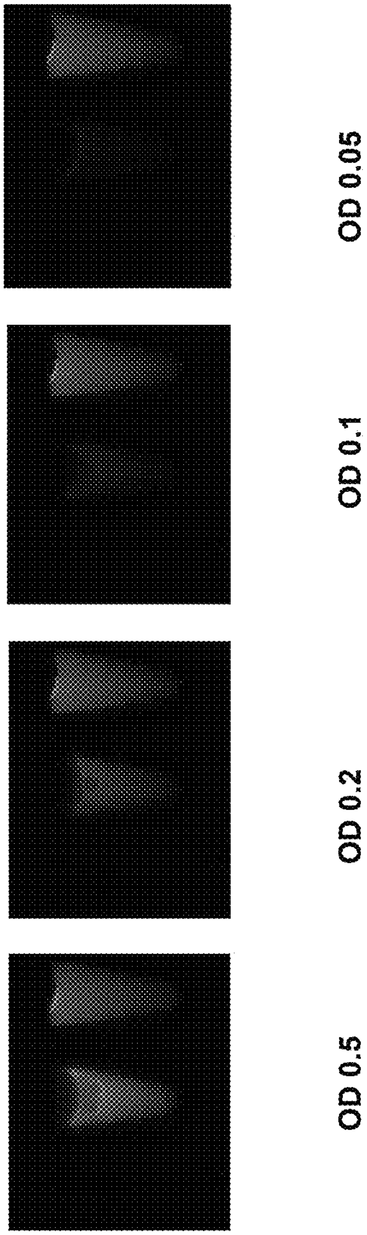
FIG. 19: Different concentrations of tdTomato imaged in SWIR.

In this example different concentrations of TDTomato were imaged in SWIR. The emission set up comprised a longpass filter (1000 nm) to filter out emissions below 1000 nm. Excitation was carried out by two LEDs with the wavelength of 565 nm in addition to an excitation filter and optics. Imaging results (FIG. 19) show: left tube in every image is PBS (buffer), middle tube in every image is a TDTomato solution with a different OD (i.e., OD of 0.5, 0.2, 0.1, 0.05 from left to right) and right tube in every image is a TXred solution as internal reference (OD of 0.5).

These results demonstrate that fluorescent proteins are detectable in SWIR and therefore also in NIR opening numerous novel applications for such proteins in biomedicine.

Example 11: Spectrum of the Fluorescent Protein tdTomato Measured to 700 nm

Figure 20:
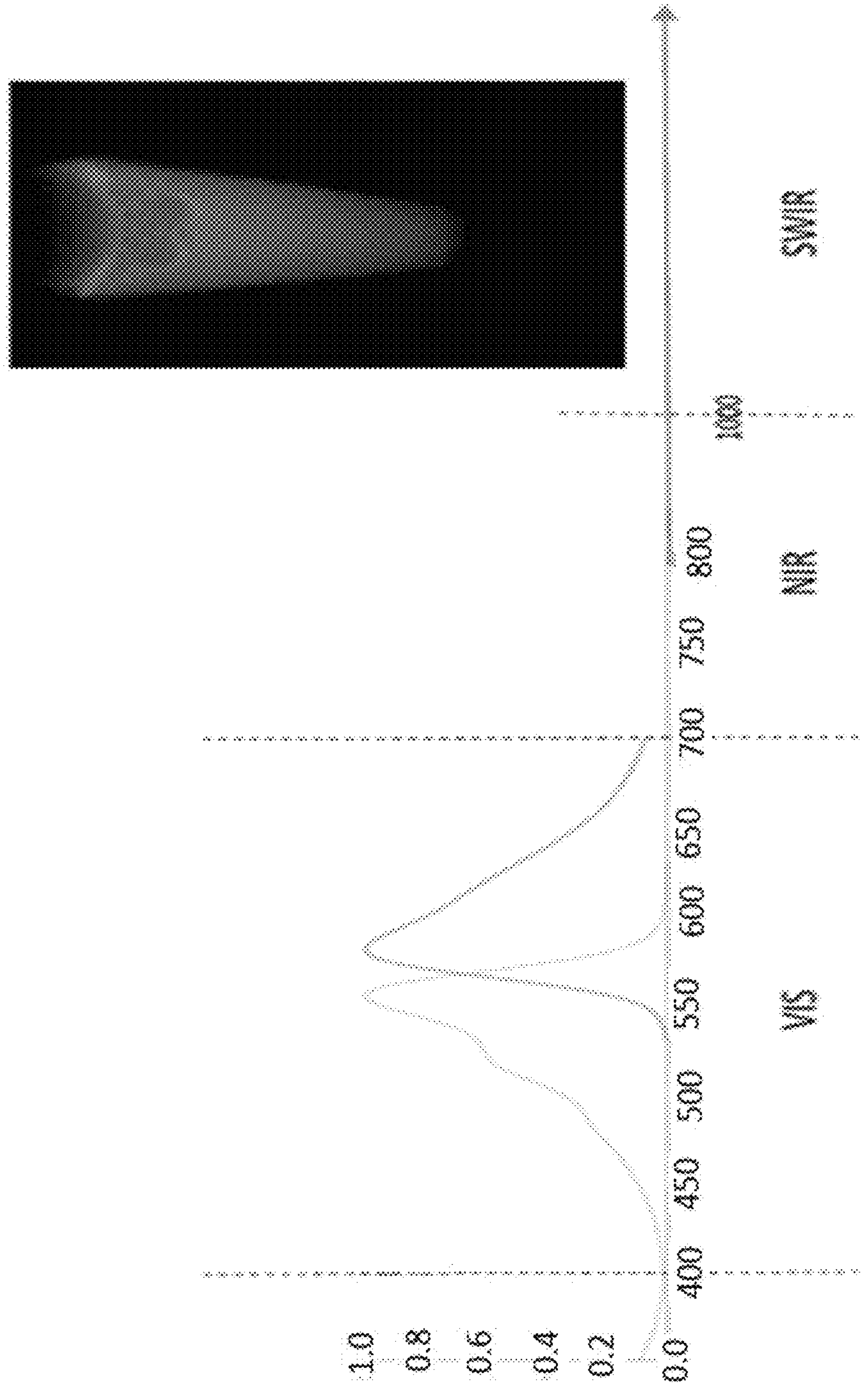
FIG. 20: Imaging of tdTomato in the NIR and SWIR.

In this example the spectrum of fluorescent protein tdTomato (taken from the literature) was measured only to 700 nm. However, it was shown that tdTomato signal was present in the NIR and SWIR. This can be seen in the fluorescence of the vial measured above a wavelength of 1000 nm (FIG. 20). The yellow curve presents the absorption spectrum of tdTomato and the orange curve the emission spectrum.

Excitation-Side Optics:

Light Sources (565 nm LEDs, 575 Band-pass filter, 800 Short-pass filter, 25 mW/cm^2)→Collimator→Engineered Diffuser→Sample. The arrows represent the light path. Accordingly, the light path has been set up as follows: from Light Sources (565 nm LEDs, 575 Band-pass filter, 800 Short-pass filter, 25 mW/cm^2) to Collimator to Engineered Diffuser to Sample.

Emission-Side Optics:

Sample→3×f=500 mm C-Coated lenses→Silver Mirror→1000 nm Long-pass Filter→2×f=200 mm C-coated lenses→InGaAs Detector. The arrows represent the light path. Accordingly, the light path has been set up as follows: from Sample to 3×f=500 mm C-Coated lenses to Silver Mirror to 1000 nm Long-pass Filter to 2×f=200 mm C-coated lenses to InGaAs Detector.

Detector: Allied Vision Goldeye G032 GigE TEC2—InGaAs SWIR camera

Conclusion: It is possible to use existing biological samples that are labelled with fluorescent proteins to image those biological samples in the near-infrared and the short-wave-infrared. This provides the opportunity to shift biological imaging into a different wavelength regime. This now opens the market for optical instrument manufacturers to build imaging devices optimized for the NIR/SWIR regime. This new method now creates new opportunities for daily biological imaging tasks.

Selected Advantageous Features of the System of the Present Invention:

Full control over excitation and detection enabling multiple applications. Imaging in the SWIR region benefiting from less scattering, autofluorescence, etc. Possibility to image off-peak, emission signal of fluorophores sufficient off-peak. Multi-Color real-time imaging in the SWIR. Compatible with Matlab and Simulink programming environments. 16 MHz 32 bit AVR Microcontroller based trigger unit. Flexible and reconfigurable optical system.

Example 12: In Vitro and In Vivo Imaging with Exemplary Fluorescent Proteins

We demonstrate that the three presented fluorescent proteins (sfGFP having e.g., SEQ ID NO: 61, tdTomato having e.g., SEQ ID NO: 60, IRFP720 having e.g., SEQ ID NO: 59) exhibit emission beyond 1000 nm. In order to assess if the signal of those proteins is sufficient to be used in our current SWIR imaging configuration, we imaged different concentrations of the purified fluorescent proteins. We excited the fluorescent proteins with their corresponding excitation wavelengths 470 nm, 565 nm, 660 nm, using collimated LEDs, whose excitation light has been cleaned up by spectral short-pass filters. We detected the emission signal with an InGaAs SWIR Camera (Allied Vision Goldeye—032) equipped with two 1000 nm long-pass filters and a SWIR optimized. Additionally, we changed the exposure times of the excitation light sequentially, ranging from 10-500 ms, to determine the linearity of the emission signal.

Figure 21:
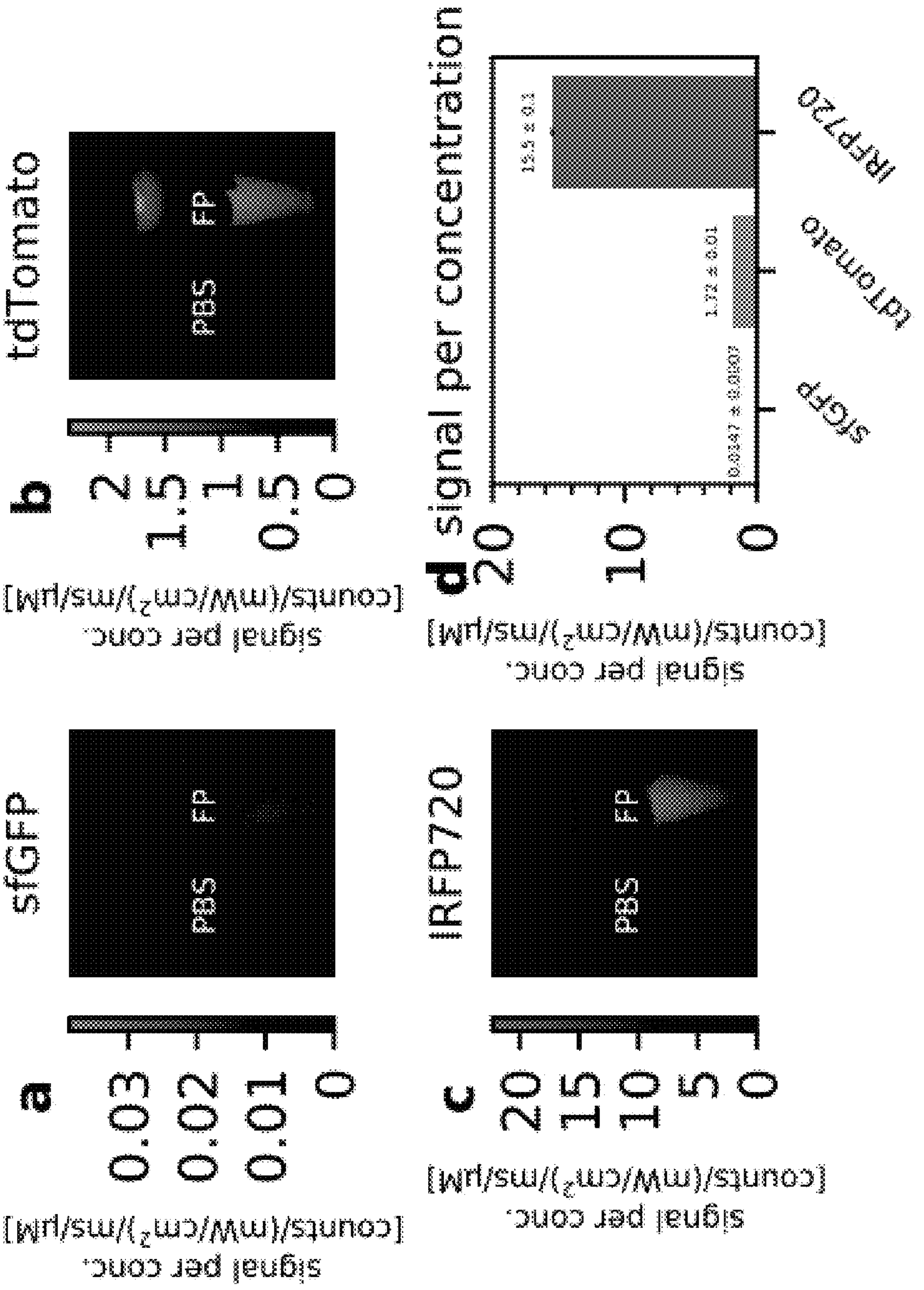
FIG. 21: In vitro imaging with exemplary fluorescent proteins. a-c: Fluorescent proteins FP, next to PBS imaged above 1000 nm normalised for exposure time (200 ms), excitation power (sfGFP: 8:4 mW=cm2, tdTomato: 5:3 mW=cm2, IRFP720: 4:6 mW=cm2) and concentration (sfGFP: 45:9 μM, tdTomato: 7:30 μM, IRFP720: 1:52 μM). d: signal per concentration for the three tested fluorescent proteins.

For each concentration and exposure time, including a vial of PBS as control, the acquired frames were dark corrected and averaged. Dark frames were taken with excitation light sources turned off at same exposure times used to image the vials. Further, we normalised the averaged frames to excitation power [mW/cm^2], exposure time ms] and concentration [mu M], resulting in signal per concentration for each of the fluorescent proteins. (e.g., FIG. 21 (*a-c*) shows representative resulting normalised frames).

In order to establish the relation between the fluorescent protein signal and the concentration, we measured normalised signals of the fluorescent proteins for varying concentration. The control vial of PBS was used to measure excess signal coming from plastic of the vials, this measurement serves as baseline against emission signal of the fluorescent proteins. A region-of-interest ROI was drawn on the dark corrected, averaged vials, including the control PBS vial. The resulting counts in the ROI were normalised for excitation power [mW/cm^2] and exposure time [ms]. The normalised mean counts in the ROI of the fluorescent proteins were background corrected with the normalised mean counts derived from the PBS vial. A linear fit was performed, as the data indicates a linear relationship, through data-points that lie well within the dynamic range of the camera. The slopes of the linear fit were plotted in the bar chart FIG. 21 (*d*). The error bar arises from the standard deviation of counts in the regions of interest and the error in measurement of the excitation power, it was assumed that the concentration of fluorescent protein and the exposure time do not carry a significant error.

In general, we expect that the further red-shifted fluorescent protein has the strongest emission tail beyond 1000 nm. The findings are consistent with our expectations, the most red-shifted fluorescent protein IRFP720 has shown the strongest emission tail in the SWIR range. We acquired the highest signal per concentration for IRFP720 in our imaging configuration in comparison to tdTomato and sfGFP. The signal per concentration of the fluorescent protein IRFP720 is a factor nine higher compared to tdTomato and three-orders of magnitude higher compared to sfGFP.

We conclude, that looking at fluorescent proteins in isolation, the most red-shifted fluorescent protein IRFP720 is the most favourable fluorescent protein of the three studied for imaging above 1000 nm ex vivo.

Autofluorescence:

Autofluorescence, the natural emission of light after excitation by biological tissue, is a limitation for fluorescent imaging as it decreases the detection sensitivity of fluorescent probes. Fluorescent probes create a positive contrast between the probe and the surrounding (e.g. un- or differently labelled tissue). Assuming one wants to image a single probe in unlabelled tissue, the contrast can be enhanced by either using a brighter probe or by reducing autofluorescence of surrounding tissue. Previously it has been shown that autofluorescence in the SWIR is less apparent compared to the VIS or NIR spectral range.

In order to understand the magnitude of the autofluorescence signal after exciting in the visible and imaging above 1000 nm, we applied the same imaging configuration we developed for imaging fluorescent proteins in isolation to estimate the autofluorescence of the lower back of mice.

As with the ex-vivo vials, we acquired the autofluorescence above 1000 nm, while sequentially changing the exposure time of a freshly sacrificed mouse. For each of the excitation wavelengths, the frames were dark corrected and averaged. We normalised the measured counts to excitation power [mW/cm^2] and exposure time [ms], representative frames are shown in FIG. 22 (*a-c*).

Figure 22:
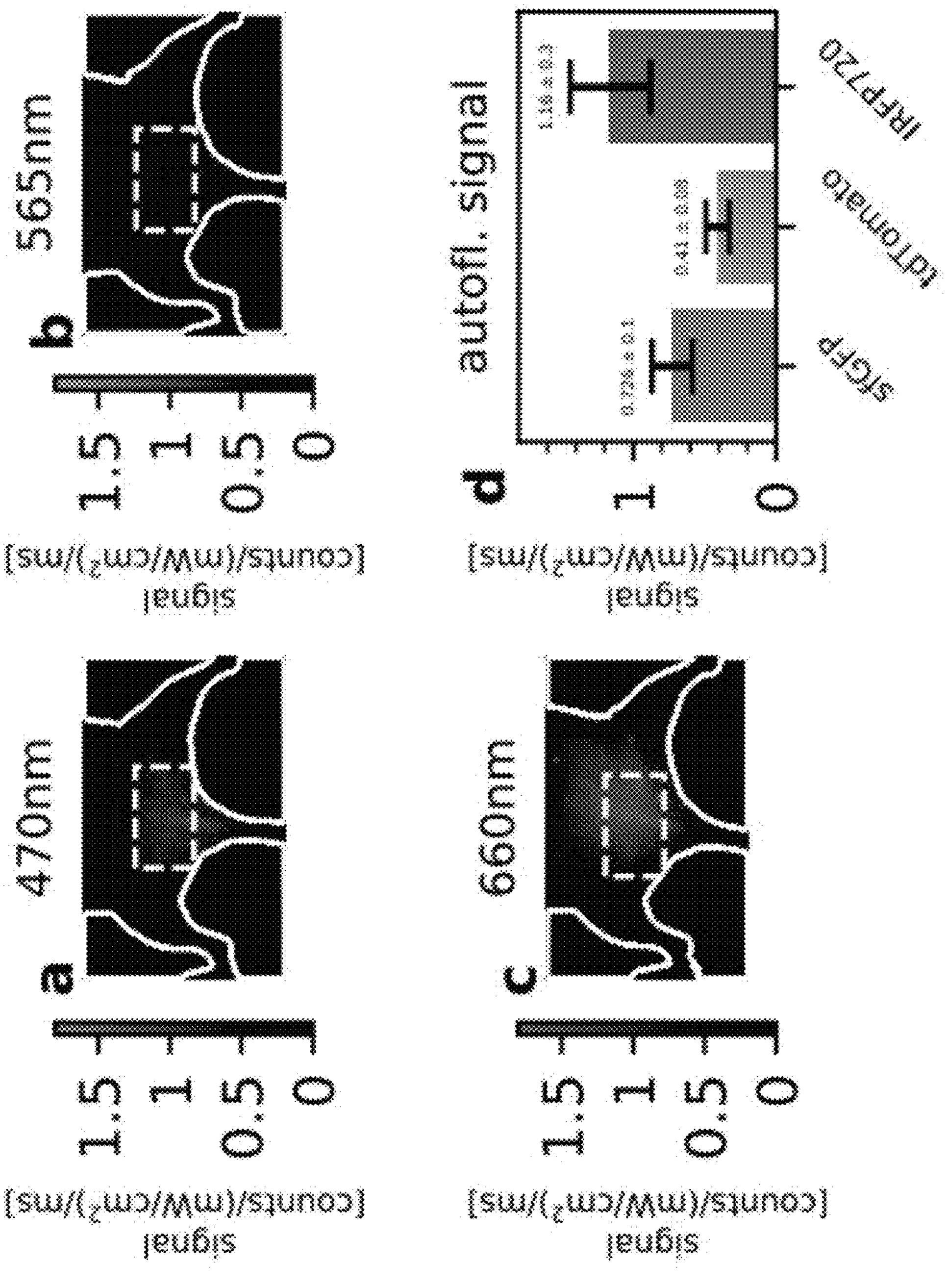
FIG. 22: In vivo imaging with exemplary fluorescent proteins. a-c: Lower back of a mouse imaged after excitation with corresponding wavelengths and normalised for exposure time (200 ms) and excitation power (sfGFP: 12:1 mW=cm2, tdTomato: 8:57 mW=cm2, IRFP720: 9:71 mW=cm2). d: auto fluorescence signal for different excitation wavelengths.

Using the same approach as for the proteins in isolation, we drew a ROI on the lower back of the mouse, indicated in FIG. 22 (*a-c*), measured mean counts and normalised for excitation power and exposure time. We plotted the resulting signal against exposure time and fitted a horizontal line, to estimate the magnitude of the autofluorescence signal. The resulting normalised autofluorescence signal is shown in FIG. 22 (*d*). The error arises due to the standard deviation of the counts in the ROI and the experimental error in the measurement of the excitation power.

We understand that autofluorescence is varying between organ tissue and other external factors such as diets, nonetheless the estimation of autofluorescence allows to understand the performance of fluorescent proteins While the autofluorescence signal in the SWIR is approximately comparable for the different excitation wavelengths, the least autofluorescence signal arises from 565 nm and most signal from 660 nm excitation. To understand the signal arising from the fluorescent proteins in context of autofluorescence, we divide the previously acquired signal per concentration for vials of the purified proteins and the autofluorescence signal acquired of the lower back of the mouse. This results in the signal over background for this specific configuration. By taking the inverse of the signal over background, we can estimate the autofluorescence equivalent concentration, a metric to determine the minimal concentration of fluorescent protein required to match the autofluorescence signal for this configuration.

IRFP720 outperforms the competing fluorescent proteins significantly, by having a factor three more signal over concentration compared to tdTomato and a factor of 670 more relative to sfGFP. After considering the autofluorescence, the fluorescent protein IRFP720 is the most favourable fluorescent protein of the three tested to conduct in vivo SWIR imaging with our current configuration, having the highest signal over concentration estimation.

Autofluorescence Measurements:

| Fluorescent protein/excitation wavelength | signal per conc. | autofluorescence | autofluorescence equiv. conc. |
|---|---|---|---|
| sfGFP/470 | 0.0147 ± 0.0007 | 0.726 ± 0.1 | 49.4 ± 10.0 |
| tdTomato/565 | 1.72 ± 0.01 | 0.41 ± 0.08 | 0.237 ± 0.05 |
| IRFP720/660 | 15.5 ± 0.1 | 1.16 ± 0.3 | 0.0747 ± 0.02 |

Reporter Mouse

Imaging transgenic mice expressing fluorescent proteins to study in vivo biological processes is well established for the VIS and NIR spectral range.

One known limitation when imaging in this spectral window is melanin. Melanin possesses enhanced absorption properties in the VIS and NIR. Thus, when exciting fluorescent proteins in biological context, melanin reduces the excitation efficiency and reduces the number of transmitted photons emitted from the fluorescent proteins through tissue. This leads to an obstruction of the underlying genetically labeled structure in the acquired image, thus limiting the extraction of information.

However, acquiring the image in the SWIR spectral range, reduces the effect of melanin on the emission side, as melanin has reduced absorption in the SWIR. This allows to extract certain biological information which might not be possible in the VIS/NIR range.

Figure 23:
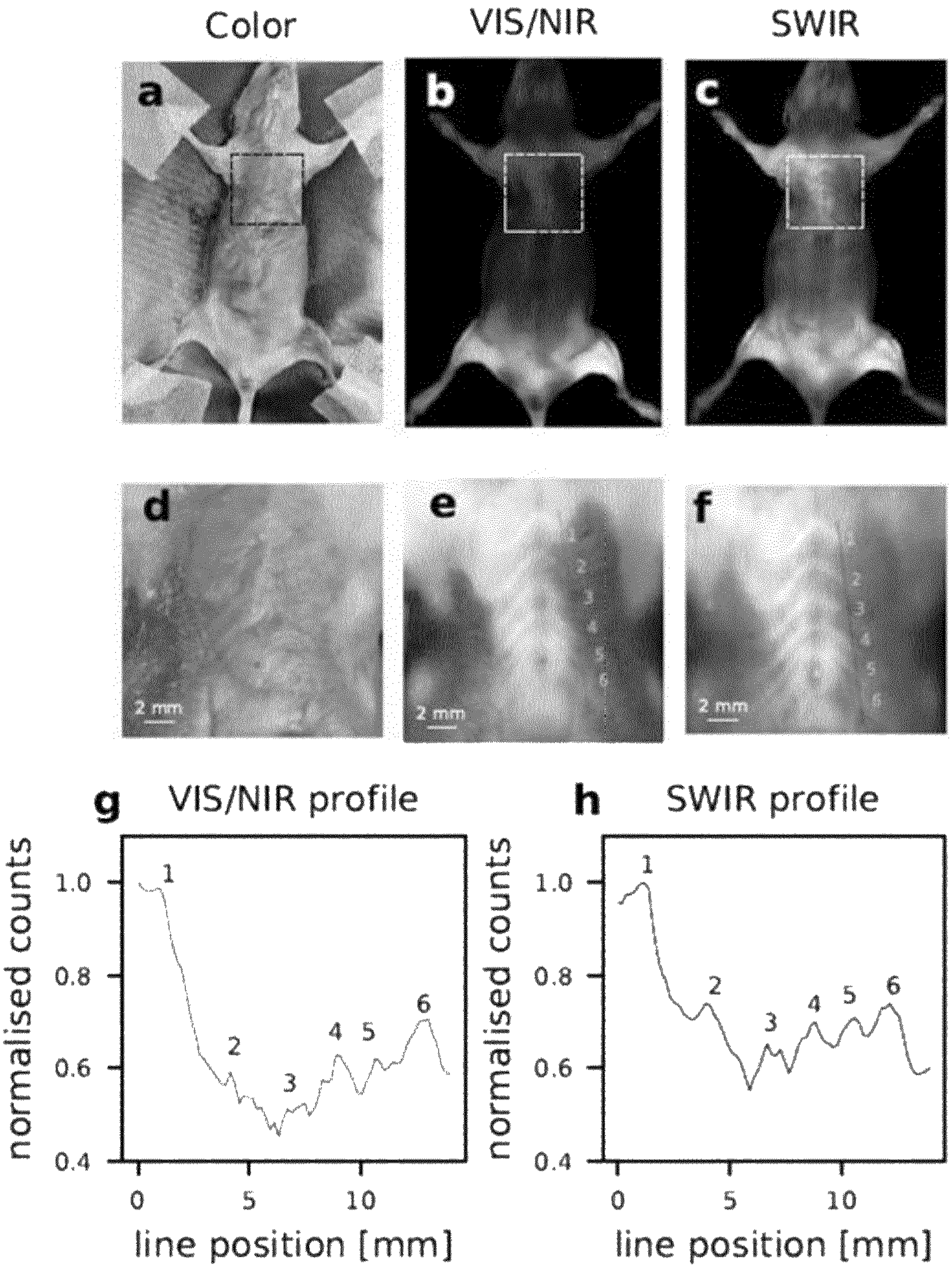
FIG. 23: Imaging of a reporter mouse where Collagen VI has been labelled with tdTomato. a: Color image of the reporter mouse. b: VIS/NIR fluorescence image of the mouse. c: SWIR fluorescence image of the reporter mouse. d-f: zoom on chest in Color, VIS/NIR and SWIR. g-h: Line-profiles extracted from the VIS/NIR and SWIR zoom images.

We imaged a highly expressing reporter mouse in the VIS/NIR and SWIR (FIG. 23), in which Collagen VI (ColVI) has been labeled with the fluorescent protein tdTomato. As ColVI is associated with muscle tissue, we expect strong signal arriving from the hind legs of the mouse. Further, the skin is labeled, this allows to compare the effects of melanin in the different imaging windows.

We used 565 nm LEDs, collimated and equipped with clean-up filters to excite the fluorescent protein tdTomato.

A camera with silicon detector with the same objective used in the previous SWIR configuration was used to image in the VIS/NIR spectral range. We added two emission filters (600 nm long-pass and 675 nm long-pass) to image the fluorescent protein labeled structures. We performed a flat-field correction on the acquired image.

For the SWIR image, we imaged using the same imaging set-up used in the previous experiments. We acquired a stack of images, dark-corrected, flat-field-corrected and averaged the images.

To understand the effects of melanin, we utilized the rib cage of the mouse as a resolution target. The image was cropped and a line was drawn over the rib cage, where melanin is present. We extracted the line-profiles and normalized the profiles to 1.

Looking at the values of normalised counts, melanin has a stronger effect in the VIS/NIR, where it is difficult to extract the pixel position of the ribs 2 and 3. In contrast to the SWIR line-profile, where the extraction of the ribs position and the number of ribs is more apparent.

Thus, if melanin is an obvious limitation to imaging of reporter mice, shifting the imaging window to the SWIR might be beneficial for certain applications.

The ColVI-tdTomato mouse model is highly expressing, seen in the color image. In this mouse model the fluorescent proteins are secreted in fibroblasts. Fibroblasts are large cells that allow for a high number of proteins being in the cell, thus the emission of fluorescent signal is expected to be high.

Figure 24:
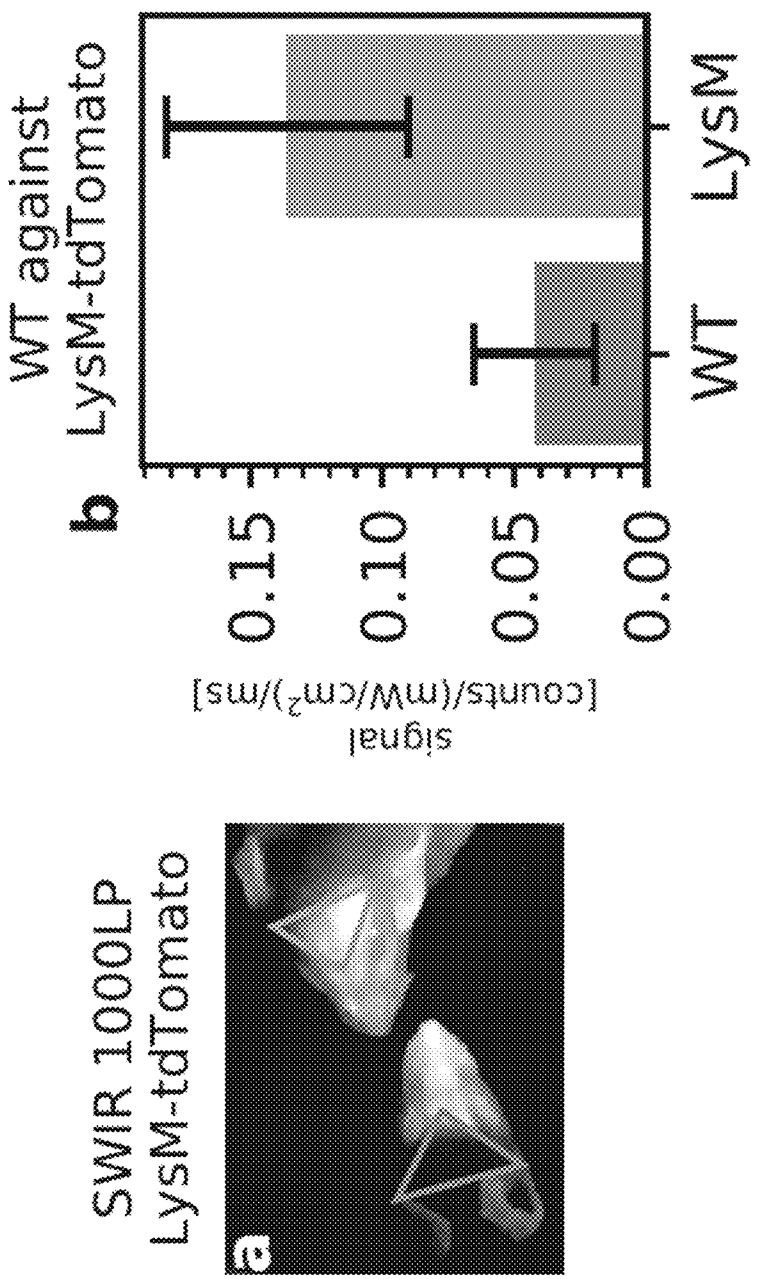
FIG. 24: SWIR imaging of a reporter mouse where Lys M has been labelled with tdTomato and a wildtype mouse. a: SWIR image with regions-of-interest indicated. b: Comparison of mean values measured in the regions-of-interest.

However, imaging reporter mice in the SWIR is not limited to fibroblasts. We imaged a LysM-tdTomato reporter mouse using the same imaging configurations as the ColVI-tdTomato reporter mouse (FIG. 24). We found that the fluorescent protein expression could be detected in the brain of the mouse, in comparison to a WT mouse. The signal normalised to excitation power and exposure time was measured as the mean in the drawn ROI on the head of the mouse. The signal from the brain of the mouse is around a factor 2 higher compared to the WT.

While it is possible to image reporter mice in the SWIR and the reduced absorption of melanin is an advantage, the signal detected is lower compared to the VIS/NIR. Further, one has to be careful to select the mouse model, as the expression levels of the fluorescent proteins in the mouse models has significant influence on quality of the acquired images in the SWIR.

Tumor Imaging

Recently, the SWIR spectral range has proven to be useful in imaging vasculature by providing higher contrast between the labeled vasculature and the surrounding tissue in comparison to the VIS/NIR. This relies on different fluorescent probes, including Carbon Nanotubes (CNTs), Quantum Dots (QDs), Rare Earth-Doped Nanoparticles, and Organic Dyes.

Nonetheless, genetically encoded probes have not been used to image in the SWIR spectral range yet.

Now, we combine the advantages provided by the SWIR spectral range to image labeled vasculature with the ability to image transfected tumor cells simultaneously.

We established that the fluorescent protein IRFP720 emits the strongest emission above 1000 nm of the three previously tested fluorescent proteins. We transfected 4T1 tumor cells with IRFP720 and injected 1 Mio. of those cells in matrigel into the lower back of mice. Additionally, we injected 1 Mio. unlabeled 4T1 cells in matrigel into the lower back of mice as a control. Using the same imaging set-up used in the previous IRFP720 vial measurements, we imaged the tumor injection (day 1), tumor development (day 3), and the endpoint (day 5) of the tumor mice. At the endpoint we injected the clinical approved contrast agent indocyanine-green (ICG). We imaged the tumor and the injection of the contrast agent by multiplexing the excitation sources, utilizing the 660 nm LEDs for exciting IRFP720 and the 785 nm laser for exciting ICG.

Figure 25:
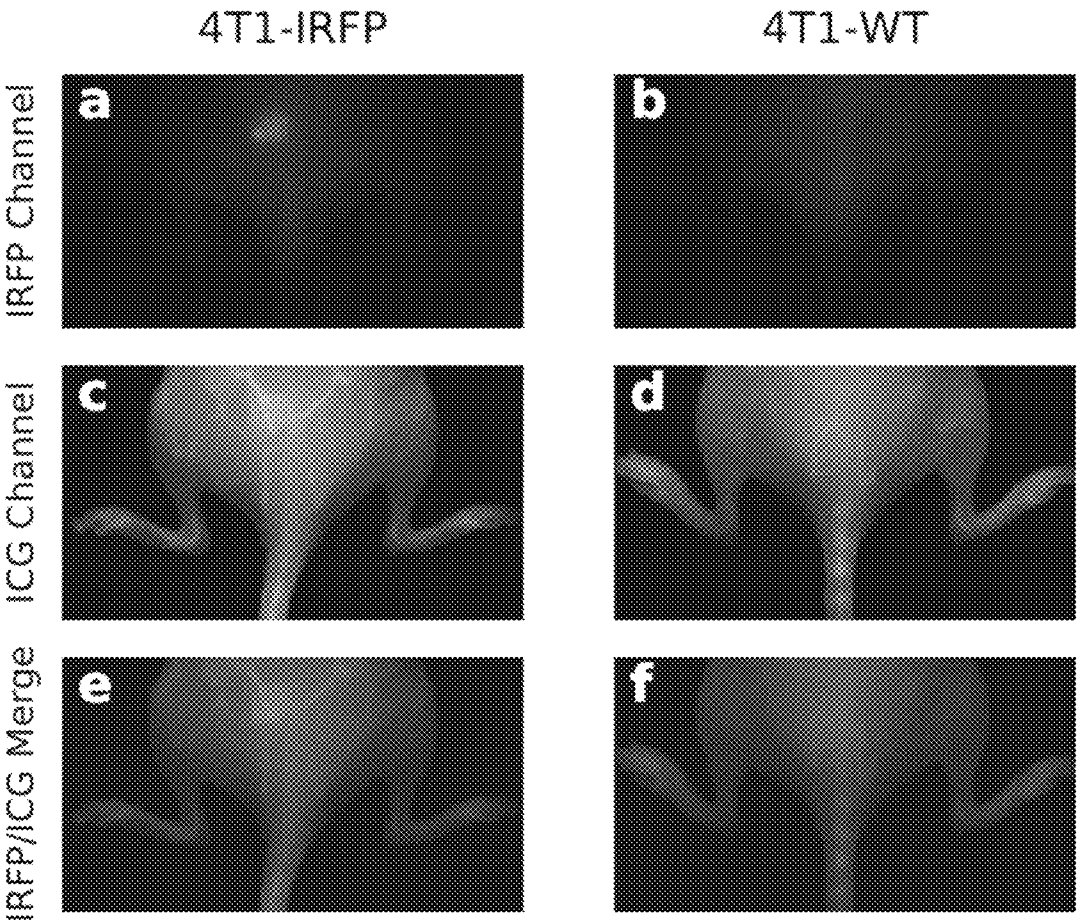
FIG. 25: SWIR imaging of mice injected with tumor cells. a-b: SWIR imaging of injected tumor cells (a: IRFP-4T1; b: WT-4T1). c-d: SWIR imaging of ICG injected in vasculature. e-f: IRFP720 and ICG channels merged.

We can distinguish the tumor labeled with IRFP720 from the surrounding tissue at day 5 in FIG. 25 (*a*). However, it is not possible to recognize the unlabeled tumor in in FIG. 25 (*b*). Further, after injecting the organic dye ICG, the vascularization of the tumor can be seen FIG. 25 (*c-d*). The merging of the channels provides the information of the tumor vascularization and the location of the tumor.

We have shown that it is possible to utilize cells labeled with the fluorescent protein IRFP720 provide information on the tumor location and are a viable tool to conduct imaging in the SWIR.

Conclusions

In this demonstration we have shown that is possible to utilize fluorescent proteins that are mainly used in the VIS and NIR spectral range to image beyond 1000 nm. Further, we established that the most red-shifted protein of the three-tested, IRFP720, emits the strongest above 1000 nm. Additionally, we imaged reporter mice that have been labeled with tdTomato, showing that it is also possible to use specific reporter mice in the SWIR spectral advantage, making use of reduced melanin absorption.

REFERENCES

1. Carr, Jessica, et al. WO 2017/160643
2. Carr, Jessica, et al. PNAS Absorption by water increases fluorescence image contrast of biological tissue in the shortwave infrared, Sep. 11, 2018. (37) 9080-9085.
3. Spectral imaging. zeisscampus.magnet.fsu.edu. [Online] 2019 http://zeiss-campus.magnet.fsu.edu/tutorials/spectralimaging/lambdastack/indexflash.html

CONCLUDING REMARKS

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The systems and methods described herein are presently representative of certain embodiments, are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied herein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

What is claimed is:

1. A system for imaging, comprising:

i) a biological sample comprising a fluorescent polypeptide expressed therein, wherein the fluorescent polypeptide comprises an excitation wavelength that causes the fluorescent polypeptide to emit a fluorescence signal comprising a tail portion in the near infrared (NIR) wavelength range of the electromagnetic spectrum and/or in the shortwave infrared (SWIR) wavelength range of electromagnetic spectrum;

ii) an excitation source configured to emit electromagnetic radiation comprising the excitation wavelength; and iii) a detector configured to detect the tail portion of the fluorescence signal emitted by of the fluorescent polypeptide, wherein said detector is configured to detect in the near infrared (NIR) wavelength range of the electromagnetic spectrum and/or in the shortwave infrared (SWIR) wavelength range of electromagnetic spectrum.

2. The system of claim 1, further comprising a computing device, wherein the detector outputs a detected tail portion signal from the fluorescent probe to the computing device.

3. The system of claim 2, wherein the computing device compares the detected fluorescence signal to an intensity threshold to a subject condition.

4. The system of claim 1, further comprising a display, wherein the detector is configured to outputs the detected tail portion of the fluorescence signal emitted by the fluorescent polypeptide to the display.

5. The system of claim 1, wherein said fluorescent polypeptide is excitable at a wavelength of less than about 800 nm.

6. The system of claim 1, wherein said fluorescent polypeptide comprises one or more of the following polypeptides:

i) a fluorescent polypeptide which is at least 60% or more identical to tdTomato polypeptide (SEQ ID NO: 1);

ii) a fluorescent polypeptide which is at least 60% or more identical to SMURF polypeptide (SEQ ID NO: 2);

iii) a fluorescent polypeptide which is at least 60% or more identical to iRFP720 polypeptide (SEQ ID NO: 3);

iv) a fluorescent polypeptide which is at least 60% or more identical to 22G (Dronpa) from *Echinophyllia* sp. SC22, Genbank ADE48854.1, v) a fluorescent polypeptide which is at least 60% or more identical to aceGFP from *Aequorea coerulescens*, Genbank AAN41637, vi) a fluorescent polypeptide which is at least 60% or more identical to amFP486 from *Anemonia majano*, Genbank AAF03371, vii) a fluorescent polypeptide which is at least 60% or more identical to anm2CP from Anthoathecata, Genbank AAR85352, viii) a fluorescent polypeptide which is at least 60% or more identical to avGFP (classic GFP) from *Aequorea victoria*, Genbank AAA27721, ix) a fluorescent polypeptide which is at least 60% or more identical to cFP484 from *Clavularia* sp., Genbank AAF03374, x) a fluorescent polypeptide which is at least 60% or more identical to dendFP from *Dendronephthya* sp., Genbank AAM10625, xi) a fluorescent polypeptide which is at least 60% or more identical to dfGFP from *Olindias formosus*, Genbank BBC28143, xii) a fluorescent polypeptide which is at least 60% or more identical to DrCBD from *Deinococcus radiodurans*, Genbank AE001825, xiii) a fluorescent polypeptide which is at least 60% or more identical to DsRed from *Discosoma* sp., Genbank AAF03369, xiv) a fluorescent polypeptide which is at least 60% or more identical to EosFP from *Lobophyllia hemprichii*, Genbank AAV54099, xv) a fluorescent polypeptide which is at least 60% or more identical to eqFP578 from *Entacmaea quadricolor*, Genbank H3JQU7, xvi) a fluorescent polypeptide which is at least 60% or more identical to eqFP611 from *Entacmaea quadricolor*, Genbank AAN05449, xvii) a fluorescent polypeptide which is at least 60% or more identical to HcRed from *Heteractis crispa*, Genbank Q95W85.1, xviii) a fluorescent polypeptide which is at least 60% or more identical to KikG from *Favia favus*, Genbank BAD95670.1, xix) a fluorescent polypeptide which is at least 60% or more identical to KO from *Verrillofungia concinna*, Genbank BAD24721, xx) a fluorescent polypeptide which is at least 60% or more identical to LanYFP from *Branchiostoma lanceolatum*, Genbank ACA48232, xxi) a fluorescent polypeptide which is at least 60% or more identical to SEQ ID NO: 4, xxii) a fluorescent polypeptide which is at least 60% or more identical to mRed7 having SEQ ID NO: 5, xxiii) a fluorescent polypeptide which is at least 60% or more identical to pR3784g from *Nostoc punctiforme*, Genbank WP_012410140, xxiv) a fluorescent polypeptide which is at least 60% or more identical to RpBphP1 from *Rhodopseudomonas palustris*, Genbank 5OY5_A, XXV) a fluorescent polypeptide which is at least 60% or more identical to RpBphP2 from *Rhodopseudomonas palustris*, Genbank WP_011158562, xxvi) a fluorescent polypeptide which is at least 60% or more identical to RpBphP6 from *Rhodopseudomonas palustris*, Genbank WP_011156523, xxvii) a fluorescent polypeptide which is at least 60% or more identical to TeAPCalpha from *Trichodesmium erythraeum* IMS101, Genbank CP000393.1, xxviii) a fluorescent polypeptide which is at least 60% or more identical to zFP538 from *Zoanthus* sp., Genbank AAF03373, xxix) a fluorescent polypeptide which is at least 60% or more identical to BphP AGP1 from *Agrobacterium tumefaciens*, Genbank F7UC55_RHIRD, xxx) a fluorescent polypeptide which is at least 60% or more identical to sGPC2 from *Acaryochloris* marina (Chee et al., Journal of Biomedical Optics 23 (10), 106006 (October 2018)), xxxi) a fluorescent polypeptide which is at least 60% or more identical to APCF2 from *Chroococcidiopsis thermalis*, Genbank WP_015153831, xxxii) a fluorescent polypeptide which is at least 60% or more identical to UnaG from *Anguilla japonica*, Genbank AB763906, xxxiii) a fluorescent polypeptide which is at least 60% or more identical to RRvT polypeptide (SEQ ID NO: 6), xxxiv) a fluorescent polypeptide which is at least 60% or more identical to tdTomato polypeptide (SEQ ID NO: 7), XXXV) a fluorescent polypeptide which is at least 60% or more identical to tdimer2(12) polypeptide (SEQ ID NO: 8), xxxvi) a fluorescent polypeptide which is at least 60% or more identical to pcDronpa2 polypeptide (SEQ ID NO: 9), xxxvii) a fluorescent polypeptide which is at least 60% or more identical to mScarlet polypeptide (SEQ ID NO: 10), xxxviii) a fluorescent polypeptide which is at least 60% or more identical to mKO kappa polypeptide (SEQ ID NO: 11), xxxix) a fluorescent polypeptide which is at least 60% or more identical to TurboRFP polypeptide (SEQ ID NO: 12), xl) a fluorescent polypeptide which is at least 60% or more identical to PsmOrange polypeptide (SEQ ID NO: 13), xli) a fluorescent polypeptide which is at least 60% or more identical to RFP611 polypeptide (SEQ ID NO: 14), xlii) a fluorescent polypeptide which is at least 60% or more identical to mRuby3 polypeptide (SEQ ID NO: 15), xliii) a fluorescent polypeptide which is at least 60% or more identical to vsfGFP-0 polypeptide (SEQ ID NO: 16), xliv) a fluorescent polypeptide which is at least 60% or more identical to bfloGFPa1 polypeptide (Bomati et al. (2014). Scientific Reports, 4 (1), 5469, doi: 10.1038/srep05469), xlv) a fluorescent polypeptide which is at least 60% or more identical to LanYFP polypeptide (SEQ ID NO: 17), xlvi) a fluorescent polypeptide which is at least 60% or more identical to dLanYFP polypeptide (SEQ ID NO: 18), xlvii) a fluorescent polypeptide which is at least 60% or more identical to dVFP polypeptide (SEQ ID NO: 19), xlviii) a fluorescent polypeptide which is at least 60% or more identical to ccalYFP polypeptide (SEQ ID NO: 20), xlix) a fluorescent polypeptide which is at least 60% or more identical to efasGFP polypeptide (SEQ ID NO: 21), l) A fluorescent polypeptide which is at least 60% or more identical to pcDronpa (green) polypeptide (SEQ ID NO: 22), li) a fluorescent polypeptide which is at least 60% or more identical to aeurGFP polypeptide (SEQ ID NO: 23), lii) a fluorescent polypeptide which is at least 60% or more identical to miRFP720 polypeptide (SEQ ID NO: 24), liii) a fluorescent polypeptide which is at least 60% or more identical to iRFP720 polypeptide (SEQ ID NO: 25), liv) a fluorescent polypeptide which is at least 60% or more identical to Wi-Phy polypeptide (SEQ ID NO: 26), lv) a fluorescent polypeptide which is at least 60% or more identical to SNIFP polypeptide (SEQ ID NO: 27), lvi) a fluorescent polypeptide which is at least 60% or more identical to iFP2.0 polypeptide (SEQ ID NO: 28), lvii) a fluorescent polypeptide which is at least 60% or more identical to iRFP713 polypeptide (SEQ ID NO: 29), lviii) a fluorescent polypeptide which is at least 60% or more identical to iFP1.4 polypeptide (SEQ ID NO: 30), lix) a fluorescent polypeptide which is at least 60% or more identical to mIFP polypeptide (SEQ ID NO: 31), lx) a fluorescent polypeptide which is at least 60% or more identical to miRFP709 polypeptide (SEQ ID NO: 32), lxi) a fluorescent polypeptide which is at least 60% or more identical to miRFP polypeptide (SEQ ID NO: 33), lxii) a fluorescent polypeptide which is at least 60% or more identical to M35NA polypeptide (SEQ ID NO: 34), lxiii) a fluorescent polypeptide which is at least 60% or more identical to smURFP polypeptide (SEQ ID NO: 35), lxiv) a fluorescent polypeptide which is at least 60% or more identical to TDsmURFP polypeptide (SEQ ID NO: 36), lxv) a fluorescent polypeptide which is at least 60% or more identical to LanFP2 polypeptide (SEQ ID NO: 37), lxvi) a fluorescent polypeptide which is at least 60% or more identical to HcRed-Tandem polypeptide (SEQ ID NO: 38), lxvii) a fluorescent polypeptide which is at least 60% or more identical to Skylan-S polypeptide (SEQ ID NO: 39), lxviii) a fluorescent polypeptide which is at least 60% or more identical to VFP polypeptide (SEQ ID NO: 40), lxix) a fluorescent polypeptide which is at least 60% or more identical to GFPxm163 polypeptide (SEQ ID NO: 41), lxx) a fluorescent polypeptide which is at least 60% or more identical to PlamGFP polypeptide (SEQ ID NO: 42), lxxi) a fluorescent polypeptide which is at least 60% or more identical to sarcGFP polypeptide (SEQ ID NO: 43), lxxii) a fluorescent polypeptide which is at least 60% or more identical to psamCFP polypeptide (SEQ ID NO: 44), lxxiii) a fluorescent polypeptide which is at least 60% or more identical to GFPxm18 polypeptide (SEQ ID NO: 45), lxxiv) a fluorescent polypeptide which is at least 60% or more identical to Gamillus 0.2 polypeptide (SEQ ID NO: 46), lxxv) a fluorescent polypeptide which is at least 60% or more identical to eGFP polypeptide (SEQ ID NO: 47), lxxvi) a fluorescent polypeptide which is at least 60% or more identical to eYFP polypeptide (SEQ ID NO: 48), lxxvii) a fluorescent polypeptide which is at least 60% or more identical to Venus polypeptide (SEQ ID NO: 49), lxxviii) a fluorescent polypeptide which is at least 60% or more identical to mOrange2 polypeptide (SEQ ID NO: 50), lxxix) a fluorescent polypeptide which is at least 60% or more identical to mCherry polypeptide (SEQ ID NO: 51), lxxx) a fluorescent polypeptide which is at least 60% or more identical to mTagBFP polypeptide (SEQ ID NO: 52), lxxxi) a fluorescent polypeptide which is at least 60% or more identical to ZsGreen polypeptide (SEQ ID NO: 53), lxxxii) a fluorescent polypeptide which is at least 60% or more identical to YPet polypeptide (SEQ ID NO: 54), lxxxiii) a fluorescent polypeptide which is at least 60% or more identical to mCitrine polypeptide (SEQ ID NO: 55), lxxxiv) a fluorescent polypeptide which is at least 60% or more identical to CFP polypeptide (SEQ ID NO: 56), lxxxv) a fluorescent polypeptide which is at least 60% or more identical to eCFP polypeptide (SEQ ID NO: 57), lxxxvi) a fluorescent polypeptide which is at least 60% or more identical to GFP polypeptide (SEQ ID NO: 58), lxxxvii) a fluorescent fragment of any one of (i)-(lxxxvi).

7. The system of claim 1, wherein said sample expresses two or more different fluorescent polypeptides.

8. The system of claim 1, wherein said system is a system for multiplexed and/or multicolor imaging of said biological sample.

9. The system of claim 1, wherein:
- the excitation source comprises a first laser light source configured to operate at a first wavelength;
- and at least a second laser light source configured to operate at a second wavelength; and
- the system further comprises a control unit operably coupled to the first laser light source, the second laser light source and the detector, wherein the control unit is configured to control the first laser light source to provide a first excitation light pulse/s and to control the second laser light source to provide a second excitation light pulse/s in sequential manner;
- wherein the control unit is further operably coupled to the detector to switch detector in a sequential manner between a first state during which the imaging device is responsive to a first electromagnetic radiation and a second state during which the imaging device is responsive to a second electromagnetic radiation, wherein said first and second electromagnetic radiations are not identical; and
- wherein the system is configured such that the switching of the imaging device into the first state is triggered by the provision of the light pulse/s.

10. A system according to claim 1, wherein the system is configured to perform one or more of the following:
- i) an in vivo, ex vivo and/or in vitro method;
- ii) a diagnostic, therapeutic, surgical and/or screening method;
- iii) a tissue engineering and/or transplantation method;
- iv) a three-dimensional (3D) bioprinting method;
- v) a real-time imaging method;
- vi) a fluorescence imaging method;
- vii) a multicolor real-time image acquisition method;
- viii) a method for reduction of melanin absorption in the SWIR;
- ix) a method for a non-invasive imaging of tissues and/or organisms in the presence of melanin.

11. A method for imaging a biological sample comprising:
- i) exposing at least a portion of said biological sample comprising a fluorescent polypeptide expressed therein, wherein the fluorescent polypeptide comprises an excitation wavelength that causes the fluorescent polypeptide to emit a fluorescence signal comprising a tail portion in the near infrared (NIR) wavelength range of the electromagnetic spectrum and/or in the short-wave infrared (SWIR) wavelength range of electromagnetic spectrum; and
- ii) detecting the tail portion of the fluorescence signal emitted by the fluorescent polypeptide, wherein said detecting is carried out in the near infrared (NIR) wavelength range of the electromagnetic spectrum and/or in the shortwave infrared (SWIR) wavelength range of the electromagnetic spectrum.

12. The method of claim 11, wherein said fluorescent polypeptide is excitable at a wavelength of less than about 800 nm.

13. The method of claim 11, wherein said fluorescent polypeptide comprises one or more of the following polypeptides:
- i) a fluorescent polypeptide which is at least 60% or more identical to tdTomato polypeptide (SEQ ID NO: 1);
- ii) a fluorescent polypeptide which is at least 60% or more identical to SMURF polypeptide (SEQ ID NO: 2);
- iii) a fluorescent polypeptide which is at least 60% or more identical to iRFP720 polypeptide (SEQ ID NO: 3);
- iv) a fluorescent polypeptide which is at least 60% or more identical to 22G (Dronpa) from *Echinophyllia* sp. SC22, Genbank ADE48854.1,
- v) a fluorescent polypeptide which is at least 60% or more identical to aceGFP from *Aequorea coerulescens*, Genbank AAN41637,
- vi) a fluorescent polypeptide which is at least 60% or more identical to amFP486 from *Anemonia majano*, Genbank AAF03371,
- vii) a fluorescent polypeptide which is at least 60% or more identical to anm2CP from Anthoathecata, Genbank AAR85352,
- viii) a fluorescent polypeptide which is at least 60% or more identical to avGFP (classic GFP) from *Aequorea victoria*, Genbank AAA27721,
- ix) a fluorescent polypeptide which is at least 60% or more identical to cFP484 from *Clavularia* sp., Genbank AAF03374,
- x) a fluorescent polypeptide which is at least 60% or more identical to dendFP from *Dendronephthya* sp., Genbank AAM10625,
- xi) a fluorescent polypeptide which is at least 60% or more identical to dfGFP from *Olindias formosus*, Genbank BBC28143,
- xii) a fluorescent polypeptide which is at least 60% or more identical to DrCBD from *Deinococcus radiodurans*, Genbank AE001825,
- xiii) a fluorescent polypeptide which is at least 60% or more identical to DsRed from *Discosoma* sp., Genbank AAF03369,
- xiv) a fluorescent polypeptide which is at least 60% or more identical to EosFP from *Lobophyllia hemprichii*, Genbank AAV54099,
- xv) a fluorescent polypeptide which is at least 60% or more identical to eqFP578 from *Entacmaea quadricolor*, Genbank H3JQU7,
- xvi) a fluorescent polypeptide which is at least 60% or more identical to eqFP611 from *Entacmaea quadricolor*, Genbank AAN05449,
- xvii) a fluorescent polypeptide which is at least 60% or more identical to HcRed from *Heteractis crispa*, Genbank Q95W85.1,
- xviii) a fluorescent polypeptide which is at least 60% or more identical to KikG from *Favia favus*, Genbank BAD95670.1,
- xix) a fluorescent polypeptide which is at least 60% or more identical to KO from *Verrillofungia concinna*, Genbank BAD24721,
- xx) a fluorescent polypeptide which is at least 60% or more identical to Lan YFP from *Branchiostoma lanceolatum*, Genbank ACA48232,
- xxi) a fluorescent polypeptide which is at least 60% or more identical to SEQ ID NO: 4,
- xxii) a fluorescent polypeptide which is at least 60% or more identical to mRed7 having SEQ ID NO: 5,
- xxiii) a fluorescent polypeptide which is at least 60% or more identical to pR3784g from *Nostoc punctiforme*, Genbank WP_012410140,
- xxiv) a fluorescent polypeptide which is at least 60% or more identical to RpBphP1 from *Rhodopseudomonas palustris*, Genbank 5OY5_A,
- xxv) a fluorescent polypeptide which is at least 60% or more identical to RpBphP2 from *Rhodopseudomonas palustris*, Genbank WP_011158562, xxvi) a fluorescent polypeptide which is at least 60% or more identical to RpBphP6 from *Rhodopseudomonas palustris*, Genbank WP_011156523, xxvii) a fluorescent polypeptide which is at least 60% or more identical to TeAPCalpha from *Trichodesmium erythraeum* IMS101, Genbank CP000393.1, xxviii) a fluorescent polypeptide which is at least 60% or more identical to zFP538 from *Zoanthus* sp., Genbank AAF03373, xxix) a fluorescent polypeptide which is at least 60% or more identical to BphP AGP1 from *Agrobacterium tumefaciens*, Genbank F7UC55_RHIRD, xxx) a fluorescent polypeptide which is at least 60% or more identical to sGPC2 from *Acaryochloris* marina (Chee et al., Journal of Biomedical Optics 23 (10), 106006 (October 2018)), xxxi) a fluorescent polypeptide which is at least 60% or more identical to APCF2 from *Chroococcidiopsis thermalis*, Genbank WP_015153831, xxxii) a fluorescent polypeptide which is at least 60% or more identical to UnaG from *Anguilla japonica*, Genbank AB763906, xxxiii) a fluorescent polypeptide which is at least 60% or more identical to RRvT polypeptide (SEQ ID NO: 6), xxxiv) a fluorescent polypeptide which is at least 60% or more identical to tdTomato polypeptide (SEQ ID NO: 7), xxxv) a fluorescent polypeptide which is at least 60% or more identical to tdimer2 (12) polypeptide (SEQ ID NO: 8), xxxvi) a fluorescent polypeptide which is at least 60% or more identical to pcDronpa2 polypeptide (SEQ ID NO: 9), xxxvii) a fluorescent polypeptide which is at least 60% or more identical to mScarlet polypeptide (SEQ ID NO: 10), xxxviii) a fluorescent polypeptide which is at least 60% or more identical to mKO kappa polypeptide (SEQ ID NO: 11), xxxix) a fluorescent polypeptide which is at least 60% or more identical to TurboRFP polypeptide (SEQ ID NO: 12), xl) a fluorescent polypeptide which is at least 60% or more identical to PsmOrange polypeptide (SEQ ID NO: 13), xli) a fluorescent polypeptide which is at least 60% or more identical to RFP611 polypeptide (SEQ ID NO: 14), xlii) a fluorescent polypeptide which is at least 60% or more identical to mRuby3 polypeptide (SEQ ID NO: 15), xliii) a fluorescent polypeptide which is at least 60% or more identical to vsfGFP-0 polypeptide (SEQ ID NO: 16), xliv) a fluorescent polypeptide which is at least 60% or more identical to bfloGFPa1 polypeptide (Bomati et al. (2014). Scientific Reports, 4 (1), 5469. doi: 10.1038/srep05469), xlv) a fluorescent polypeptide which is at least 60% or more identical to Lan YFP polypeptide (SEQ ID NO: 17), xlvi) a fluorescent polypeptide which is at least 60% or more identical to dLanYFP polypeptide (SEQ ID NO: 18), xlvii) a fluorescent polypeptide which is at least 60% or more identical to dVFP polypeptide (SEQ ID NO: 19), xlviii) a fluorescent polypeptide which is at least 60% or more identical to ccalYFP polypeptide (SEQ ID NO: 20), xlix) a fluorescent polypeptide which is at least 60% or more identical to efasGFP polypeptide (SEQ ID NO: 21), l) A fluorescent polypeptide which is at least 60% or more identical to pcDronpa (green) polypeptide (SEQ ID NO: 22), li) a fluorescent polypeptide which is at least 60% or more identical to aeurGFP polypeptide (SEQ ID NO: 23), lii) a fluorescent polypeptide which is at least 60% or more identical to miRFP720 polypeptide (SEQ ID NO: 24), liii) a fluorescent polypeptide which is at least 60% or more identical to iRFP720 polypeptide (SEQ ID NO: 25), liv) a fluorescent polypeptide which is at least 60% or more identical to Wi-Phy polypeptide (SEQ ID NO: 26), lv) a fluorescent polypeptide which is at least 60% or more identical to SNIFP polypeptide (SEQ ID NO: 27), lvi) a fluorescent polypeptide which is at least 60% or more identical to iFP2.0 polypeptide (SEQ ID NO: 28), lvii) a fluorescent polypeptide which is at least 60% or more identical to iRFP713 polypeptide (SEQ ID NO: 29), lviii) a fluorescent polypeptide which is at least 60% or more identical to iFP1.4 polypeptide (SEQ ID NO: 30), lix) a fluorescent polypeptide which is at least 60% or more identical to mIFP polypeptide (SEQ ID NO: 31), lx) a fluorescent polypeptide which is at least 60% or more identical to miRFP709 polypeptide (SEQ ID NO: 32), lxi) a fluorescent polypeptide which is at least 60% or more identical to miRFP polypeptide (SEQ ID NO: 33), lxii) a fluorescent polypeptide which is at least 60% or more identical to M35NA polypeptide (SEQ ID NO: 34), lxiii) a fluorescent polypeptide which is at least 60% or more identical to smURFP polypeptide (SEQ ID NO: 35), lxiv) a fluorescent polypeptide which is at least 60% or more identical to TDsmURFP polypeptide (SEQ ID NO: 36), lxv) a fluorescent polypeptide which is at least 60% or more identical to LanFP2 polypeptide (SEQ ID NO: 37), lxvi) a fluorescent polypeptide which is at least 60% or more identical to HcRed-Tandem polypeptide (SEQ ID NO: 38), lxvii) a fluorescent polypeptide which is at least 60% or more identical to Skylan-S polypeptide (SEQ ID NO: 39), lxviii) a fluorescent polypeptide which is at least 60% or more identical to VFP polypeptide (SEQ ID NO: 40), lxix) a fluorescent polypeptide which is at least 60% or more identical to GFPxm163 polypeptide (SEQ ID NO: 41), lxx) a fluorescent polypeptide which is at least 60% or more identical to PlamGFP polypeptide (SEQ ID NO: 42), lxxi) a fluorescent polypeptide which is at least 60% or more identical to sarcGFP polypeptide (SEQ ID NO: 43), lxxii) a fluorescent polypeptide which is at least 60% or more identical to psamCFP polypeptide (SEQ ID NO: 44), lxxiii) a fluorescent polypeptide which is at least 60% or more identical to GFPxm18 polypeptide (SEQ ID NO: 45), lxxiv) a fluorescent polypeptide which is at least 60% or more identical to Gamillus 0.2 polypeptide (SEQ ID NO: 46), lxxv) a fluorescent polypeptide which is at least 60% or more identical to eGFP polypeptide (SEQ ID NO: 47), lxxvi) a fluorescent polypeptide which is at least 60% or more identical to eYFP polypeptide (SEQ ID NO: 48), lxxvii) a fluorescent polypeptide which is at least 60% or more identical to Venus polypeptide (SEQ ID NO: 49), lxxviii) a fluorescent polypeptide which is at least 60% or more identical to mOrange2 polypeptide (SEQ ID NO: 50), lxxix) a fluorescent polypeptide which is at least 60% or more identical to mCherry polypeptide (SEQ ID NO: 51), lxxx) a fluorescent polypeptide which is at least 60% or more identical to mTagBFP polypeptide (SEQ ID NO: 52), lxxxi) a fluorescent polypeptide which is at least 60% or more identical to ZsGreen polypeptide (SEQ ID NO: 53), lxxxii) a fluorescent polypeptide which is at least 60% or more identical to YPet polypeptide (SEQ ID NO: 54), lxxxiii) a fluorescent polypeptide which is at least 60% or more identical to mCitrine polypeptide (SEQ ID NO: 55), lxxxiv) a fluorescent polypeptide which is at least 60% or more identical to CFP polypeptide (SEQ ID NO: 56), lxxxv) a fluorescent polypeptide which is at least 60% or more identical to eCFP polypeptide (SEQ ID NO: 57), lxxxvi) a fluorescent polypeptide which is at least 60% or more identical to GFP polypeptide (SEQ ID NO: 58), lxxxvii) a fluorescent fragment of any one of (i)-(Ixxxvi).

14. The method of claim 11, wherein said fluorescent probe comprises two or more different fluorescent polypeptides, preferably said two or more different fluorescent polypeptides are according.

15. The method of claim 11, wherein said method is the method for multiplexed and/or multicolor imaging of said biological sample.

16. The method of claim 11, wherein:

the at least a portion of said biological sample comprising a fluorescent polypeptide expressed therein further comprises a second fluorescent polypeptide expressed therein, said suitable excitation source is configured to provide a first light pulse/s having the excitation wavelength causing the fluorescent polypeptide in the portion of said biological sample to emit the fluorescence signal, and at least a second light pulse/s having a second wavelength which is different from the first wavelength configured to cause the second fluorescent polypeptide in the portion of said biological sample to emit a second fluorescence signal comprising a second tail portion in the near infrared (NIR) wavelength range of the electromagnetic spectrum and/or in the shortwave infrared (SWIR) wavelength range of electromagnetic spectrum;

wherein the first light pulse/s and the second (and/or subsequent) light pulse/s are provided sequentially;

iii) detecting the tail portion of the fluorescent signal and the second fluorescence signal by an imaging device, wherein the peak emission wavelength of at least one polypeptide in the portion of said biological sample lies outside of the detection range of the imaging device, the detection process including:

aa) switching the imaging device, in a sequential manner, between a first configuration during which the imaging device is responsive to a first electromagnetic radiation and a second configuration during which the imaging device is responsive to a second electromagnetic radiation, wherein said first and second electromagnetic radiations are not identical; wherein the switching of the first configuration is triggered by the provision of the light pulse.

* * * * *

SEQUENCE LISTING

```
<160> NUMBER OF SEQ ID NOS: 61

<210> SEQ ID NO 1
<211> LENGTH: 476
<212> TYPE: PRT
<213> ORGANISM: Artificial Sequence
<220> FEATURE:
<223> OTHER INFORMATION: Tandem-dimer red fluorescent protein [synthetic
      construct]. GenBank Accession Number: AAV52169.1

<400> SEQUENCE: 1

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110
```

```
Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
    370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475
```

<210> SEQ ID NO 2
<211> LENGTH: 133
<212> TYPE: PRT
<213> ORGANISM: Artificial Sequence
<220> FEATURE:
<223> OTHER INFORMATION: far-red fluorescent protein smURFP [synthetic construct]. GenBank Accession Number: ANW47198.1

<400> SEQUENCE: 2

```
Met Ala Lys Thr Ser Glu Gln Arg Val Asn Ile Ala Thr Leu Leu Thr
1               5                   10                  15

Glu Asn Lys Lys Lys Ile Val Asp Lys Ala Ser Gln Asp Leu Trp Arg
            20                  25                  30

Arg His Pro Asp Leu Ile Ala Pro Gly Gly Ile Ala Phe Ser Gln Arg
        35                  40                  45

Asp Arg Ala Leu Cys Leu Arg Asp Tyr Gly Trp Phe Leu His Leu Ile
    50                  55                  60

Thr Phe Cys Leu Leu Ala Gly Asp Lys Gly Pro Ile Glu Ser Ile Gly
65                  70                  75                  80

Leu Ile Ser Ile Arg Glu Met Tyr Asn Ser Leu Gly Val Pro Val Pro
                85                  90                  95

Ala Met Met Glu Ser Ile Arg Cys Leu Lys Glu Ala Ser Leu Ser Leu
            100                 105                 110

Leu Asp Glu Glu Asp Ala Asn Glu Thr Ala Pro Tyr Phe Asp Tyr Ile
        115                 120                 125

Ile Lys Ala Met Ser
    130
```

<210> SEQ ID NO 3
<211> LENGTH: 316
<212> TYPE: PRT
<213> ORGANISM: Artificial Sequence
<220> FEATURE:
<223> OTHER INFORMATION: Near-infrared fluorescent protein iRFP720 [synthetic construct]. GenBank Accession Number: AGN32866.1

<400> SEQUENCE: 3

```
Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Ser Val Ile Ala Glu Asp Arg Cys Ala Glu Val Glu Ser
            180                 185                 190

Lys Leu Gly Leu His Tyr Pro Ala Ser Phe Ile Pro Ala Gln Ala Arg
        195                 200                 205
```

```
Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Asn His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Glu Leu Val Ala
    290                 295                 300

Gln Val Leu Ala Trp Gln Ile Gly Val Met Glu Glu
305                 310                 315


<210> SEQ ID NO 4
<211> LENGTH: 221
<212> TYPE: PRT
<213> ORGANISM: Montipora sp. 20

<400> SEQUENCE: 4

Met Ser Val Ile Ala Lys Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Leu Ser Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met His Phe Glu
                85                  90                  95

Asp Gly Ala Val Cys Thr Val Ser Asn Asp Ser Ser Ile Gln Gly Asn
            100                 105                 110

Cys Phe Ile Tyr Asn Val Lys Ile Ser Gly Val Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly Gly His Tyr Leu Cys Glu Phe Lys Ser Thr
                165                 170                 175

Tyr Lys Ala Lys Lys Pro Val Arg Met Pro Gly Tyr His Tyr Val Asp
            180                 185                 190

Arg Lys Leu Asp Val Thr Ser His Asn Lys Asp Tyr Thr Phe Val Glu
        195                 200                 205

Gln Cys Glu Ile Ser Ile Ala Arg His Ser Leu Leu Gly
    210                 215                 220


<210> SEQ ID NO 5
<211> LENGTH: 232
<212> TYPE: PRT
<213> ORGANISM: Artificial Sequence
<220> FEATURE:
<223> OTHER INFORMATION: mRed7
```

<400> SEQUENCE: 5

```
Met Val Ser Lys Gly Glu Glu Val Ile Lys Glu Phe Met Gln Phe Lys
1               5                   10                  15

Val His Met Glu Gly Ser Val Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Phe Lys Leu Ser Phe Pro Glu Gly Phe Lys Trp Glu Arg
                85                  90                  95

Val Met Asn Phe Glu Asp Gly Gly Ala Val Thr Val Thr Gln Asp Ser
            100                 105                 110

Ser Leu Glu Asp Gly Thr Leu Ile Tyr Lys Val Lys Phe Arg Gly Thr
        115                 120                 125

Asn Phe Pro Pro Asp Gly Pro Val Met Gln Lys Lys Thr Met Gly Trp
    130                 135                 140

Glu Pro Ser Thr Glu Arg Leu Tyr Pro Gln Asp Gly Val Leu Lys Gly
145                 150                 155                 160

Glu Ile Ser Gln Ala Leu Lys Leu Lys Asp Gly Gly His Tyr Leu Val
                165                 170                 175

Asp Phe Lys Thr Thr Tyr Met Ala Lys Lys Pro Val Gln Leu Pro Gly
            180                 185                 190

Ala Tyr Asn Val Asp Thr Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Gly Met Asp Glu Leu Tyr Lys
225                 230
```

<210> SEQ ID NO 6
<211> LENGTH: 478
<212> TYPE: PRT
<213> ORGANISM: artificial
<220> FEATURE:
<223> OTHER INFORMATION: fluorescent protein RRvT

<400> SEQUENCE: 6

```
Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Asn Val Lys Met Arg Gly Thr
```

```
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Tyr Gly Met Asp Glu Leu Tyr Lys Gly Ser Thr Gly Ser Gly
225                 230                 235                 240

Ser Ser Gly Pro Met Val Ser Lys Gly Glu Glu Ala Ile Lys Glu Phe
                245                 250                 255

Met Arg Phe Lys Val Ser Met Glu Gly Ser Met Asn Gly His Glu Phe
            260                 265                 270

Glu Ile Glu Gly Glu Gly Glu Gly Arg Pro Tyr Glu Gly Thr Gln Thr
        275                 280                 285

Ala Lys Leu Lys Val Thr Lys Gly Gly Pro Leu Pro Phe Ala Trp Asp
    290                 295                 300

Ile Leu Ser Pro Gln Phe Met Tyr Gly Ser Lys Ala Tyr Val Lys His
305                 310                 315                 320

Pro Ala Asp Ile Pro Asp Tyr Lys Lys Leu Ser Phe Pro Glu Gly Phe
                325                 330                 335

Arg Trp Glu Arg Val Met Asn Phe Glu Asp Gly Gly Leu Val Thr Val
            340                 345                 350

Thr Gln Asp Ser Ser Ile Gln Asp Gly Thr Leu Ile Tyr Lys Val Lys
        355                 360                 365

Val Arg Gly Thr Asn Phe Pro Pro Asp Gly Pro Val Met Gln Lys Lys
    370                 375                 380

Thr Met Gly Trp Glu Ala Ser Thr Glu Arg Leu Tyr Pro Arg Asp Gly
385                 390                 395                 400

Val Leu Lys Gly Glu Ile His Gln Ala Leu Lys Leu Lys Asp Gly Gly
                405                 410                 415

His Tyr Leu Val Glu Phe Lys Thr Ile Tyr Met Ala Lys Lys Pro Val
            420                 425                 430

Gln Leu Pro Gly Tyr Tyr Tyr Val Asp Thr Lys Leu Asp Ile Thr Ser
        435                 440                 445

His Asn Glu Asp Tyr Thr Val Val Glu Gln Tyr Glu Arg Ser Glu Gly
    450                 455                 460

Arg His His Leu Phe Leu Tyr Gly Met Asp Glu Leu Tyr Lys
465                 470                 475


<210> SEQ ID NO 7
<211> LENGTH: 476
<212> TYPE: PRT
<213> ORGANISM: artificial
<220> FEATURE:
<223> OTHER INFORMATION: fluorescent protein tdTomato

<400> SEQUENCE: 7

Met Val Ser Lys Gly Glu Glu Val Ile Lys Glu Phe Met Arg Phe Lys
```

-continued

```
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
    370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430
```

```
Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475
```

<210> SEQ ID NO 8
<211> LENGTH: 464
<212> TYPE: PRT
<213> ORGANISM: artificial
<220> FEATURE:
<223> OTHER INFORMATION: fluorescent protein tdimer2(12)

<400> SEQUENCE: 8

```
Met Val Ala Ser Ser Glu Asp Val Ile Lys Glu Phe Met Arg Phe Lys
1               5                   10                  15

Val Arg Met Glu Gly Ser Val Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Gln Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Thr Leu Ile Tyr Lys Val Lys Phe Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Val Ile Lys Glu Phe Met Arg Phe Lys Val Arg
                245                 250                 255

Met Glu Gly Ser Val Asn Gly His Glu Phe Glu Ile Glu Gly Glu Gly
            260                 265                 270

Glu Gly Arg Pro Tyr Glu Gly Thr Gln Thr Ala Lys Leu Lys Val Thr
        275                 280                 285

Lys Gly Gly Pro Leu Pro Phe Ala Trp Asp Ile Leu Ser Pro Gln Phe
    290                 295                 300

Gln Tyr Gly Ser Lys Ala Tyr Val Lys His Pro Ala Asp Ile Pro Asp
305                 310                 315                 320
```

```
Tyr Lys Lys Leu Ser Phe Pro Glu Gly Phe Lys Trp Glu Arg Val Met
                325                 330                 335

Asn Phe Glu Asp Gly Gly Val Val Thr Val Thr Gln Asp Ser Ser Leu
            340                 345                 350

Gln Asp Gly Thr Leu Ile Tyr Lys Val Lys Phe Arg Gly Thr Asn Phe
        355                 360                 365

Pro Pro Asp Gly Pro Val Met Gln Lys Lys Thr Met Gly Trp Glu Ala
    370                 375                 380

Ser Thr Glu Arg Leu Tyr Pro Arg Asp Gly Val Leu Lys Gly Glu Ile
385                 390                 395                 400

His Gln Ala Leu Lys Leu Lys Asp Gly Gly His Tyr Leu Val Glu Phe
                405                 410                 415

Lys Thr Ile Tyr Met Ala Lys Lys Pro Val Gln Leu Pro Gly Tyr Tyr
            420                 425                 430

Tyr Val Asp Thr Lys Leu Asp Ile Thr Ser His Asn Glu Asp Tyr Thr
        435                 440                 445

Ile Val Glu Gln Tyr Glu Arg Ser Glu Gly Arg His His Leu Phe Leu
    450                 455                 460
```

```
<210> SEQ ID NO 9
<211> LENGTH: 224
<212> TYPE: PRT
<213> ORGANISM: artificial
<220> FEATURE:
<223> OTHER INFORMATION: fluoresecent protein pcDropna2

<400> SEQUENCE: 9

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Ala Phe His Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Ile Ala Thr Asn Asp Ile Thr Leu Asp Gly Asp
            100                 105                 110

Cys Tyr Ile Asn Glu Ile Arg Phe Asp Gly Val Asn Phe Pro Ala Asn
        115                 120                 125

Gly Pro Val Met Gln Lys Arg Thr Val Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

His His Ile Glu Ile Lys Ser His Asp Lys Asp Tyr Ser Asn Val Asn
        195                 200                 205

Leu His Glu His Ala Glu Ala His Ser Gly Leu Pro Arg Gln Ala Lys
    210                 215                 220
```

<210> SEQ ID NO 10
<211> LENGTH: 232
<212> TYPE: PRT
<213> ORGANISM: artificial
<220> FEATURE:
<223> OTHER INFORMATION: fluorescent protein mScarlet

<400> SEQUENCE: 10

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ser Trp Asp Ile Leu Ser Pro
    50                  55                  60

Gln Phe Met Tyr Gly Ser Arg Ala Phe Thr Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Gly Met Asp Glu Leu Tyr Lys
225                 230

<210> SEQ ID NO 11
<211> LENGTH: 218
<212> TYPE: PRT
<213> ORGANISM: artificial
<220> FEATURE:
<223> OTHER INFORMATION: fluorescent protein mKO kappa

<400> SEQUENCE: 11

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp

```
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser
    210                 215


<210> SEQ ID NO 12
<211> LENGTH: 231
<212> TYPE: PRT
<213> ORGANISM: artificial
<220> FEATURE:
<223> OTHER INFORMATION: fluorescent protein TurboRFP

<400> SEQUENCE: 12

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Lys Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Lys Ala Phe Ile Asn His Thr Gln Gly Ile Pro Asp Phe Phe
65                  70                  75                  80

Lys Gln Ser Phe Pro Glu Gly Phe Thr Trp Glu Arg Ile Thr Thr Tyr
                85                  90                  95

Glu Asp Gly Gly Val Leu Thr Ala Thr Gln Asp Thr Ser Phe Gln Asn
            100                 105                 110

Gly Cys Ile Ile Tyr Asn Val Lys Ile Asn Gly Val Asn Phe Pro Ser
        115                 120                 125

Asn Gly Pro Val Met Gln Lys Lys Thr Arg Gly Trp Glu Ala Asn Thr
    130                 135                 140

Glu Met Leu Tyr Pro Ala Asp Gly Gly Leu Arg Gly His Ser Gln Met
145                 150                 155                 160

Ala Leu Lys Leu Val Gly Gly Gly Tyr Leu His Cys Ser Phe Lys Thr
                165                 170                 175

Thr Tyr Arg Ser Lys Lys Pro Ala Lys Asn Leu Lys Met Pro Gly Phe
            180                 185                 190

His Phe Val Asp His Arg Leu Glu Arg Ile Lys Glu Ala Asp Lys Glu
        195                 200                 205

Thr Tyr Val Glu Gln His Glu Met Ala Val Ala Lys Tyr Cys Asp Leu
```

```
    210                 215                 220

Pro Ser Lys Leu Gly His Arg
225                 230


<210> SEQ ID NO 13
<211> LENGTH: 236
<212> TYPE: PRT
<213> ORGANISM: artificial
<220> FEATURE:
<223> OTHER INFORMATION: fluorescent protein PSmOrange

<400> SEQUENCE: 13

Met Val Ser Lys Gly Glu Glu Asn Asn Met Ala Ile Ile Lys Glu Phe
1               5                   10                  15

Met Arg Phe Lys Val Arg Met Glu Gly Thr Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Leu Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Tyr Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Met Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Arg Met Arg Leu Lys Leu Lys Asp Gly Gly
                165                 170                 175

His Tyr Thr Ser Glu Val Lys Thr Thr Tyr Lys Ala Lys Lys Ser Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235


<210> SEQ ID NO 14
<211> LENGTH: 231
<212> TYPE: PRT
<213> ORGANISM: artificial
<220> FEATURE:
<223> OTHER INFORMATION: fluorescent protein RFP611

<400> SEQUENCE: 14

Met Asn Ser Leu Ile Lys Glu Asn Met Arg Met Met Val Val Met Glu
1               5                   10                  15

Gly Ser Val Asn Gly Tyr Gln Phe Lys Cys Thr Gly Glu Gly Asp Gly
            20                  25                  30

Asn Pro Tyr Met Gly Thr Gln Thr Met Arg Ile Lys Val Val Glu Gly
        35                  40                  45
```

-continued

```
Gly Pro Leu Pro Phe Ala Phe Asp Val Leu Ala Thr Ser Phe Met Tyr
    50                  55                  60

Gly Ser Lys Thr Phe Ile Lys His Thr Lys Gly Ile Pro Asp Phe Phe
65                  70                  75                  80

Lys Gln Ser Phe Pro Glu Gly Phe Thr Trp Glu Arg Val Thr Arg Tyr
                85                  90                  95

Glu Asp Gly Gly Val Ile Thr Val Met Gln Asp Thr Ser Leu Glu Asp
            100                 105                 110

Gly Cys Leu Val Tyr His Ala Lys Val Thr Gly Val Asn Phe Pro Ser
        115                 120                 125

Asn Gly Ala Val Met Gln Lys Lys Thr Lys Gly Trp Glu Pro Asn Thr
    130                 135                 140

Glu Met Leu Tyr Pro Ala Asp Gly Gly Leu Arg Gly Tyr Ser Gln Met
145                 150                 155                 160

Ala Leu Asn Val Asp Gly Gly Gly Tyr Leu Ser Cys Ser Phe Glu Thr
                165                 170                 175

Thr Tyr Arg Ser Lys Lys Thr Val Glu Asn Phe Lys Met Pro Gly Phe
            180                 185                 190

His Phe Val Asp His Arg Leu Glu Arg Leu Glu Glu Ser Asp Lys Glu
        195                 200                 205

Met Phe Val Val Gln His Glu His Ala Val Ala Lys Phe Cys Asp Leu
    210                 215                 220

Pro Ser Lys Leu Gly Arg Leu
225                 230


<210> SEQ ID NO 15
<211> LENGTH: 237
<212> TYPE: PRT
<213> ORGANISM: artificial
<220> FEATURE:
<223> OTHER INFORMATION: fluorescent protein mRuby3

<400> SEQUENCE: 15

Met Val Ser Lys Gly Glu Glu Leu Ile Lys Glu Asn Met Arg Met Lys
1               5                   10                  15

Val Val Met Glu Gly Ser Val Asn Gly His Gln Phe Lys Cys Thr Gly
            20                  25                  30

Glu Gly Glu Gly Arg Pro Tyr Glu Gly Val Gln Thr Met Arg Ile Lys
        35                  40                  45

Val Ile Glu Gly Gly Pro Leu Pro Phe Ala Phe Asp Ile Leu Ala Thr
    50                  55                  60

Ser Phe Met Tyr Gly Ser Arg Thr Phe Ile Lys Tyr Pro Ala Asp Ile
65                  70                  75                  80

Pro Asp Phe Phe Lys Gln Ser Phe Pro Glu Gly Phe Thr Trp Glu Arg
                85                  90                  95

Val Thr Arg Tyr Glu Asp Gly Gly Val Val Thr Val Thr Gln Asp Thr
            100                 105                 110

Ser Leu Glu Asp Gly Glu Leu Val Tyr Asn Val Lys Val Arg Gly Val
        115                 120                 125

Asn Phe Pro Ser Asn Gly Pro Val Met Gln Lys Lys Thr Lys Gly Trp
    130                 135                 140

Glu Pro Asn Thr Glu Met Met Tyr Pro Ala Asp Gly Gly Leu Arg Gly
145                 150                 155                 160

Tyr Thr Asp Ile Ala Leu Lys Val Asp Gly Gly Gly His Leu His Cys
                165                 170                 175
```

```
Asn Phe Val Thr Thr Tyr Arg Ser Lys Lys Thr Val Gly Asn Ile Lys
            180                 185                 190

Met Pro Gly Val His Ala Val Asp His Arg Leu Glu Arg Ile Glu Glu
        195                 200                 205

Ser Asp Asn Glu Thr Tyr Val Val Gln Arg Glu Val Ala Val Ala Lys
    210                 215                 220

Tyr Ser Asn Leu Gly Gly Gly Met Asp Glu Leu Tyr Lys
225                 230                 235


<210> SEQ ID NO 16
<211> LENGTH: 344
<212> TYPE: PRT
<213> ORGANISM: artificial
<220> FEATURE:
<223> OTHER INFORMATION: fluorescent protein vsfGFP-0

<400> SEQUENCE: 16

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Ala Gln Val Gln Leu Val Glu Ser Gly Gly Ala
225                 230                 235                 240

Leu Val Gln Pro Gly Gly Ser Leu Arg Leu Ser Cys Ala Ala Ser Gly
                245                 250                 255

Phe Pro Val Asn Arg Tyr Ser Met Arg Trp Tyr Arg Gln Ala Pro Gly
            260                 265                 270

Lys Glu Arg Glu Trp Val Ala Gly Met Ser Ser Ala Gly Asp Arg Ser
        275                 280                 285

Ser Tyr Glu Asp Ser Val Lys Gly Arg Phe Thr Ile Ser Arg Asp Asp
    290                 295                 300
```

```
Ala Arg Asn Thr Val Tyr Leu Gln Met Asn Ser Leu Lys Pro Glu Asp
305                 310                 315                 320

Thr Ala Val Tyr Tyr Cys Asn Val Asn Val Gly Phe Glu Tyr Trp Gly
                325                 330                 335

Gln Gly Thr Gln Val Thr Val Ser
            340


<210> SEQ ID NO 17
<211> LENGTH: 219
<212> TYPE: PRT
<213> ORGANISM: artificial
<220> FEATURE:
<223> OTHER INFORMATION: fluorescent protein LanYFP

<400> SEQUENCE: 17

Met Ser Leu Pro Ala Thr His Glu Leu His Ile Phe Gly Ser Phe Asn
1               5                   10                  15

Gly Val Asp Phe Asp Met Val Gly Arg Gly Thr Gly Asn Pro Asn Asp
            20                  25                  30

Gly Tyr Glu Glu Leu Asn Leu Lys Ser Thr Lys Gly Ala Leu Gln Phe
        35                  40                  45

Ser Pro Trp Ile Leu Val Pro Gln Ile Gly Tyr Gly Phe His Gln Tyr
    50                  55                  60

Leu Pro Phe Pro Asp Gly Met Ser Pro Phe Gln Ala Ala Met Lys Asp
65                  70                  75                  80

Gly Ser Gly Tyr Gln Val His Arg Thr Met Gln Phe Glu Asp Gly Ala
                85                  90                  95

Ser Leu Thr Ser Asn Tyr Arg Tyr Thr Tyr Glu Gly Ser His Ile Lys
            100                 105                 110

Gly Glu Phe Gln Val Ile Gly Thr Gly Phe Pro Ala Asp Gly Pro Val
        115                 120                 125

Met Thr Asn Ser Leu Thr Ala Ala Asp Trp Cys Val Thr Lys Met Leu
    130                 135                 140

Tyr Pro Asn Asp Lys Thr Ile Ile Ser Thr Phe Asp Trp Thr Tyr Thr
145                 150                 155                 160

Thr Gly Ser Gly Lys Arg Tyr Gln Ser Thr Val Arg Thr Asn Tyr Thr
                165                 170                 175

Phe Ala Lys Pro Met Ala Ala Asn Ile Leu Lys Asn Gln Pro Met Phe
            180                 185                 190

Val Phe Arg Lys Thr Glu Leu Lys His Ser Lys Thr Glu Leu Asn Phe
        195                 200                 205

Lys Glu Trp Gln Lys Ala Phe Thr Asp Val Met
    210                 215


<210> SEQ ID NO 18
<211> LENGTH: 236
<212> TYPE: PRT
<213> ORGANISM: artificial
<220> FEATURE:
<223> OTHER INFORMATION: fluorescent protein dLanYFP

<400> SEQUENCE: 18

Met Val Ser Lys Gly Glu Glu Asp Asn Met Ala Ser Leu Pro Ala Thr
1               5                   10                  15

His Glu Leu His Ile Phe Gly Ser Phe Asn Gly Val Asp Phe Asp Met
            20                  25                  30

Val Gly Arg Gly Thr Gly Asn Pro Asn Asp Gly Tyr Glu Glu Leu Asn
        35                  40                  45
```

```
Leu Lys Ser Thr Lys Gly Asp Leu Gln Phe Ser Pro Trp Ile Leu Val
    50                  55                  60

Pro Gln Ile Gly Tyr Gly Phe His Gln Tyr Leu Pro Phe Pro Asp Gly
65                  70                  75                  80

Met Ser Pro Phe Gln Ala Ala Met Lys Asp Gly Ser Gly Tyr Gln Val
                85                  90                  95

His Arg Thr Met Gln Phe Glu Asp Gly Ala Ser Leu Thr Ser Asn Tyr
            100                 105                 110

Arg Tyr Thr Tyr Glu Gly Ser His Ile Lys Gly Glu Phe Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Val Thr Lys Met Leu Tyr Pro Asn Asp Lys Thr
145                 150                 155                 160

Ile Ile Ser Thr Phe Asp Trp Thr Tyr Thr Thr Gly Asn Gly Lys Arg
                165                 170                 175

Tyr Gln Ser Thr Ala Arg Thr Thr Tyr Thr Phe Ala Lys Pro Met Ala
            180                 185                 190

Ala Asn Ile Leu Lys Asn Gln Pro Met Phe Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235


<210> SEQ ID NO 19
<211> LENGTH: 225
<212> TYPE: PRT
<213> ORGANISM: artificial
<220> FEATURE:
<223> OTHER INFORMATION: fluorescent protein dVFP

<400> SEQUENCE: 19

Met Asn Val Ile Lys Pro Asp Met Arg Ile Lys Leu Arg Met Glu Gly
1               5                   10                  15

Ala Val Asn Gly His Lys Phe Val Ile Leu Gly Asp Gly Asn Gly Lys
            20                  25                  30

Pro Tyr Glu Gly Thr Gln Thr Ile Asp Val Thr Val Lys Glu Gly Gly
        35                  40                  45

Pro Leu Pro Phe Ala Tyr Asp Ile Leu Thr Ser Ala Phe Gln Tyr Gly
    50                  55                  60

Asn Arg Val Phe Thr Lys Tyr Pro Asp Asp Ile Ala Asp Tyr Phe Lys
65                  70                  75                  80

Gln Ser Phe Pro Val Gly Tyr Ser Trp Glu Arg Ser Met Thr Tyr Glu
                85                  90                  95

Asp Gly Gly Ile Cys Thr Val Ser Ser Asp Ile Lys Met Glu Gly Asn
            100                 105                 110

Ser Phe Ile Tyr Glu Ile Arg Phe His Gly Leu Asn Phe Pro Ser Asp
        115                 120                 125

Gly Pro Val Met Gln Lys Lys Thr Val Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Ser Thr
                165                 170                 175
```

```
Tyr Lys Ala Lys Arg Ala Val Gln Leu Pro Asp Tyr His Tyr Ile Asp
            180                 185                 190

His Arg Ile Glu Ile Leu Ser His Asp Lys Asp Tyr Asn Lys Val Lys
        195                 200                 205

Leu Cys Glu Asn Ala Ala Ala Arg Cys Ser Met Leu Pro Ser Gln Ala
    210                 215                 220

Lys
225
```

<210> SEQ ID NO 20
<211> LENGTH: 221
<212> TYPE: PRT
<213> ORGANISM: artificial
<220> FEATURE:
<223> OTHER INFORMATION: fluorescent protein ccal YFP1

<400> SEQUENCE: 20

```
Met Ser His Ser Lys Gln Val Ile Thr Gln Glu Met Lys Met Val Tyr
1               5                   10                  15

His Met Asp Gly Cys Val Asn Gly His Ser Phe Thr Ile Glu Gly Glu
            20                  25                  30

Gly Thr Gly Lys Pro Tyr Glu Gly Asn Gln Thr Leu Lys Leu Arg Val
        35                  40                  45

Thr Lys Gly Gly Pro Leu Pro Phe Ala Phe Asp Ile Leu Thr Ala Thr
    50                  55                  60

Phe Cys Tyr Gly Asn Arg Cys Phe Cys Glu Tyr Pro Glu Asp Met Pro
65                  70                  75                  80

Asp Tyr Tyr Lys Gln Ser Phe Pro Glu Gly Tyr Ser Phe Glu Arg Thr
                85                  90                  95

Met Met Phe Glu Asp Gly Ala Cys Cys Thr Thr Ser Val His Leu Ser
            100                 105                 110

Leu Thr Lys Asn Cys Phe Val His Asn Ser Thr Phe His Gly Val Asn
        115                 120                 125

Phe Pro Ala Asn Gly Pro Val Met Gln Lys Lys Thr Leu Asn Trp Glu
    130                 135                 140

Pro Ser Ser Glu Lys Ile Thr Pro Phe Glu Gly Asn Leu Lys Gly Asp
145                 150                 155                 160

Val Thr Met Phe Leu Lys Leu Glu Gly Gly Gln Gln His Arg Cys Gln
                165                 170                 175

Phe Gln Thr Thr Tyr Lys Ala His Lys Ala Val Lys Met Pro Pro Asn
            180                 185                 190

His Ile Ile Glu His Arg Leu Val Arg Ser Gln Asp Gly Asp Ala Val
        195                 200                 205

Gln Leu Lys Glu His Ala Val Ala Lys Cys Phe Thr Ala
    210                 215                 220
```

<210> SEQ ID NO 21
<211> LENGTH: 220
<212> TYPE: PRT
<213> ORGANISM: artificial
<220> FEATURE:
<223> OTHER INFORMATION: fluorescent protein efas GFP

<400> SEQUENCE: 21

```
Met Ala Leu Ser Lys Gln Gly Ile Gln Thr Asp Met Lys Met Thr Tyr
1               5                   10                  15

Ser Met Glu Gly Cys Val Asn Gly His Asn Phe Thr Val Lys Gly Gly
```

```
            20                  25                  30

Gly Asp Gly Asn Pro Tyr Glu Gly His Gln Glu Leu Arg Leu Cys Ile
        35                  40                  45

Thr Met Ala Lys Gly Glu Pro Val Pro Phe Ala Phe Asp Ile Leu Ser
    50                  55                  60

Ala Ala Phe Cys Tyr Gly Asn Arg Cys Phe Thr Lys Tyr Pro Asp Glu
65                  70                  75                  80

Ile Arg Asp Tyr Phe Lys Gln Ala Phe Pro Gly Gly Leu Ser Trp Glu
                85                  90                  95

Arg Ser Met Ala Phe Glu Asp Gly Ala Ser Ala Ala Val Thr Ala Glu
            100                 105                 110

Ile Ser Leu Glu Gly Asp Cys Phe Glu His Glu Cys Glu Phe Val Gly
        115                 120                 125

Val Asn Phe Pro Ala Asn Gly Pro Val Met Gln Lys Lys Thr Gln Gly
    130                 135                 140

Trp Glu Thr Ser Thr Glu Lys Met Thr Ala His Gly Lys Val Val Gln
145                 150                 155                 160

Gly Asn Val Pro Met Phe Leu Lys Leu Glu Gly Gly Gly Arg His Arg
                165                 170                 175

Cys Asp Phe Arg Thr Thr Tyr Lys Ala Lys Lys Asp Val Lys Met Pro
            180                 185                 190

Asn Ser His Phe Ile Thr His Cys Leu Val Arg Lys Gly Asp Gly Asn
        195                 200                 205

Asn Thr Glu Leu Ile Glu Asp Ala Glu Ala Arg Asn
    210                 215                 220


<210> SEQ ID NO 22
<211> LENGTH: 224
<212> TYPE: PRT
<213> ORGANISM: artificial
<220> FEATURE:
<223> OTHER INFORMATION: fluorescent protein pcDronpa (green)

<400> SEQUENCE: 22

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Ala Phe His Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Ser Tyr Glu
                85                  90                  95

Asp Gly Gly Ile Cys Ile Ala Thr Asn Asp Ile Thr Leu Asp Gly Asp
            100                 105                 110

Cys Tyr Ile Asn Glu Ile Arg Phe Asp Gly Val Asn Phe Pro Ala Asn
        115                 120                 125

Gly Pro Val Met Gln Lys Arg Thr Val Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
```

```
                165                 170                 175

Tyr Lys Ala Lys Lys Val Val Gln Leu Pro Asp Tyr His Phe Val Asp
            180                 185                 190

His His Ile Glu Ile Lys Ser His Asp Lys Asp Tyr Ser Asn Val Asn
        195                 200                 205

Leu His Glu His Ala Glu Ala His Ser Gly Leu Pro Arg Gln Ala Lys
    210                 215                 220


<210> SEQ ID NO 23
<211> LENGTH: 231
<212> TYPE: PRT
<213> ORGANISM: artificial
<220> FEATURE:
<223> OTHER INFORMATION: fluorescent protein aeur GFP

<400> SEQUENCE: 23

Met Ser Tyr Ser Lys Gln Gly Ile Val Gln Glu Met Lys Thr Lys Tyr
1               5                   10                  15

His Met Glu Gly Ser Val Asn Gly His Glu Phe Thr Ile Glu Gly Val
            20                  25                  30

Ala Thr Gly Tyr Pro Tyr Glu Gly Lys Gln Met Ser Glu Leu Val Ile
        35                  40                  45

Ile Lys Pro Lys Gly Lys Pro Leu Pro Phe Ser Phe Asp Ile Leu Ser
    50                  55                  60

Ser Val Phe Gln Tyr Gly Asn Arg Cys Phe Thr Lys Tyr Pro Ala Asp
65                  70                  75                  80

Ile Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Asn Ser Ile Phe His Gly
        115                 120                 125

Val Asn Phe Pro Ala Asp Gly Pro Val Met Lys Lys Gln Thr Ile Gly
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Tyr His Arg
                165                 170                 175

Cys Gln Phe His Ser Thr Tyr Lys Thr Glu Lys Pro Val Thr Leu Pro
            180                 185                 190

Pro Asn His Val Val Glu His Gln Ile Val Arg Thr Asp Leu Gly Gln
        195                 200                 205

Ser Ala Lys Gly Phe Thr Val Lys Leu Glu Ala Leu Ala Ala Ala His
    210                 215                 220

Val Asn Pro Leu Lys Val Gln
225                 230


<210> SEQ ID NO 24
<211> LENGTH: 316
<212> TYPE: PRT
<213> ORGANISM: artificial
<220> FEATURE:
<223> OTHER INFORMATION: fluorescent protein mRFP720

<400> SEQUENCE: 24

Met Ala Glu Gly Ser Val Ala Arg Gln Pro Asp Leu Leu Thr Cys Asp
1               5                   10                  15
```

-continued

```
Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Glu Val Ile Ala Glu Asp Arg Cys Ala Glu Val Glu Ser
            180                 185                 190

Lys Leu Gly Leu His Tyr Pro Ala Ser Phe Ile Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Val His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Lys Arg Val Ala
    290                 295                 300

Glu Arg Leu Ala Thr Gln Ile Gly Val Met Glu Glu
305                 310                 315


<210> SEQ ID NO 25
<211> LENGTH: 316
<212> TYPE: PRT
<213> ORGANISM: artificial
<220> FEATURE:
<223> OTHER INFORMATION: fluorescent protein iRFP720

<400> SEQUENCE: 25

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60
```

```
Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Ser Val Ile Ala Glu Asp Arg Cys Ala Glu Val Glu Ser
            180                 185                 190

Lys Leu Gly Leu His Tyr Pro Ala Ser Phe Ile Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Asn His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Glu Leu Val Ala
    290                 295                 300

Gln Val Leu Ala Trp Gln Ile Gly Val Met Glu Glu
305                 310                 315


<210> SEQ ID NO 26
<211> LENGTH: 335
<212> TYPE: PRT
<213> ORGANISM: artificial
<220> FEATURE:
<223> OTHER INFORMATION: fluorescent protein Wi-Phy

<400> SEQUENCE: 26

Met Ala Ser Met Thr Gly Gly Gln Gln Met Gly Arg Gly Ser Met Ser
1               5                   10                  15

Arg Asp Pro Leu Pro Phe Phe Pro Pro Leu Tyr Leu Gly Gly Pro Glu
            20                  25                  30

Ile Thr Thr Glu Asn Cys Glu Arg Glu Pro Ile His Ile Pro Gly Ser
        35                  40                  45

Ile Gln Pro His Gly Ala Leu Leu Thr Ala Asp Gly His Ser Gly Glu
    50                  55                  60

Val Leu Gln Met Ser Leu Asn Ala Ala Thr Phe Leu Gly Gln Glu Pro
65                  70                  75                  80

Thr Val Leu Arg Gly Gln Thr Leu Ala Ala Leu Leu Pro Glu Gln Trp
                85                  90                  95

Pro Ala Leu Gln Ala Ala Leu Pro Pro Gly Cys Pro Asp Ala Leu Gln
            100                 105                 110
```

```
Tyr Arg Ala Thr Leu Asp Trp Pro Ala Ala Gly His Leu Ser Leu Thr
        115                 120                 125

Val His Arg Val Gly Glu Leu Leu Ile Leu Glu Phe Glu Pro Thr Glu
    130                 135                 140

Ala Trp Asp Ser Thr Gly Pro His Ala Leu Arg Asn Ala Met Ser Ala
145                 150                 155                 160

Leu Glu Ser Ala Pro Asn Leu Arg Ala Leu Ala Glu Val Ala Thr Gln
                165                 170                 175

Thr Val Arg Glu Leu Thr Gly Phe Asp Arg Val Met Leu Tyr Lys Phe
            180                 185                 190

Ala Pro Asp Ala Thr Gly Glu Val Ile Ala Glu Ala Arg Arg Glu Gly
        195                 200                 205

Leu His Ala Phe Leu Gly His Arg Phe Pro Ala Ser His Ile Pro Ala
    210                 215                 220

Gln Ala Arg Ala Leu Tyr Thr Arg His Leu Leu Arg Leu Thr Ala Asp
225                 230                 235                 240

Thr Arg Ala Ala Ala Val Pro Leu Asp Pro Val Leu Asn Pro Gln Thr
                245                 250                 255

Asn Ala Pro Thr Pro Leu Gly Gly Ala Val Leu Arg Ala Thr Ser Pro
            260                 265                 270

Met His Met Gln Phe Leu Arg Asn Met Gly Val Gly Ser Ser Leu Ser
        275                 280                 285

Val Ser Val Val Val Gly Gly Gln Leu Trp Gly Leu Ile Ala Cys His
    290                 295                 300

His Gln Thr Pro Tyr Val Leu Pro Pro Asp Leu Arg Thr Thr Leu Glu
305                 310                 315                 320

Tyr Leu Gly Arg Glu Leu Ser Glu Gln Val Gln Val Lys Glu Ala
                325                 330                 335


<210> SEQ ID NO 27
<211> LENGTH: 320
<212> TYPE: PRT
<213> ORGANISM: artificial
<220> FEATURE:
<223> OTHER INFORMATION: fluorescent protein SNIFP

<400> SEQUENCE: 27

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140
```

```
Ser Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
            180                 185                 190

Glu Gly Leu His Ala Phe Leu Gly His Arg Phe Pro Ala Ser Leu Ile
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Phe Leu Arg Asn Met Gly Val Arg Ser Ser
            260                 265                 270

Leu Ser Val Ser Val Val Val Gly Gly Gln Leu Trp Gly Leu Ile Ala
        275                 280                 285

Cys His His Gln Thr Pro Tyr Val Leu Pro Pro Asp Leu Arg Thr Thr
    290                 295                 300

Leu Glu Tyr Leu Gly Arg Glu Leu Ser Glu Gln Val Gln Val Lys Glu
305                 310                 315                 320


<210> SEQ ID NO 28
<211> LENGTH: 321
<212> TYPE: PRT
<213> ORGANISM: artificial
<220> FEATURE:
<223> OTHER INFORMATION: fluorscent protein iFP2.0

<400> SEQUENCE: 28

Met Ala Arg Asp Pro Gln Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Val Ser Leu Asn Ala Ala Thr Phe Leu Gly Gln
    50                  55                  60

Glu Pro Thr Val Leu Arg Gly Gln Thr Leu Ala Ala Leu Leu Pro Asp
65                  70                  75                  80

Gln Trp Pro Ala Leu Gln Thr Ala Leu Pro Pro Gly Cys Gln Asp Ala
                85                  90                  95

Leu Gln Tyr Arg Ala Thr Leu Asp Trp Pro Ala Ala Gly His Leu Ser
            100                 105                 110

Leu Thr Val His Arg Val Ala Glu Leu Leu Ile Leu Glu Phe Glu Pro
        115                 120                 125

Thr Glu Ala Trp Asp Ser Ile Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Ser Gly Phe Asp Arg Val Met Leu Tyr
                165                 170                 175

Lys Phe Ala Pro Asp Ala Thr Gly Glu Val Ile Ala Glu Ala Arg Arg
            180                 185                 190
```

```
Glu Gly Met Gln Ala Tyr Leu Gly His Arg Phe Pro Ala Ser Thr Thr
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Val Gly Gly Gln Leu Trp Gly Leu Ile Val
        275                 280                 285

Cys His His Gln Thr Pro Tyr Val Leu Pro Pro Asp Leu Arg Thr Thr
    290                 295                 300

Leu Glu Tyr Leu Gly Arg Leu Leu Ser Leu Gln Val Gln Arg Lys Glu
305                 310                 315                 320

Ala


<210> SEQ ID NO 29
<211> LENGTH: 316
<212> TYPE: PRT
<213> ORGANISM: artificial
<220> FEATURE:
<223> OTHER INFORMATION: fluorescent protein iRFP713

<400> SEQUENCE: 29

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Glu Val Ile Ala Glu Asp Arg Cys Ala Glu Val Glu Ser
            180                 185                 190

Lys Leu Gly Leu His Tyr Pro Ala Ser Thr Val Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
```

```
225                 230                 235                 240

Ile Asp Leu Ser Phe Ala Ile Leu Arg Ser Val Ser Pro Val His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Glu Leu Val Ala
    290                 295                 300

Gln Val Leu Ala Trp Gln Ile Gly Val Met Glu Glu
305                 310                 315


<210> SEQ ID NO 30
<211> LENGTH: 321
<212> TYPE: PRT
<213> ORGANISM: artificial
<220> FEATURE:
<223> OTHER INFORMATION: fluorescent protein iFP1.4

<400> SEQUENCE: 30

Met Ala Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Val Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Ala Glu Leu Leu Ile Leu Glu Phe Glu Pro
        115                 120                 125

Thr Glu Ala Trp Asp Ser Ile Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Met Ile Ala Glu Ala Arg Arg
            180                 185                 190

Glu Gly Met Gln Ala Phe Leu Gly His Arg Phe Pro Ala Ser His Thr
        195                 200                 205

Pro Ala Gln Ala Arg Ala Leu Tyr Thr Arg His Leu Leu Arg Leu Thr
    210                 215                 220

Ala Asp Thr Arg Ala Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
                245                 250                 255

Ser Pro Met His Met Gln Tyr Leu Arg Asn Met Gly Val Gly Ser Ser
            260                 265                 270

Leu Ser Val Ser Val Val Val Gly Gly Gln Leu Trp Gly Leu Ile Val
```

```
        275                 280                 285

Cys His His Gln Thr Pro Tyr Val Leu Pro Pro Asp Leu Arg Thr Thr
    290                 295                 300

Leu Glu Glu Leu Gly Arg Lys Leu Ser Gly Gln Val Gln Arg Lys Glu
305                 310                 315                 320

Ala


<210> SEQ ID NO 31
<211> LENGTH: 320
<212> TYPE: PRT
<213> ORGANISM: artificial
<220> FEATURE:
<223> OTHER INFORMATION: fluorescent protein mIFP

<400> SEQUENCE: 31

Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asp Glu Thr Ala Thr Ile Ile Arg Glu Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Arg Ala Asp Leu Glu Ala Phe Leu Gly
            180                 185                 190

Asn Arg Tyr Pro Ala Ser Thr Ile Pro Gln Ile Ala Arg Arg Leu Tyr
        195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Ile His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Ala Glu Thr Cys
    290                 295                 300

Ala Ile Arg Ile Ala Thr Leu Glu Ser Phe Ala Gln Ser Gln Ser Lys
305                 310                 315                 320
```

<210> SEQ ID NO 32
<211> LENGTH: 315
<212> TYPE: PRT
<213> ORGANISM: artificial
<220> FEATURE:
<223> OTHER INFORMATION: fluorescent protein miRFP709

<400> SEQUENCE: 32

```
Met Val Ala Gly His Ala Ser Gly Ser Pro Ala Phe Gly Thr Ala Ser
1               5                   10                  15

His Ser Asn Cys Glu His Glu Glu Ile His Leu Ala Gly Ser Ile Gln
            20                  25                  30

Pro His Gly Ala Leu Leu Val Val Ser Glu His Asp His Arg Val Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Cys Gly Leu Met His Arg Pro
            100                 105                 110

Pro Glu Gly Gly Leu Ile Ile Glu Leu Glu Arg Ala Gly Pro Ser Ile
        115                 120                 125

Asp Leu Ser Gly Thr Leu Ala Pro Ala Leu Glu Arg Ile Arg Thr Ala
    130                 135                 140

Gly Ser Leu Arg Ala Leu Cys Asp Asp Thr Val Leu Leu Phe Gln Gln
145                 150                 155                 160

Cys Thr Gly Tyr Asp Arg Val Met Val Tyr Arg Phe Asp Glu Gln Gly
                165                 170                 175

His Gly Leu Val Phe Ser Glu Cys His Val Pro Gly Leu Glu Ser Tyr
            180                 185                 190

Phe Gly Asn Arg Tyr Pro Ser Ser Phe Ile Pro Gln Met Ala Arg Gln
        195                 200                 205

Leu Tyr Val Arg Gln Arg Val Arg Val Leu Val Asp Val Thr Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Ile His Leu Gln
                245                 250                 255

Phe Leu Lys Asp Met Gly Val Arg Ala Thr Leu Ala Val Ser Leu Val
            260                 265                 270

Val Gly Gly Lys Leu Trp Gly Leu Val Val Cys His His Tyr Leu Pro
        275                 280                 285

Arg Phe Ile Arg Phe Glu Leu Arg Ala Ile Cys Lys Arg Leu Ala Glu
    290                 295                 300

Arg Ile Ala Thr Arg Ile Thr Ala Leu Glu Ser
305                 310                 315
```

<210> SEQ ID NO 33
<211> LENGTH: 313
<212> TYPE: PRT
<213> ORGANISM: artificial
<220> FEATURE:
<223> OTHER INFORMATION: fluorescent protein miRFP

<400> SEQUENCE: 33

Met Val Ala Gly His Ala Ser Gly Ser Pro Asp Phe Gly Thr Ala Asp
1               5                   10                  15

Pro Ser Asp Cys Glu Arg Glu Glu Ile His Leu Ala Gly Ser Ile Gln
            20                  25                  30

Pro His Gly Thr Leu Leu Val Val Ser Glu Pro Asp His Arg Ile Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Asp Gly Leu Met His Arg Pro
            100                 105                 110

Pro Glu Gly Gly Leu Ile Ile Glu Leu Glu Arg Ala Gly Pro Pro Ile
        115                 120                 125

Asp Leu Ser Gly Thr Leu Ala Pro Ala Leu Glu Arg Ile Arg Thr Ala
    130                 135                 140

Gly Ser Leu Arg Ala Leu Cys Asp Asp Thr Ala Leu Leu Phe Gln Gln
145                 150                 155                 160

Cys Thr Gly Tyr Asp Arg Val Met Val Tyr Arg Phe Asp Glu Gln Gly
                165                 170                 175

His Gly Glu Val Tyr Ser Glu Ile His Val Thr Gly Leu Glu Ser Tyr
            180                 185                 190

Phe Gly Asn Arg Tyr Pro Ser Ser Leu Val Pro Gln Met Ala Arg Arg
        195                 200                 205

Leu Tyr Glu Arg Gln Arg Val Arg Val Leu Val Asp Val Ser Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Thr His Leu Gln
                245                 250                 255

Phe Leu Lys Asn Met Gly Val Arg Ala Thr Leu Val Val Ser Leu Val
            260                 265                 270

Val Gly Gly Lys Leu Trp Gly Leu Val Ile Cys His His Tyr Leu Pro
        275                 280                 285

Arg Phe Ile His Phe Glu Leu Arg Ala Ile Cys Glu Leu Leu Ala Glu
    290                 295                 300

Ala Ile Ala Thr Arg Ile Thr Ala Leu
305                 310

<210> SEQ ID NO 34
<211> LENGTH: 232
<212> TYPE: PRT
<213> ORGANISM: artificial
<220> FEATURE:
<223> OTHER INFORMATION: fluorescent protein M355NA

<400> SEQUENCE: 34

Met Ala Ser Phe Leu Thr Glu Thr Met Pro Phe Lys Thr Thr Ile Glu
1               5                   10                  15

Gly Thr Val Asn Gly His Tyr Phe Lys Cys Thr Gly Lys Gly Glu Gly
            20                  25                  30

Asn Pro Phe Glu Gly Thr Gln Glu Met Lys Ile Glu Val Ile Glu Gly 35 40 45

Gly Pro Leu Pro Phe Ala Phe His Ile Leu Ser Thr Ser Cys Met Tyr
50 55 60

Gly Ser Lys Thr Phe Ile Lys Tyr Val Ser Gly Ile Pro Asp Tyr Phe
65 70 75 80

Lys Gln Ser Phe Pro Glu Gly Phe Thr Trp Glu Arg Thr Thr Thr Tyr
85 90 95

Glu Asp Gly Gly Phe Leu Thr Ala His Gln Asp Thr Ser Leu Asp Gly
100 105 110

Asp Cys Leu Val Tyr Lys Val Lys Ile Leu Gly Asn Asn Phe Pro Ala
115 120 125

Asp Gly Pro Val Met Gln Asn Lys Ala Gly Arg Trp Glu Pro Cys Thr
130 135 140

Glu Ile Val Tyr Glu Val Asp Gly Val Leu Arg Gly Gln Ser Leu Met
145 150 155 160

Ala Leu Lys Cys Pro Gly Gly Arg His Leu Thr Cys His Leu His Thr
165 170 175

Thr Tyr Arg Ser Lys Lys Pro Ala Ser Ala Leu Lys Met Pro Gly Phe
180 185 190

His Phe Glu Asp His Arg Ile Glu Ile Met Glu Glu Val Glu Lys Gly
195 200 205

Lys Cys Tyr Lys Gln Tyr Glu Ala Ala Val Gly Arg Tyr Cys Asp Ala
210 215 220

Ala Pro Ser Lys Leu Gly His Asn
225 230

<210> SEQ ID NO 35
<211> LENGTH: 133
<212> TYPE: PRT
<213> ORGANISM: artificial
<220> FEATURE:
<223> OTHER INFORMATION: fluorescent protein smURFP

<400> SEQUENCE: 35

Met Ala Lys Thr Ser Glu Gln Arg Val Asn Ile Ala Thr Leu Leu Thr
1 5 10 15

Glu Asn Lys Lys Lys Ile Val Asp Lys Ala Ser Gln Asp Leu Trp Arg
20 25 30

Arg His Pro Asp Leu Ile Ala Pro Gly Gly Ile Ala Phe Ser Gln Arg
35 40 45

Asp Arg Ala Leu Cys Leu Arg Asp Tyr Gly Trp Phe Leu His Leu Ile
50 55 60

Thr Phe Cys Leu Leu Ala Gly Asp Lys Gly Pro Ile Glu Ser Ile Gly
65 70 75 80

Leu Ile Ser Ile Arg Glu Met Tyr Asn Ser Leu Gly Val Pro Val Pro
85 90 95

Ala Met Met Glu Ser Ile Arg Cys Leu Lys Glu Ala Ser Leu Ser Leu
100 105 110

Leu Asp Glu Glu Asp Ala Asn Glu Thr Ala Pro Tyr Phe Asp Tyr Ile
115 120 125

Ile Lys Ala Met Ser
130

<210> SEQ ID NO 36
<211> LENGTH: 289
<212> TYPE: PRT

```
<213> ORGANISM: artificial
<220> FEATURE:
<223> OTHER INFORMATION: fluorescent protein TDsmURFP

<400> SEQUENCE: 36

Met Ala Lys Thr Ser Glu Gln Arg Val Asn Ile Ala Thr Leu Leu Thr
1               5                   10                  15

Glu Asn Lys Lys Lys Ile Val Asp Lys Ala Ser Gln Asp Leu Trp Arg
            20                  25                  30

Arg His Pro Asp Leu Ile Ala Pro Gly Gly Ile Ala Phe Ser Gln Arg
        35                  40                  45

Asp Arg Ala Leu Cys Leu Arg Asp Tyr Gly Trp Phe Leu His Leu Ile
    50                  55                  60

Thr Phe Cys Leu Leu Ala Gly Asp Lys Gly Pro Ile Glu Ser Ile Gly
65                  70                  75                  80

Leu Ile Ser Ile Arg Glu Met Tyr Asn Ser Leu Gly Val Pro Val Pro
                85                  90                  95

Ala Met Met Glu Ser Ile Arg Cys Leu Lys Glu Ala Ser Leu Ser Leu
            100                 105                 110

Leu Asp Glu Glu Asp Ala Asn Glu Thr Ala Pro Tyr Phe Asp Tyr Ile
        115                 120                 125

Ile Lys Ala Met Ser Gly His Gly Thr Gly Ser Thr Gly Ser Gly Ser
    130                 135                 140

Ser Gly Thr Ala Ser Ser Glu Asp Asn Asn Met Ala Met Ala Lys Thr
145                 150                 155                 160

Ser Glu Gln Arg Val Asn Ile Ala Thr Leu Leu Thr Glu Asn Lys Lys
                165                 170                 175

Lys Ile Val Asp Lys Ala Ser Gln Asp Leu Trp Arg Arg His Pro Asp
            180                 185                 190

Leu Ile Ala Pro Gly Gly Ile Ala Phe Ser Gln Arg Asp Arg Ala Leu
        195                 200                 205

Cys Leu Arg Asp Tyr Gly Trp Phe Leu His Leu Ile Thr Phe Cys Leu
    210                 215                 220

Leu Ala Gly Asp Lys Gly Pro Ile Glu Ser Ile Gly Leu Ile Ser Ile
225                 230                 235                 240

Arg Glu Met Tyr Asn Ser Leu Gly Val Pro Val Pro Ala Met Met Glu
                245                 250                 255

Ser Ile Arg Cys Leu Lys Glu Ala Ser Leu Ser Leu Leu Asp Glu Glu
            260                 265                 270

Asp Ala Asn Glu Thr Ala Pro Tyr Phe Asp Tyr Ile Ile Lys Ala Met
        275                 280                 285

Ser


<210> SEQ ID NO 37
<211> LENGTH: 223
<212> TYPE: PRT
<213> ORGANISM: artificial
<220> FEATURE:
<223> OTHER INFORMATION: fluorescent protein LanFP2

<400> SEQUENCE: 37

Met Ser Leu Pro Thr Thr His Asp Leu His Ile Phe Gly Ser Val Asn
1               5                   10                  15

Gly Ala Glu Phe Asp Leu Val Gly Gly Gly Lys Gly Asn Pro Asn Asp
            20                  25                  30

Gly Thr Leu Glu Thr Ser Val Lys Ser Thr Arg Gly Ala Leu Pro Cys
```

```
        35                  40                  45

Ser Pro Leu Leu Ile Gly Pro Asn Leu Gly Tyr Gly Phe Tyr Gln Tyr
    50                  55                  60

Leu Pro Phe Pro Gly Gly Ala Ser Pro Phe Gln Thr Ala Ile Thr Asp
65                  70                  75                  80

Gly Gly Tyr Gln Val His Arg Val Phe Lys Phe Glu Asp Gly Gly Val
                85                  90                  95

Leu Ser Cys Asn Phe Arg Tyr Thr Tyr Glu Gly Gly Lys Ile Lys Gly
            100                 105                 110

Glu Phe Gln Leu Ile Gly Ser Gly Phe Pro Ala Gly Gly Pro Val Met
        115                 120                 125

Ser Gly Gly Leu Thr Thr Leu Asp Arg Ser Val Ala Lys Leu Gln Cys
    130                 135                 140

Ser Asp Asp Cys Thr Ile Thr Gly Thr Asn Asn Trp Ser Phe Cys Thr
145                 150                 155                 160

Thr Asp Gly Lys Arg His Gln Ala Asp Val Gln Thr Asn Tyr Thr Phe
                165                 170                 175

Ala Lys Pro Leu Pro Ala Gly Leu Lys Glu Lys Met Pro Ile Phe Leu
            180                 185                 190

Gly His Gln Ile Glu Val Lys Ala Ser Lys Thr Glu Ile Thr Leu Ser
        195                 200                 205

Glu Lys Val Lys Ala Phe Ile Asp Thr Val Gly Ser Gly Thr Gly
    210                 215                 220


<210> SEQ ID NO 38
<211> LENGTH: 231
<212> TYPE: PRT
<213> ORGANISM: artificial
<220> FEATURE:
<223> OTHER INFORMATION: fluorescent protein HcRed-Tandem

<400> SEQUENCE: 38

Arg Ser Pro Gly Met Ser Gly Leu Leu Lys Glu Ser Met Arg Ile Lys
1               5                   10                  15

Met Tyr Met Glu Gly Thr Val Asn Gly His Tyr Phe Lys Cys Glu Gly
            20                  25                  30

Glu Gly Asp Gly Asn Pro Phe Ala Gly Thr Gln Gly Met Arg Ile His
        35                  40                  45

Val Thr Glu Gly Ala Pro Leu Pro Phe Ala Phe Asp Ile Leu Ala Pro
    50                  55                  60

Cys Cys Ala Tyr Gly Ser Arg Thr Phe Val His His Thr Ala Glu Ile
65                  70                  75                  80

Pro Asp Phe Phe Lys Gln Ser Phe Pro Glu Gly Phe Thr Trp Glu Arg
                85                  90                  95

Thr Thr Thr Tyr Glu Asp Gly Gly Ile Leu Thr Ala His Gln Asp Thr
            100                 105                 110

Ser Leu Glu Gly Asn Cys Leu Ile Tyr Lys Val Lys Val His Gly Thr
        115                 120                 125

Asn Phe Pro Ala Asp Gly Pro Val Met Lys Asn Glu Ser Gly Gly Trp
    130                 135                 140

Glu Pro Ser Thr Glu Val Val Tyr Pro Glu Asn Gly Val Leu Cys Gly
145                 150                 155                 160

Arg Asn Val Met Ala Leu Lys Val Gly Asp Arg His Leu Ile Cys His
                165                 170                 175

Leu Tyr Thr Ser Tyr Lys Ser Lys Lys Ala Val Arg Ala Leu Thr Met
```

180 185 190

Pro Gly Phe His Phe Thr Asp Ile Arg Leu Gln Met Leu Arg Lys Lys
195 200 205

Lys Asp Glu Tyr Phe Glu Leu Tyr Glu Ala Ser Val Ala Arg Tyr Ser
210 215 220

Asp Leu Pro Glu Lys Ala Asn
225 230

<210> SEQ ID NO 39
<211> LENGTH: 226
<212> TYPE: PRT
<213> ORGANISM: artificial
<220> FEATURE:
<223> OTHER INFORMATION: fluorescent protein Skylan-S

<400> SEQUENCE: 39

Met Ser Ala Ile Lys Pro Asp Met Lys Ile Lys Leu Arg Met Glu Gly
1 5 10 15

Asn Val Asn Gly His His Phe Val Ile Asp Gly Asp Gly Thr Gly Lys
20 25 30

Pro Phe Glu Gly Lys Gln Ser Met Asp Leu Glu Val Lys Glu Gly Gly
35 40 45

Pro Leu Pro Phe Ala Phe Asp Ile Leu Thr Thr Ala Phe Ser Tyr Gly
50 55 60

Asn Arg Val Phe Ala Lys Tyr Pro Asp Asn Ile Gln Asp Tyr Phe Lys
65 70 75 80

Gln Ser Phe Pro Lys Gly Tyr Ser Trp Glu Arg Ser Leu Thr Phe Glu
85 90 95

Asp Gly Gly Ile Cys Asn Ala Arg Asn Asp Ile Thr Met Glu Gly Asp
100 105 110

Thr Phe Tyr Asn Lys Val Arg Phe Tyr Gly Thr Asn Phe Pro Ala Asn
115 120 125

Gly Pro Val Met Gln Lys Lys Thr Leu Lys Trp Glu Pro Ser Thr Glu
130 135 140

Lys Met Tyr Val Arg Asp Gly Val Leu Thr Gly Asp Val Glu Met Ala
145 150 155 160

Leu Leu Leu Glu Gly Asn Ala His Tyr Arg Cys Asp Phe Arg Thr Thr
165 170 175

Tyr Lys Ala Lys Glu Lys Gly Val Lys Leu Pro Gly Ala His Phe Val
180 185 190

Asp His Cys Ile Glu Ile Leu Ser His Asp Lys Asp Tyr Asn Lys Val
195 200 205

Lys Leu Tyr Glu His Ala Val Ala His Ser Gly Leu Pro Asp Asn Ala
210 215 220

Arg Arg
225

<210> SEQ ID NO 40
<211> LENGTH: 225
<212> TYPE: PRT
<213> ORGANISM: artificial
<220> FEATURE:
<223> OTHER INFORMATION: fluorescent protein VFP

<400> SEQUENCE: 40

Met Asn Val Ile Lys Pro Asp Met Arg Ile Lys Leu Arg Met Glu Gly
1 5 10 15

```
Ala Val Asn Gly His Lys Phe Val Ile Leu Gly Asp Gly Asn Gly Lys
            20                  25                  30

Pro Tyr Glu Gly Thr Gln Thr Ile Asp Val Thr Val Lys Glu Gly Gly
        35                  40                  45

Pro Leu Pro Phe Ala Tyr Asp Ile Leu Thr Ser Ala Phe Gln Tyr Gly
    50                  55                  60

Asn Arg Val Phe Thr Lys Tyr Pro Asp Asp Ile Ala Asp Tyr Phe Lys
65                  70                  75                  80

Gln Ser Phe Pro Val Gly Tyr Ser Trp Glu Arg Ser Met Thr Tyr Glu
                85                  90                  95

Asp Gly Gly Ile Cys Thr Val Ser Ser Asp Ile Lys Met Glu Gly Asn
            100                 105                 110

Ser Phe Ile Tyr Glu Ile Arg Phe His Gly Leu Asn Phe Pro Ser Asp
        115                 120                 125

Gly Pro Val Met Gln Lys Lys Thr Val Lys Trp Glu Pro Ser Thr Glu
    130                 135                 140

Lys Met Tyr Val Arg Asp Gly Val Leu Lys Gly Asp Val Asn Met Thr
145                 150                 155                 160

Leu Leu Leu Glu Gly Gly Gly His Tyr Arg Cys Asp Phe Lys Ser Thr
                165                 170                 175

Tyr Lys Ala Lys Arg Ala Val Gln Leu Pro Asp Tyr His Tyr Ile Asp
            180                 185                 190

His Arg Ile Glu Ile Leu Ser His Asp Lys Asp Tyr Asn Lys Val Lys
        195                 200                 205

Leu Cys Glu Asn Ala Ala Ala Arg Cys Ser Met Leu Pro Ser Gln Ala
    210                 215                 220

Lys
225


<210> SEQ ID NO 41
<211> LENGTH: 238
<212> TYPE: PRT
<213> ORGANISM: artificial
<220> FEATURE:
<223> OTHER INFORMATION: fluorescent protein GFPxm163

<400> SEQUENCE: 41

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140
```

```
Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Tyr Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235


<210> SEQ ID NO 42
<211> LENGTH: 230
<212> TYPE: PRT
<213> ORGANISM: artificial
<220> FEATURE:
<223> OTHER INFORMATION: fluorescent protein PlamGFP

<400> SEQUENCE: 42

Met Glu Ile Glu Asp Val Ile Lys Arg Asp Met Lys Ile Lys Leu Arg
1               5                   10                  15

Met Glu Gly Ala Val Asn Gly His Lys Phe Val Ile Ile Gly Asn Gly
            20                  25                  30

Asp Gly Lys Pro Tyr Glu Gly Thr Gln Thr Ile Asp Leu Glu Val Ile
        35                  40                  45

Glu Gly Ala Pro Leu Pro Phe Ala Phe Asp Ile Leu Thr Thr Val Phe
    50                  55                  60

Glu Tyr Gly Asn Arg Val Phe Ala Lys Tyr Pro Asn Glu Ile Val Asp
65                  70                  75                  80

Tyr Phe Lys Gln Ser Phe Pro Glu Gly Tyr Ser Trp Glu Arg Ser Met
                85                  90                  95

Thr Tyr Glu Asp Gly Gly Ile Cys Ile Ala Thr Asn Asn Ile Thr Leu
            100                 105                 110

Ser Lys Val Ile Asp Asn Cys Phe His Tyr Asn Ile Arg Phe Asp Gly
        115                 120                 125

Val Asn Phe Pro Pro Lys Ser Pro Val Leu Gln Lys Thr Thr Met Lys
    130                 135                 140

Trp Glu Pro Ser Thr Glu Ile Met Tyr Val Arg Asp Gly Val Leu Lys
145                 150                 155                 160

Gly Asp Val Asn Met Ala Leu Leu Ile Glu Gly Gly Gly His Tyr Arg
                165                 170                 175

Cys Asp Phe Lys Thr Ile Tyr Lys Ala Lys Lys Val Val Glu Leu Pro
            180                 185                 190

Asp Tyr His Phe Val Asp His Arg Ile Thr Ile Lys Ser His Asp Lys
        195                 200                 205

Asp Tyr Asn Lys Val Leu Leu His Glu His Ala Lys Ala Arg Tyr Gly
    210                 215                 220

Leu Gln Arg Lys Ala Lys
225                 230


<210> SEQ ID NO 43
<211> LENGTH: 225
<212> TYPE: PRT
<213> ORGANISM: artificial
<220> FEATURE:
```

<223> OTHER INFORMATION: fluorescent protein sarcGFP

<400> SEQUENCE: 43

Met Ser Val Ile Lys Gln Glu Met Lys Ile Lys Leu His Met Asp Gly
1 5 10 15

Asn Val Asn Gly His Ala Phe Val Ile Glu Gly Asp Gly Lys Gly Lys
20 25 30

Pro Tyr Asp Gly Thr Gln Thr Leu Asn Leu Ser Val Lys Glu Gly Ala
35 40 45

Pro Leu Pro Phe Ser Tyr Asp Ile Leu Thr Asn Ala Phe Gln Tyr Gly
50 55 60

Asn Arg Ala Phe Thr Lys Tyr Pro Ala Asp Ile Pro Asp Tyr Phe Lys
65 70 75 80

Gln Thr Phe Pro Glu Gly Tyr Ser Trp Glu Arg Thr Met Ser Tyr Glu
85 90 95

Asp Asn Ala Ile Cys Asn Val Arg Ser Glu Ile Ser Met Glu Gly Asp
100 105 110

Cys Phe Ile Tyr Lys Ile Arg Phe Asp Gly Lys Asn Phe Pro Pro Asn
115 120 125

Gly Pro Val Met Gln Lys Lys Thr Leu Lys Trp Glu Pro Ser Thr Glu
130 135 140

Met Met Tyr Ala Arg Asp Gly Phe Leu Met Gly Asp Val Asn Met Ala
145 150 155 160

Leu Leu Leu Glu Gly Gly Gly His His Arg Cys Asp Phe Lys Thr Ser
165 170 175

Tyr Lys Ala Ala Lys Lys Asn Val Gln Leu Pro Asp Tyr His Tyr Val
180 185 190

Asp His Arg Ile Glu Ile Leu Ser His Asp Arg Asp Tyr Asn Lys Val
195 200 205

Lys Leu Tyr Glu Asn Ala Val Ala Arg Tyr Ser Leu Leu Pro Ser Gln
210 215 220

Ala
225

<210> SEQ ID NO 44
<211> LENGTH: 230
<212> TYPE: PRT
<213> ORGANISM: artificial
<220> FEATURE:
<223> OTHER INFORMATION: fluorescent protein psamCFP

<400> SEQUENCE: 44

Met Ala Ser Thr Lys Asn Val Leu Pro Asn Met Met Thr Leu Thr Tyr
1 5 10 15

His Met Glu Gly Ser Val Asn Gly His Asn Phe Glu Ile Ile Gly Glu
20 25 30

Gly Thr Gly Asn Pro Lys Glu Gly Lys His Thr Ile Thr Leu Gln Val
35 40 45

Val Lys Gly Gly Pro Leu Pro Phe Ser Val Asp Ile Leu Ser Thr Val
50 55 60

Phe Gln Tyr Gly Asn Arg Cys Phe Thr Lys Tyr Pro Pro Asn Thr Val
65 70 75 80

Asp Tyr Phe Lys Asn Ser Cys Pro Pro Gly Tyr Thr Phe Glu Arg Ser
85 90 95

Phe Leu Tyr Glu Asp Gly Ala Val Cys Thr Ala Ser Gly Asp Ile Thr
100 105 110

```
Leu Ser Asp Asp Lys Ala Ser Phe His His Lys Ser Lys Phe Phe Gly
        115                 120                 125

Val Asn Phe Pro Asp Asp Gly Pro Val Met Lys Lys Lys Thr Thr Asp
    130                 135                 140

Trp Glu Pro Ser Cys Glu Lys Met Thr Pro Ser Gly Lys Thr Leu Lys
145                 150                 155                 160

Gly Asp Val Ile Glu Phe Leu Leu Leu Glu Gly Gly Gly Arg Tyr Lys
                165                 170                 175

Cys Gln Phe His Thr Val Tyr Arg Ala Lys Thr Glu Pro Lys Arg Met
            180                 185                 190

Pro Glu Phe His Phe Val Gln His Lys Leu Thr Arg Thr Asp Val Ser
        195                 200                 205

Asp Pro Leu Lys Gln Gln Trp Gln Leu Thr Glu Asp Ala Ala Ala Cys
    210                 215                 220

Glu Ser Cys Phe His Lys
225                 230


<210> SEQ ID NO 45
<211> LENGTH: 238
<212> TYPE: PRT
<213> ORGANISM: artificial
<220> FEATURE:
<223> OTHER INFORMATION: fluoresvcent protein GFPxm18

<400> SEQUENCE: 45

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Ala Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235
```

<210> SEQ ID NO 46
<211> LENGTH: 232
<212> TYPE: PRT
<213> ORGANISM: artificial
<220> FEATURE:
<223> OTHER INFORMATION: fluorescent protein Gamillus 0.2

<400> SEQUENCE: 46

```
Met Ala Ser Gly Arg Ala Leu Phe Gln Tyr Pro Met Thr Ser Lys Ile
1               5                   10                  15

Glu Leu Asn Gly Glu Ile Asn Gly Lys Lys Phe Lys Val Ala Gly Glu
            20                  25                  30

Gly Phe Thr Pro Asn Ser Gly Arg Phe Asn Met His Ala Tyr Cys Thr
        35                  40                  45

Thr Gly Asp Leu Pro Met Ser Trp Val Val Ile Ala Ser Pro Leu Gln
    50                  55                  60

Tyr Gly Phe His Met Phe Ala His Tyr Pro Glu Asp Ile Thr His Phe
65                  70                  75                  80

Phe Gln Glu Cys Phe Pro Gly Ser Tyr Thr Leu Asp Arg Thr Leu Arg
                85                  90                  95

Met Glu Gly Asp Gly Thr Leu Thr Thr His His Glu Tyr Ser Leu Lys
            100                 105                 110

Asp Gly Cys Val Thr Ser Lys Thr Thr Leu Asn Ala Ser Gly Phe Asp
        115                 120                 125

Pro Lys Gly Ala Thr Met Thr Lys Ser Phe Val Glu Gln Leu Pro Asn
    130                 135                 140

Gln Val Glu Ile Thr Ala Glu Gly Asn Gly Ile Arg Leu Thr Ser Thr
145                 150                 155                 160

Val Leu Tyr Leu Lys Lys Asp Gly Thr Ile Gln Ile Gly Arg Gln Asp
                165                 170                 175

Cys Ile Val Lys Pro Val Gly Gly Lys Lys Val Thr Gln Pro Lys Ala
            180                 185                 190

His Phe Leu His Thr Gln Ile Ile Gln Lys Lys Asp Pro Asn Asp Thr
        195                 200                 205

Arg Asp His Ile Val Gln Thr Glu Leu Ala Val Ala Gly Asn Pro Trp
    210                 215                 220

His Glu Pro Ser Ala Ser Ala Val
225                 230
```

<210> SEQ ID NO 47
<211> LENGTH: 239
<212> TYPE: PRT
<213> ORGANISM: artificial
<220> FEATURE:
<223> OTHER INFORMATION: fluorescent protein eGFP

<400> SEQUENCE: 47

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
```

-continued

```
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 48
<211> LENGTH: 239
<212> TYPE: PRT
<213> ORGANISM: artificial
<220> FEATURE:
<223> OTHER INFORMATION: fluorescent protein eYFP

<400> SEQUENCE: 48

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
```

195 200 205

Ser Lys Asp Pro Asn Glu Lys Arg Asp His Met Val Leu Leu Glu Phe
210 215 220

Val Thr Ala Ala Gly Ile Thr Leu Gly Met Asp Glu Leu Tyr Lys
225 230 235

<210> SEQ ID NO 49
<211> LENGTH: 239
<212> TYPE: PRT
<213> ORGANISM: artificial
<220> FEATURE:
<223> OTHER INFORMATION: fluorescent protein Venus

<400> SEQUENCE: 49

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Leu Ile
35 40 45

Cys Thr Thr Gly Lys Leu Pro Val Pro Trp Pro Thr Leu Val Thr Thr
50 55 60

Leu Gly Tyr Gly Leu Gln Cys Phe Ala Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

Val Lys Phe Glu Gly Asp Thr Leu Val Asn Arg Ile Glu Leu Lys Gly
115 120 125

Ile Asp Phe Lys Glu Asp Gly Asn Ile Leu Gly His Lys Leu Glu Tyr
130 135 140

Asn Tyr Asn Ser His Asn Val Tyr Ile Thr Ala Asp Lys Gln Lys Asn
145 150 155 160

Gly Ile Lys Ala Asn Phe Lys Ile Arg His Asn Ile Glu Asp Gly Gly
165 170 175

Val Gln Leu Ala Asp His Tyr Gln Gln Asn Thr Pro Ile Gly Asp Gly
180 185 190

Pro Val Leu Leu Pro Asp Asn His Tyr Leu Ser Tyr Gln Ser Ala Leu
195 200 205

Ser Lys Asp Pro Asn Glu Lys Arg Asp His Met Val Leu Leu Glu Phe
210 215 220

Val Thr Ala Ala Gly Ile Thr Leu Gly Met Asp Glu Leu Tyr Lys
225 230 235

<210> SEQ ID NO 50
<211> LENGTH: 236
<212> TYPE: PRT
<213> ORGANISM: artificial
<220> FEATURE:
<223> OTHER INFORMATION: fluorescent protein mOrange2

<400> SEQUENCE: 50

Met Val Ser Lys Gly Glu Glu Asn Asn Met Ala Ile Ile Lys Glu Phe
1 5 10 15

Met Arg Phe Lys Val Arg Met Glu Gly Ser Val Asn Gly His Glu Phe
20 25 30

```
Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro His Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Tyr Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Lys Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Asp Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 51
<211> LENGTH: 236
<212> TYPE: PRT
<213> ORGANISM: artificial
<220> FEATURE:
<223> OTHER INFORMATION: fluorescent protein mCherry

<400> SEQUENCE: 51

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160
```

```
Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235


<210> SEQ ID NO 52
<211> LENGTH: 237
<212> TYPE: PRT
<213> ORGANISM: artificial
<220> FEATURE:
<223> OTHER INFORMATION: fluorescent protein mTagBFP

<400> SEQUENCE: 52

Met Val Ser Lys Gly Glu Glu Leu Ile Lys Glu Asn Met His Met Lys
1               5                   10                  15

Leu Tyr Met Glu Gly Thr Val Asp Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
    130                 135                 140

Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
                165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
        195                 200                 205

Ala Asn Asn Glu Thr Tyr Val Glu Gln His Glu Val Ala Val Ala Arg
    210                 215                 220

Tyr Cys Asp Leu Pro Ser Lys Leu Gly His Lys Leu Asn
225                 230                 235


<210> SEQ ID NO 53
<211> LENGTH: 231
<212> TYPE: PRT
<213> ORGANISM: artificial
<220> FEATURE:
<223> OTHER INFORMATION: fluorescent protein ZsGreen

<400> SEQUENCE: 53
```

Met Ala Gln Ser Lys His Gly Leu Thr Lys Glu Met Thr Met Lys Tyr
1 5 10 15

Arg Met Glu Gly Cys Val Asp Gly His Lys Phe Val Ile Thr Gly Glu
20 25 30

Gly Ile Gly Tyr Pro Phe Lys Gly Lys Gln Ala Ile Asn Leu Cys Val
35 40 45

Val Glu Gly Gly Pro Leu Pro Phe Ala Glu Asp Ile Leu Ser Ala Ala
50 55 60

Phe Asn Tyr Gly Asn Arg Val Phe Thr Glu Tyr Pro Gln Asp Ile Val
65 70 75 80

Asp Tyr Phe Lys Asn Ser Cys Pro Ala Gly Tyr Thr Trp Asp Arg Ser
85 90 95

Phe Leu Phe Glu Asp Gly Ala Val Cys Ile Cys Asn Ala Asp Ile Thr
100 105 110

Val Ser Val Glu Glu Asn Cys Met Tyr His Glu Ser Lys Phe Tyr Gly
115 120 125

Val Asn Phe Pro Ala Asp Gly Pro Val Met Lys Lys Met Thr Asp Asn
130 135 140

Trp Glu Pro Ser Cys Glu Lys Ile Ile Pro Val Pro Lys Gln Gly Ile
145 150 155 160

Leu Lys Gly Asp Val Ser Met Tyr Leu Leu Leu Lys Asp Gly Gly Arg
165 170 175

Leu Arg Cys Gln Phe Asp Thr Val Tyr Lys Ala Lys Ser Val Pro Arg
180 185 190

Lys Met Pro Asp Trp His Phe Ile Gln His Lys Leu Thr Arg Glu Asp
195 200 205

Arg Ser Asp Ala Lys Asn Gln Lys Trp His Leu Thr Glu His Ala Ile
210 215 220

Ala Ser Gly Ser Ala Leu Pro
225 230

<210> SEQ ID NO 54
<211> LENGTH: 239
<212> TYPE: PRT
<213> ORGANISM: artificial
<220> FEATURE:
<223> OTHER INFORMATION: fluorescent protein YPet

<400> SEQUENCE: 54

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Leu Leu
35 40 45

Cys Thr Thr Gly Lys Leu Pro Val Pro Trp Pro Thr Leu Val Thr Thr
50 55 60

Leu Gly Tyr Gly Val Gln Cys Phe Ala Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

Val Lys Phe Glu Gly Asp Thr Leu Val Asn Arg Ile Glu Leu Lys Gly
115 120 125

```
Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Lys
225                 230                 235


<210> SEQ ID NO 55
<211> LENGTH: 239
<212> TYPE: PRT
<213> ORGANISM: artificial
<220> FEATURE:
<223> OTHER INFORMATION: fluorescent protein mCitrine

<400> SEQUENCE: 55

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 56
```

```
<211> LENGTH: 238
<212> TYPE: PRT
<213> ORGANISM: artificial
<220> FEATURE:
<223> OTHER INFORMATION: fluorescent protein CFP

<400> SEQUENCE: 56

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 57
<211> LENGTH: 239
<212> TYPE: PRT
<213> ORGANISM: artificial
<220> FEATURE:
<223> OTHER INFORMATION: fluorescent protein eCFP

<400> SEQUENCE: 57

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
```

```
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 58
<211> LENGTH: 238
<212> TYPE: PRT
<213> ORGANISM: artificial
<220> FEATURE:
<223> OTHER INFORMATION: fluorescent protein GFP

<400> SEQUENCE: 58

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
```

```
    210                 215                 220

Thr Ala Ala Gly Ile Thr His Gly Met Asp Glu Leu Tyr Lys
225                 230                 235


<210> SEQ ID NO 59
<211> LENGTH: 316
<212> TYPE: PRT
<213> ORGANISM: Artificial Sequence
<220> FEATURE:
<223> OTHER INFORMATION: iRFP720

<400> SEQUENCE: 59

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Ser Val Ile Ala Glu Asp Arg Cys Ala Glu Val Glu Ser
            180                 185                 190

Lys Leu Gly Leu His Tyr Pro Ala Ser Phe Ile Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Asn His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Glu Leu Val Ala
    290                 295                 300

Gln Val Leu Ala Trp Gln Ile Gly Val Met Glu Glu
305                 310                 315


<210> SEQ ID NO 60
<211> LENGTH: 476
<212> TYPE: PRT
```

```
<213> ORGANISM: Artificial Sequence
<220> FEATURE:
<223> OTHER INFORMATION: tdTomato

<400> SEQUENCE: 60

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
    210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Lys Thr Met
    370                 375                 380

Gly Trp Glu Ala Ser Thr Glu Arg Leu Tyr Pro Arg Asp Gly Val Leu
```

-continued

```
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
        435                 440                 445

Glu Asp Tyr Thr Ile Val Glu Gln Tyr Glu Arg Ser Glu Gly Arg His
    450                 455                 460

His Leu Phe Leu Tyr Gly Met Asp Glu Leu Tyr Lys
465                 470                 475


<210> SEQ ID NO 61
<211> LENGTH: 238
<212> TYPE: PRT
<213> ORGANISM: Artificial Sequence
<220> FEATURE:
<223> OTHER INFORMATION: sfGFP

<400> SEQUENCE: 61

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```